US010201282B2

(12) United States Patent
Shu et al.

(10) Patent No.: US 10,201,282 B2
(45) Date of Patent: Feb. 12, 2019

(54) GENETICALLY ENCODED INFRARED FLUORESCENT PROTEASE REPORTERS

(71) Applicant: The Regents of the University of California, Oakland, CA (US)

(72) Inventors: Xiaokun Shu, San Francisco, CA (US); Tsz-Leung To, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/301,707

(22) PCT Filed: Apr. 3, 2015

(86) PCT No.: PCT/US2015/024307
§ 371 (c)(1),
(2) Date: Oct. 3, 2016

(87) PCT Pub. No.: WO2015/154006
PCT Pub. Date: Oct. 8, 2015

(65) Prior Publication Data
US 2017/0188835 A1 Jul. 6, 2017

Related U.S. Application Data

(60) Provisional application No. 61/974,857, filed on Apr. 3, 2014.

(51) Int. Cl.
| | | |
|---|---|---|
| C12Q 1/37 | (2006.01) |
| A61B 5/00 | (2006.01) |
| A61K 49/00 | (2006.01) |
| C12N 9/50 | (2006.01) |
| G01N 21/64 | (2006.01) |

(52) U.S. Cl.
CPC .......... *A61B 5/0071* (2013.01); *A61B 5/4848* (2013.01); *A61K 49/0056* (2013.01); *C12N 9/503* (2013.01); *C12Q 1/37* (2013.01); *C12Y 304/2206* (2013.01); *C12Y 304/22056* (2013.01); *G01N 21/6428* (2013.01); *G01N 21/6456* (2013.01); *G01N 2333/96413* (2013.01); *G01N 2510/00* (2013.01); *G01N 2800/52* (2013.01)

(58) Field of Classification Search
CPC . A61B 5/71; A61K 49/56; C12Q 1/37; C07K 2319/60
See application file for complete search history.

(56) References Cited

U.S. PATENT DOCUMENTS

| 4,673,641 A | 6/1987 | George et al. |
| 9,815,870 B2 | 11/2017 | Yu et al. |
| 2015/0353609 A1 | 12/2015 | Yu et al. |

OTHER PUBLICATIONS

Shu et al. 2009; Mammalian expression of infrared fluorescent proteins engineered from a bacterial phytochome. Science 324: 804-807.*
Filonov et al. 2011; Bright and stable near-ifrared fluorescent protein for invivo imaging. Nature Biotechnology. 29(8): 757-763.*
Abraham et al., "Pharmacological and Clinical Aspects of Heme Oxygenase." Pharmacological Reviews, 60:79-127 (2008).
Albeck et al, "Quantitative analysis of pathways controlling extrinsic apoptosis in single cells." Mol Cell., 30(1): 11-25 (2008).
Altschul, S. et al., "Basic Local Alignment Search Tool", *J. Mol. Biol.*, vol. 215, pp. 403-410 (1990).
Altschul, S. et al., "Gapped BLAST and PSI-BLAST: a new generation of protein database search programs", *Nucleic Acids Research*, vol. 25, No. 17, pp. 3389-3402 (1997).
Baird et al., "Circular permutation and receptor insertion within green fluorescent proteins." PNAS, 96: 11241-11246 (1999).
Batzer, M. et al., "Enhanced evolutionary PCR using oligonucleotides with inosine at the 3'-terminus", *Nucleic Acids Research*, vol. 19, No. 18, p. 5081 (1991).
Bellini and Papiz, "Dimerization properties of the RpBphP2 chromophore-binding domain crystallized by homologue-directed mutagenesis." Research Papers, Acta Cryst, D68, 1058-1066 (2012).
Berkelman and Lagarias, "Visualization of bilin-linked peptides and proteins in polyacrylamide gels." Analytical Biochemistry 156, 194-201 (1986).
Buss et al., "The six amino-terminal amino acids of p60src are sufficient to cause myristylation of p21v-ras." Mol. Cell. Biol. 8:3960-3963 (1988).
Cabantous et al., "Protein tagging and detection with engineered self-assembling fragments of green fluorescent protein." Nature Biotechnology, 23:1, 102-107 (2005).
Chae et al., "Molecular Mechanism of Staurosporine-Induced Apoptosis in Osteoblasts." Pharmaological Research, 42:4 (2000).
Chalfie, M., et al., "Green fluorescent protein as a marker for gene expression." Science 263:802-805 (1994).
Cody et al., "Chemical structure of the hexapeptide chromophore of the Aequorea green-fluorescent protein." Biochemistry 32:1212-1218 (1993).

(Continued)

*Primary Examiner* — Karen Cochrane Carlson
(74) *Attorney, Agent, or Firm* — Morgan, Lewis & Bockius LLP; Jeffry S. Mann; Louis T. Nguyen

(57) ABSTRACT

The invention described herein features infrared fluorescent protease reporters (iProteases) and methods of use thereof. The iProteases can be used in in vivo and in vitro assays to detect protease activity and disease states associated with protease activity. In a still further embodiment, the present invention provides a kit comprising any of the above described polynucleotides. In a further aspect, the present invention provides a method of in vivo optical imaging. In a still further embodiment, the in vivo imaging is performed in a living animal. In a further aspect, the present invention provides a method of detecting protease activity, the method comprising expressing a polypeptide according to any of those described above in a cell.

19 Claims, 5 Drawing Sheets
Specification includes a Sequence Listing.

(56) References Cited

OTHER PUBLICATIONS

Contag and Bachmann, "Advances in In Vivo Bioluminescence Imaging of Gene Expression." Annu. Rev. Biomed. Eng., 4:235-60 (2002).
Cui, L. et al. "Relevant expression of Drosophila heme oxygenase is necessary for the normal development of insect tissues." Biochemical and Biophysical Research Communications. Biochem Biophys Res Commun 377, 1156-1161 (2008).
Day and Davidson, "The fluorescent protein palette: tools for cellular imaging." Chem Soc Rev 38, 2887-2921 (2009).
De Crescenzo et al., "Real-Time Monitoring of the Interactions of Two-Stranded de Novo Designed Coiled-Coils: Effect of Chain Length on the Kinetic and Thermodynamic Constants of Binding." Biochemistry, 42, 1754-1763 (2003).
Fischer and Lagarias, Proc. Natl. Acad. Sci. U.S.A., "Harnessing phytochrome's glowing potential." 101, 17334 (2004).
Filonov, G. S. et al. "Bright and stable near-infrared fluorescent protein for in vivo imaging." Nat Biotechnol 29, 757-761 (2011).
Giraud et al., "Bacteriophytochrome controls photosystem synthesis in anoxygenic bacteria." Nature 417:202-205 (2002).
Giraud and Verméglio, "Bacteriophytochromes in anoxygenic photosynthetic bacteria." Photosyn Res 97, 141-153 (2008).
Gossen and Bujard, "Tight control of gene expression in mammalian cells by tetracycline-responsive promoters." PNAS 89:5547 (1992).
Hancock et al., "A CAAX or a CAAL motif and a second signal are sufficient for plasma membrane targeting of ras proteins." EMBO J. 10:4033-4039 (1991).
Heim et al., "Wavelength mutations and posttranslational autoxidation of green fluorescent protein." PNAS USA, 91(26):12501-4 (1994).
Heim and Tsien, "Engineering green fluorescent protein for improved brightness, longer wavelengths and fluorescence resonance energy transfer." Curr. Biol. 6:178-182 (1996).
Henikoff, S. and Henikoff, J., "Amino acid substitution matrices from protein blocks", Proc. Natl., Acad. Sci. USA, vol. 89, pp. 10915-10919 (1992).
Jacak et al., "Computational protein design with explicit consideration of surface hydrophobic patches." Proteins 80, 825-838 (2011).
Jöbsis, F.F., "Noninvasive, infrared monitoring of cerebral and myocardial oxygen sufficiency and circulatory parameters." Science, 198, 1264 (1977).
Kakitani, T. and Kakitani, H. "Theoretical Study of Optical Spectra and Conformation of the Chromophore of Hypsorhodopsin." Photochem Photobiol 32, 707-709 (1980).
Karniol et al., "Phylogenetic analysis of the phytochrome superfamily reveals distinct microbial subfamilies of photoreceptors." Biochem J 392, 103 (2005).
Kremers et al., "Fluorescent proteins at a glance." Journal of Cell Science 124, 2676-2676 (2011).
Lee and Richards, "The interpretation of protein structures: estimation of static accessibility." J Mol Biol 55, 379-400 (1971).
Livet, J. et al. "Transgenic strategies for combinatorial expression of fluorescent proteins in the nervous system." Nature 450, 56-62 (2007).
McCafferty, J. et al., "Phage antibodies: filamentous phage displaying antibody variable domains", Nature, vol. 348, pp. 552-554 (1990).
Miyawaki, A. et al., "Fluorescent indicators for Ca2+ based on green fluorescent proteins and calmodulin." Nature 388, 882-887 (1997).
Morise, H., et al., "Intermolecular energy transfer in the bioluminescent system of Aequorea" Biochemistry 13:2656-2662 (1974).
Moelbert, S. et al., "Correlation between sequence hydrophobicity and surface-exposure pattern of database proteins." Protein Science 13, 752-762 (2004).
Nakao et al., "Biliverdin Protects the Functional Integrity of a Transplanted Syngeneic Small Bowel." Gastroenterology, 127: 595-606 (2004).
Needleman, S. et al., "A General Method Applicable to the Search for Similarities in the Amino Acid Sequence of Two Proteins", J. Mol. Biol., vol. 48, pp. 443-453 (1970).
Neering et al., "Transduction of primitive human hematopoietic cells with recombinant adenovirus vectors." Blood 88:1147-1155 (1996).
Nicholls et al., "Mechanism of a Genetically Encoded Dark-to-Bright Reporter for Caspase Activity." Journal of Biol. Chem., 286: 28 (2011).
Ntziachristos et al., "Visualization of antitumor treatment by mens of fluorescence molecular tomography with an annexin V-Cy5.5 conjugate." PNAS, 101: 33, 12294-12299 (2004).
Ohtsuka, E. et al., "An Alternative Approach to Deoxyoligonucleotides as Hybridization Probes by Insertion of Deoxyinosine at Ambiguous Codon Positions", The Journal of Biological Chemistry, vol. 260, No. 5, pp. 2605-2608 (1985).
Ollinger et al., "Therapeutic Applications of Bilirubin and Biliverdin in Transplantation." Antioxidants & Redox Signaling, 9: 12, 2175 (2007).
Oligino et al.,"Drug inducible transgene expression in brain using a herpes simplex virus vector." Gene Ther. 5:491-496 (1998).
Ormö, M., et al., "Crystal structure of the Aequorea victoria green fluorescent protein." Science 273:1392-1395 (1996).
Pearson and Lipman, "Improved tools for biological sequence comparison", Proc. Natl. Acad. Sci. USA, vol. 85, pp. 2444-2448 (1988).
Poss and Tonegawa, "Heme oxygenase 1 is required for mammalian iron reutilization." Proc Natl Acad Sci USA 94, 10919-10924 (1997).
Prasher et al., "Primary structure of the Aequorea victoria green-fluorescent protein." Gene 111:229-233 (1992).
Prendergrast and Mann, "Chemical and physical properties of aequorin and the green fluorescent protein isolated from Aequorea forskÅlea." Biochemistry 17:3448-3453 (1978).
Rehm et al., "Single-cell Fluorescence Resonance Energy Transfer Analysis Demonstrates That Caspase Activation during Apoptosis Is a Rapid Process." The Journ. of Biol. Chem., 277: 27, 24506-24514 (2002).
Rendahl et al., "Regulation of gene expression in vivo following transduction by two separate rAAV vectors." Nat. Biotechnol. 16:757-761 (1998).
Rockwell, N. C. "The Structure of Phytochrome: A Picture Is Worth a Thousand Spectra." The Plant Cell Online 18, 4-14 (2006).
Rossolini et al., "Use of deoxyinosine-containing primers vs degenerate primers for polymerase chain reaction based on ambiguous sequence information." Mol. Cell. Probes 8:91-98 (1994).
Rusch et al., "The Sorcerer II Global Ocean Sampling Expedition: Northwest Atlantic through Eastern Tropical Pacific." PLOS Biology, 5: 3, 398431 (2007).
Sakaue-Sawano et al. "Visualizing Spatiotemporal Dynamics of Multicellular Cell-Cycle Progression." Cell 132, 487-498 (2008).
Schwede, T. et al, "Swiss-Model: an automated protein homology-modeling server." Nucleic Acids Res 31, 3381-3385 (2003).
Shcherbo et al., "Bright far-red fluorescent protein for whole-body imaging." Nat. Methods, 4(9):741 (2007).
Shu, X. et al. "Mammalian expression of infrared fluorescent proteins engineered from a bacterial phytochrome." Science 324, 804-807 (2009).
Shkrob et al., "Far-red fluorescent proteins evolved from a blue chromoprotein from Actinia equina." Biochem. J. 392, 649 (2005).
Smith and Waterman, "Comparison of Biosequences", Advances in Applied Mathematics, vol. 2, pp. 482-489 (1981).
To et al., "Rationally designed fluorogenic protese reporter visualizes spatiotemporal dynamics of apoptosis in vivo." PNAS, 112(11) pp. 3338-3343 (2015).
Tsien, R. Y. "Constructing and exploiting the fluorescent protein paintbox." (Nobel Lecture). Angew Chem Int Ed Engl 48, 5612-5626 (2009).
Ulijasz and Vierstra, "Phytochrome structure and photochemistry: recent advances toward a complete molecular picture." Curr Opin Plant Biol 14, 498-506 (2011).

(56) References Cited

OTHER PUBLICATIONS

Wagner et al., "A light-sensing knot revealed by the structure of the chromophore-binding domain of phytochrome." Nature 438, 325-331 (2005).

Wagner et al., "High Resolution Structure of Deinococcus Bacteriophytochrome Yields New Insights into Phytochrome Architecture and Evolution." J Biol Chem 282, 12298-12309 (2007).

Wang and Hazelrigg, "Implications for bcd mRNA localization from spatial distribution of exu protein in *Drosophila oogenesis*." Nature, 369:400-403 (1994).

Wang et al., "Positive and negative regulation of gene expression in eukaryotic cells with an inducible transcriptional regulator." Gene Ther. 4:432-441 (1997).

Wang et al., "Evolution of new nonantibody proteins via iterative somatic hypermutation." PNAS USA, 101, 16745 (2004).

Wang, Y. et al. Visualizing the mechanical activation of Src. Nature 434, 1040-1045 (2005).

Ward and Cormier, "Energy transfer via protein-protein interaction in *Renilla* bioluminescence." Photochem. Photobiol. 27:389-396 (1978).

Ward, W., "Spectral Perturbations of the Aequorea Green-Fluorescent Protein", Photochem. Photobiol. Rev. 4:1-57 (1982).

Ward, W. et al., "Spectrophotometric identity of the energy transfer chromophores in *Renilla* and *Aequorea* green fluorescent proteins." Photochem. Photobiol. Rev. 31:611-615 (1980).

Weissleder and Ntziachristos, "Shedding light onto live molecular targets." Nat. Med. 9, 123 (2003).

Yang, F. et al., "The molecular structure of green fluorescent protein." Nature Biotech. 14:1246-1251 (1996).

Yang, X. et al., "Temperature-scan cryocrystallography reveals reaction intermediates in bacteriophytochrome." Nature 479, 428-432 (2011).

Yang, X. et al.,"Crystal structure of the chromophore binding domain of an unusual bacteriophytochrome, RpBphP3, reveals residues that modulate photoconversion." Proc Natl Acad Sci USA 104, 12571-12576 (2007).

Yokoe and Meyer, "Spatial dynamics of GFP-tagged proteins investigated by local fluorescence enhancement." Nature Biotech. 14:1252-1256 (1996).

Zaccolo, M., "Discrete Microdomains with High Concentration of cAMP in Stimulated Rat Neonatal Cardiac Myocytes." Science 295, 1711-1715 (2002).

Zhang, J. et al., "Insulin disrupts beta-adrenergic signaling to protein kinase A in adipocytes." Nature 437, 569-573 (2005).

\* cited by examiner

SEQUENCE LISTING

<160> NUMBER OF SEQ ID NOS: 52

<210> SEQ ID NO 1
<211> LENGTH: 1671
<212> TYPE: DNA
<213> ORGANISM: Artificial Sequence
<220> FEATURE:
<223> OTHER INFORMATION: (Nucleic acid sequence of iTEV(+) 1.0)

<400> SEQUENCE: 1

| | | |
|---|---|---|
| atgtccaaag gagaagaact gtttaccggt gttgtgccaa ttttggttga actcgatggt | 60 |
| gatgtcaacg gacataagtt ctcagtgaga ggcgaaggag aaggtgacgc caccattgga | 120 |
| aaattgactc ttaaattcat ctgtactact ggtaaacttc ctgtaccatg gccgactctc | 180 |
| gtaacaacgc ttacgtacgg agttcagtgc ttttcgagat acccagacca tatgaaaaga | 240 |
| catgactttt ttaagtcggc tatgcctgaa ggttacgtgc aagaaagaac aatttcgttc | 300 |
| aaagatgatg gaaaatataa actagagca gttgttaaat ttgaaggaga actttggtt | 360 |
| aaccgcattg aactgaaagg aacagatttt aaagaagatg gaatattct tggacacaaa | 420 |
| ctcgaataca atttaatag tcataacgta tacatcactg ctgataagca aaagaacgga | 480 |
| attaaagcga atttcacagt acgccataat gtagaagatg gcagtgttca acttgccgac | 540 |
| cattaccaac aaaacacccc tattggagac ggtccggtac ttcttcctga taatcactac | 600 |
| ctctcaacac aaacagtcct gagcaaagat ccaaatgaaa aggaggcag cggatccacc | 660 |
| actaacattg cgccggctct ggacggtgcg tttcatcgta tcacttcttc atcctccctg | 720 |
| atgggcctgt gtgacgaaac cgcgactatt atccgtgaga ttactggcta cgaccgtgtg | 780 |
| atggtagtac gtttcgatga agagggtaat ggcgaaattc tgtccgaacg tcgtcgtgcg | 840 |
| gacctggaag cgttcctggg taaccgctac ccggcgtcta ctattccgca gatcgctcgt | 900 |
| cgcctgtacg aacataaccg tgttcgcctg ctggtagatg tgaactatac tccggttccg | 960 |
| ctacagccgc gcatcagccc gctgaacggt cgtgatctgg atatgtccct gtcttgcctg | 1020 |
| cgctctatgt ccccgatcca ccagaaatac atgcaggaca tgggcgttgg cgcgaccctg | 1080 |
| gtttgctctc tgatggtgtc tggtcgtctg tggggtctga tcgcttgcca ccactacgaa | 1140 |
| ccgcgcttcg ttccgttcca cattcgcgct gctggcgaag cgctggcgga aacttgtgcg | 1200 |
| atccgcatcg cgacgctgga gagctttgca cagtctcagt ccaaagaaaa tctctacttc | 1260 |
| cagagtgaat tcgcgtttct ggctaactgt gaacgcgagc agatccacct ggcgggctcc | 1320 |
| attcagccgc acggtatcct gctggctgtg aaagagccgg acaacgtggt gatccaggct | 1380 |
| tctattaacg ctgcggagtt cctgaacacc aactctgttg ttggccgtcc gctgcgtgac | 1440 |
| ctgggcggcg atctgccttt gcagatcctg ccgcacctga acgcccgct gcacctggct | 1500 |
| ccgatgaccc tgcgttgtac cgtgggttct ccgccgcgtc gtgtggactg taccattcat | 1560 |
| cgtccgtcta acgcggcct gatcgtagaa ctggaaccag caaccaagct cgagggaggc | 1620 |
| agccgggacc acatggtgct gcacgagtac gtgaacgccg ccggcatcac a | 1671 |

<210> SEQ ID NO 2
<211> LENGTH: 1656
<212> TYPE: DNA
<213> ORGANISM: Artificial Sequence
<220> FEATURE:
<223> OTHER INFORMATION: (Nucleic acid sequence of iTEV(+) 2.1)

<400> SEQUENCE: 2
atgtccaaag gagaagaact gtttaccggt gttgtgccaa ttttggttga actcgatggt    60

```
gatgtcaacg gacataagtt ctcagtgaga ggcgaaggag aaggtgacgc caccattgga     120
aaattgactc ttaaattcat ctgtactact ggtaaacttc ctgtaccatg gccgactctc     180
gtaacaacgc ttacgtacgg agttcagtgc ttttcgagat acccagacca tatgaaaaga     240
catgactttt ttaagtcggc tatgcctgaa ggttacgtgc aagaaagaac aatttcgttc     300
aaagatgatg gaaaatataa aactagagca gttgttaaat ttgaaggaga tactttggtt     360
aaccgcattg aactgaaagg aacagatttt aagaagatg gtaatattct tggacacaaa     420
ctcgaataca attttaatag tcataacgta tacatcactg ctgataagca aagaacgga      480 attaaagcga atttcacagt acgccataat gtagaagatg gcagtgttca acttgccgac     540
cattaccaac aaaacacccc tattggagac ggtccggtac ttcttcctga taatcactac     600
ctctcaacac aaacagtcct gagcaaagat ccaaatgaaa aaggaggcag cggatccacc     660
actaacattg cgccggctct ggacggtgcg tttcatcgta tcacttcttc atcctccctg     720
atgggcctgt gtgacgaaac cgcgactatt atccgtgaga ttactggcta cgaccgtgtg     780
atggtagtac gtttcgatga agagggtaat ggcgaaattc tgtccgaacg tcgtcgtgcg     840
gacctggaag cgttcctggg taaccgctac ccggcgtcta ctattccgca gatcgctcgt     900
cgcctgtacg aacataaccg tgttcgcctg ctggtagatg tgaactatac tccggttccg     960
ctacagccgc gcatcagccc gctgaacggt cgtgatctgg atatgtccct gtcttgcctg    1020
cgctctatgt ccccgatcca ccagaaatac atgcaggaca tgggcgttgg cgcgaccctg    1080
gtttgctctc tgatggtgtc tggtcgtctg tggggtctga tcgcttgcca ccactacgaa    1140
ccgcgcttcg ttccgttcca cattcgcgct gctggcgaag cgctggcgga aacttgtgcg    1200
atccgcatcg cgacgctgga gagctttgca cagtctcagt ccaaagaaaa tctctacttc    1260
cagagtgaat tctgtgaacg cgagcagatc cacctggcgg gctccattca gccgcacggt    1320
atcctgctgg ctgtgaaaga gccggacaac gtggtgatcc aggcttctat taacgctgcg    1380
gagttcctga acaccaactc tgttgttggc cgtccgctgc gtgacctggg cggcgatctg    1440
cctttgcaga tcctgccgca cctgaacggc ccgctgcacc tggctccgat gaccctgcgt    1500
tgtaccgtgg gttctccgcc gcgtcgtgtg gactgtacca ttcatcgtcc gtctaacggc    1560
ggcctgatcg tagaactgga accagcaacc aagctcgagg gaggcagccg ggaccacatg    1620 gtgctgcacag agtacgtgaa cgccgccggc atcaca                             1656

<210> SEQ ID NO 3
<211> LENGTH: 1635
<212> TYPE: DNA
<213> ORGANISM: Artificial Sequence
<220> FEATURE:
<223> OTHER INFORMATION: (Nucleic acid sequence of iTEV(+) 3.0)

<400> SEQUENCE: 3
atgtccaaag agaagaact gtttaccggt gttgtgccaa ttttggttga actcgatggt      60
gatgtcaacg gacataagtt ctcagtgaga ggcgaaggag aaggtgacgc caccattgga    120
aaattgactc ttaaattcat ctgtactact ggtaaacttc ctgtaccatg gccgactctc    180
gtaacaacgc ttacgtacgg agttcagtgc ttttcgagat acccagacca tatgaaaaga    240
catgactttt ttaagtcggc tatgcctgaa ggttacgtgc aagaaagaac aatttcgttc    300
aaagatgatg gaaaatataa aactagagca gttgttaaat ttgaaggaga tactttggtt    360
aaccgcattg aactgaaagg aacagatttt aagaagatg gtaatattct tggacacaaa    420
```

```
ctcgaataca attttaatag tcataacgta tacatcactg ctgataagca aaagaacgga      480
attaaagcga atttcacagt acgccataat gtagaagatg gcagtgttca acttgccgac      540
cattaccaac aaaacacccc tattggagac ggtccggtac ttcttcctga taatcactac      600
ctctcaacac aaacagtcct gagcaaagat ccaaatgaaa aaggaggcag cggatccacc      660
actaacattg cgccggctct ggacggtgcg tttcatcgta tcacttcttc atcctccctg      720
atgggcctgt gtgacgaaac cgcgactatt atccgtgaga ttactggcta cgaccgtgtg      780
atggtagtac gtttcgatga agagggtaat ggcgaaattc tgtccgaacg tcgtcgtgcg      840
gacctggaag cgttcctggg taaccgctac ccggcgtcta ctattccgca gatcgctcgt      900
cgcctgtacg aacataaccg tgttcgcctg ctggtagatg tgaactatac tccggttccg      960
ctacagccgc gcatcagccc gctgaacggt cgtgatctgg atatgtccct gtcttgcctg     1020
cgctctatgt ccccgatcca ccagaaatac atgcaggaca tgggcgttgg cgcgaccctg     1080
gtttgctctc tgatggtgtc tggtcgtctg tggggtctga tcgcttgcca ccactacgaa     1140
ccgcgcttcg ttccgttcca cattgcgct gctggcgaag cgctggcgga aacttgtgcg     1200
atccgcatcg cgacgctgga gagcgaaaat ctctacttcc agagtgaatt ctgtgaacgc     1260
gagcagatcc acctggcggg ctccattcag ccgcacggta tcctgctggc tgtgaaagag     1320
ccggacaacg tggtgatcca ggcttctatt aacgctgcgg agttcctgaa caccaactct     1380
gttgttggcc gtccgctgcg tgacctgggc ggcgatctgc ctttgcagat cctgccgcac     1440
ctgaacggcc cgctgcacct ggctccgatg accctgcgtt gtaccgtggg ttctccgccg     1500
cgtcgtgtgg actgtaccat tcatcgtccg tctaacggcg gcctgatcgt agaactggaa     1560
ccagcaacca agctcgaggg aggcagccgg gaccacatgg tgctgcacga gtacgtgaac     1620
gccgccggca tcaca                                                      1635

<210> SEQ ID NO 4
<211> LENGTH: 1638
<212> TYPE: DNA
<213> ORGANISM: Artificial Sequence
<220> FEATURE:
<223> OTHER INFORMATION: (Nucleic acid sequence of iTEV(+) 3.1)

<400> SEQUENCE: 4
atgtccaaag gagaagaact gtttaccggt gttgtgccaa ttttggttga actcgatggt       60
gatgtcaacg gacataagtt ctcagtgaga ggcgaaggag aaggtgacgc caccattgga      120
aaattgactc ttaaattcat ctgtactact ggtaaacttc ctgtaccatg gccgactctc      180
gtaacaacgc ttacgtacgg agttcagtgc ttttcgagat acccagacca tatgaaaaga      240
catgactttt ttaagtcggc tatgcctgaa ggttacgtgc aagaaagaac aatttcgttc      300
aaagatgatg gaaaatataa actagagca gttgttaaat ttgaaggaga actttggtt      360 aaccgcattg aactgaaagg aacagatttt aagaagatg gtaatattct tggacacaaa      420
ctcgaataca attttaatag tcataacgta tacatcactg ctgataagca aaagaacgga      480
attaaagcga atttcacagt acgccataat gtagaagatg gcagtgttca acttgccgac      540
cattaccaac aaaacacccc tattggagac ggtccggtac ttcttcctga taatcactac      600
ctctcaacac aaacagtcct gagcaaagat ccaaatgaaa aaggaggcag cggatccacc      660
actaacattg cgccggctct ggacggtgcg tttcatcgta tcacttcttc atcctccctg      720
atgggcctgt gtgacgaaac cgcgactatt atccgtgaga ttactggcta cgaccgtgtg      780
atggtagtac gtttcgatga agagggtaat ggcgaaattc tgtccgaacg tcgtcgtgcg      840
```

```
gacctggaag cgttcctggg taaccgctac ccggcgtcta ctattccgca gatcgctcgt    900
cgcctgtacg aacataaccg tgttcgcctg ctggtagatg tgaactatac tccggttccg    960
ctacagccgc gcatcagccc gctgaacggt cgtgatctgg atatgtccct gtcttgcctg   1020
cgctctatgt ccccgatcca ccagaaatac atgcaggaca tgggcgttgg cgcgaccctg   1080
gtttgctctc tgatggtgtc tggtcgtctg tggggtctga tcgcttgcca ccactacgaa   1140
ccgcgcttcg ttccgttcca cattcgcgct gctggcgaag cgctggcgga aacttgtgcg   1200
atccgcatcg cgacgctgga gagctttgaa aatctctact tccagagtga attctgtgaa   1260
cgcgagcaga tccacctggc gggctccatt cagccgcacg gtatcctgct ggctgtgaaa   1320
gagccggaca acgtggtgat ccaggcttct attaacgctg cggagttcct gaacaccaac   1380
tctgttgttg ccgtccgct gcgtgacctg ggcggcgatc tgcctttgca gatcctgccg   1440
cacctgaacg ccccgctgca cctggctccg atgaccctgc gttgtaccgt gggttctccg   1500
ccgcgtcgtg tggactgtac cattcatcgt ccgtctaacg gcggcctgat cgtagaactg   1560
gaaccagcaa ccaagctcga gggaggcagc cgggaccaca tggtgctgca cgagtacgtg   1620
aacgccgccg gcatcaca                                                 1638

<210> SEQ ID NO 5
<211> LENGTH: 1641
<212> TYPE: DNA
<213> ORGANISM: Artificial Sequence
<220> FEATURE:
<223> OTHER INFORMATION: (Nucleic acid sequence of iTEV(+) 3.2)

<400> SEQUENCE: 5
atgtccaaag gagaagaact gtttaccggt gttgtgccaa ttttggttga actcgatggt     60
gatgtcaacg gacataagtt ctcagtgaga ggcgaaggag aaggtgacgc caccattgga    120
aaattgactc ttaaattcat ctgtactact ggtaaacttc ctgtaccatg gccgactctc    180
gtaacaacgc ttacgtacgg agttcagtgc ttttcgagat acccagacca tatgaaaaga    240
catgactttt ttaagtcggc tatgcctgaa ggttacgtgc aagaaagaac aatttcgttc    300
aaagatgatg gaaaatataa actagagca gttgttaaat tgaaggaga actttggtt     360 aaccgcattg aactgaaagg aacagatttt aaagaagatg gtaatattct tggacacaaa    420
ctcgaataca atttaatag tcataacgta tacatcactg ctgataagca aaagaacgga    480
attaaagcga atttcacagt acgccataat gtagaagatg gcagtgttca acttgccgac    540
cattaccaac aaaacacccc tattggagac ggtccggtac ttcttcctga taatcactac    600
ctctcaacac aaacagtcct gagcaaagat ccaaatgaaa aaggaggcag cggatccacc    660
actaacattg cgccggctct ggacggtgcg tttcatcgta tcacttcttc atcctccctg    720
atgggcctgt gtgacgaaac cgcgactatt atccgtgaga ttactggcta cgaccgtgtg    780
atggtagtac gtttcgatga agagggtaat ggcgaaattc tgtccgaacg tcgtcgtgcg    840
gacctggaag cgttcctggg taaccgctac ccggcgtcta ctattccgca gatcgctcgt    900
cgcctgtacg aacataaccg tgttcgcctg ctggtagatg tgaactatac tccggttccg    960
ctacagccgc gcatcagccc gctgaacggt cgtgatctgg atatgtccct gtcttgcctg   1020
cgctctatgt ccccgatcca ccagaaatac atgcaggaca tgggcgttgg cgcgaccctg   1080
gtttgctctc tgatggtgtc tggtcgtctg tggggtctga tcgcttgcca ccactacgaa   1140
ccgcgcttcg ttccgttcca cattcgcgct gctggcgaag cgctggcgga aacttgtgcg   1200
```

| | |
|---|---|
| atccgcatcg cgacgctgga gagctttgca gaaaatctct acttccagag tgaattctgt | 1260 |
| gaacgcgagc agatccacct ggcgggctcc attcagccgc acggtatcct gctggctgtg | 1320 |
| aaagagccgg acaacgtggt gatccaggct tctattaacg ctgcggagtt cctgaacacc | 1380 |
| aactctgttg ttggccgtcc gctgcgtgac ctgggcggcg atctgccttt gcagatcctg | 1440 |
| ccgcacctga acgcccgct gcacctggct ccgatgaccc tgcgttgtac cgtgggttct | 1500 |
| ccgccgcgtc gtgtggactg taccattcat cgtccgtcta acggcggcct gatcgtagaa | 1560 |
| ctggaaccag caaccaagct cgagggaggc agccgggacc acatggtgct gcacgagtac | 1620 |
| gtgaacgccg ccggcatcac a | 1641 |

<210> SEQ ID NO 6
<211> LENGTH: 1644
<212> TYPE: DNA
<213> ORGANISM: Artificial Sequence
<220> FEATURE:
<223> OTHER INFORMATION: (Nucleic acid sequence of iTEV(+) 3.3)

<400> SEQUENCE: 6

| | |
|---|---|
| atgtccaaag gagaagaact gtttaccggt gttgtgccaa ttttggttga actcgatggt | 60 |
| gatgtcaacg gacataagtt ctcagtgaga ggcgaaggaa aggtgacgc caccattgga | 120 |
| aaattgactc ttaaattcat ctgtactact ggtaaacttc ctgtaccatg gccgactctc | 180 |
| gtaacaacgc ttacgtacgg agttcagtgc ttttcgagat acccagacca tatgaaaaga | 240 |
| catgactttt ttaagtcggc tatgcctgaa ggttacgtgc aagaaagaac aatttcgttc | 300 |
| aaagatgatg gaaaatataa aactagcaga gttgttaaat ttgaaggaga tacttttggtt | 360 |
| aaccgcattg aactgaaagg aacagatttt aaagaagatg gtaatattct tggacacaaa | 420 |
| ctcgaataca attttaatag tcataacgta tacatcactg ctgataagca aaagaacgga | 480 |
| attaaagcga attttcacagt acgccataat gtagaagatg gcagtgttca acttgccgac | 540 |
| cattaccaac aaaacacccc tattggagac ggtccggtac ttcttcctga taatcactac | 600 |
| ctctcaacac aaacagtcct gagcaaagat ccaaatgaaa aaggaggcag cggatccacc | 660 |
| actaacattg cgccggctct ggacggtgcg tttcatcgta tcacttcttc atcctccctg | 720 |
| atgggcctgt gtgacgaaac cgcgactatt atccgtgaga ttactggcta cgaccgtgtg | 780 |
| atggtagtac gtttcgatga agagggtaat ggcgaaattc tgtccgaacg tcgtcgtgcg | 840 |
| gacctggaag cgttcctggg taaccgctac ccggcgtcta ctattccgca gatcgctcgt | 900 |
| cgcctgtacg aacataaccg tgttcgcctg ctggtagatg tgaactatac tccggttccg | 960 |
| ctacagccgc gcatcagccc gctgaacggt cgtgatctgg atatgtccct gtcttgcctg | 1020 |
| cgctctatgt ccccgatcca ccagaaatac atgcaggaca tgggcgttgg cgcgaccctg | 1080 |
| gtttgctctc tgatggtgtc tggtcgtctg tggggtctga tcgcttgcca ccactacgaa | 1140 |
| ccgcgcttcg ttccgttcca cattcgcgct gctggcgaag cgctggcgga aacttgtgcg | 1200 |
| atccgcatcg cgacgctgga gagctttgca caggaaaatc tctacttcca gagtgaattc | 1260 |
| tgtgaacgcg agcagatcca cctggcgggc tccattcagc cgcacggtat cctgctggct | 1320 |
| gtgaaagagc cggacaacgt ggtgatccag gcttctatta acgctgcgga gttcctgaac | 1380 |
| accaactctg ttgttggccg tccgctgcgt gacctgggcg gcgatctgcc tttgcagatc | 1440 |
| ctgccgcacc tgaacggccc gctgcacctg gctccgatga ccctgcgttg taccgtgggt | 1500 |
| tctccgccgc gtcgtgtgga ctgtaccatt catcgtccgt ctaacggcgg cctgatcgta | 1560 |
| gaactggaac cagcaaccaa gctcgaggga ggcagccggg accacatggt gctgcacgag | 1620 |

| | |
|---|---|
| tacgtgaacg ccgccggcat caca | 1644 |

<210> SEQ ID NO 7
<211> LENGTH: 1647
<212> TYPE: DNA
<213> ORGANISM: Artificial Sequence
<220> FEATURE:
<223> OTHER INFORMATION: (Nucleic acid sequence of iTEV(+) 3.4)

<400> SEQUENCE: 7

| | |
|---|---|
| atgtccaaag gagaagaact gtttaccggt gttgtgccaa ttttggttga actcgatggt | 60 |
| gatgtcaacg gacataagtt ctcagtgaga ggcgaaggag aaggtgacgc caccattgga | 120 |
| aaattgactc ttaaattcat ctgtactact ggtaaacttc ctgtaccatg gccgactctc | 180 |
| gtaacaacgc ttcgtacgg agttcagtgc ttttcgagat acccagacca tatgaaaaga | 240 |
| catgactttt ttaagtcggc tatgcctgaa ggttacgtgc aagaaagaac aatttcgttc | 300 |
| aaagatgatg gaaatataa aactagcaga gttgttaaat ttgaaggaga tactttggtt | 360 |
| aaccgcattg aactgaaagg aacagatttt aaagaagatg gtaatattct tggacacaaa | 420 |
| ctcgaataca attttaatag tcataacgta tacatcactg ctgataagca aaagaacgga | 480 |
| attaaagcga atttcacagt acgccataat gtagaagatg gcagtgttca acttgccgac | 540 |
| cattaccaac aaaacacccc tattggagac ggtccggtac ttcttcctga taatcactac | 600 |
| ctctcaacac aaacagtcct gagcaaagat ccaaatgaaa aaggaggcag cggatccacc | 660 |
| actaacattg cgccggctct ggacggtgcg tttcatcgta tcacttcttc atcctccctg | 720 |
| atgggcctgt gtgacgaaac cgcgactatt atccgtgaga ttactggcta cgaccgtgtg | 780 |
| atggtagtac gtttcgatga agagggtaat ggcgaaattc tgtccgaacg tcgtcgtgcg | 840 |
| gacctggaag cgttcctggg taaccgctac ccggcgtcta ctattccgca gatcgctcgt | 900 |
| cgcctgtacg aacataaccg tgttcgcctg ctggtagatg tgaactatac tccggttccg | 960 |
| ctacagccgc gcatcagccc gctgaacggt cgtgatctgg atatgtccct gtcttgcctg | 1020 |
| cgctctatgt ccccgatcca ccagaaatac atgcaggaca tgggcgttgg cgcgaccctg | 1080 |
| gtttgctctc tgatggtgtc tggtcgtctg tggggtctga tcgcttgcca ccactacgaa | 1140 |
| ccgcgcttcg ttccgttcca cattcgcgct gctggcgaag cgctggcgga aacttgtgcg | 1200 |
| atccgcatcg cgacgctgga gagctttgca cagtctgaaa atctctactt ccagagtgaa | 1260 |
| ttctgtgaac gcgagcagat ccacctggcg ggctccattc agccgcacgg tatcctgctg | 1320 |
| gctgtgaaag agccggacaa cgtggtgatc caggcttcta ttaacgctgc ggagttcctg | 1380 |
| aacaccaact ctgttgttgg ccgtccgctg cgtgacctgg cggcgatct gcctttgcag | 1440 |
| atcctgccgc acctgaacgg cccgctgcac ctggctccga tgaccctgcg ttgtaccgtg | 1500 |
| ggttctccgc cgcgtcgtgt ggactgtacc attcatcgtc cgtctaacgg cggcctgatc | 1560 |
| gtagaactgg aaccagcaac caagctcgag ggaggcagcc gggaccacat ggtgctgcac | 1620 |
| gagtacgtga acgccgccgg catcaca | 1647 |

<210> SEQ ID NO 8
<211> LENGTH: 1650
<212> TYPE: DNA
<213> ORGANISM: Artificial Sequence
<220> FEATURE:
<223> OTHER INFORMATION: (Nucleic acid sequence of iTEV(+) 3.5)

<400> SEQUENCE: 8

```
atgtccaaag gagaagaact gtttaccggt gttgtgccaa ttttggttga actcgatggt    60
gatgtcaacg gacataagtt ctcagtgaga ggcgaaggag aaggtgacgc caccattgga   120
aaattgactc ttaaattcat ctgtactact ggtaaacttc ctgtaccatg gccgactctc   180
gtaacaacgc ttacgtacgg agttcagtgc ttttcgagat acccagacca tatgaaaaga   240
catgactttt ttaagtcggc tatgcctgaa ggttacgtgc aagaaagaac aatttcgttc   300
aaagatgatg gaaaatataa aactagagca gttgttaaat ttgaaggaga tactttggtt   360
aaccgcattg aactgaaagg aacagatttt aaagaagatg gtaatattct tggacacaaa   420
ctcgaataca attttaatag tcataacgta tacatcactg ctgataagca aaagaacgga   480
attaaagcga atttcacagt acgccataat gtagaagatg gcagtgttca acttgccgac   540
cattaccaac aaaacacccc tattggagac ggtccggtac ttcttcctga taatcactac   600
ctctcaacac aaacagtcct gagcaaagat ccaaatgaaa aggaggcag cggatccacc   660 actaacattg cgccggctct ggacggtgcg tttcatcgta tcacttcttc atcctccctg   720
atgggcctgt gtgacgaaac cgcgactatt atccgtgaga ttactggcta cgaccgtgtg   780
atggtagtac gtttcgatga agagggtaat ggcgaaattc tgtccgaacg tcgtcgtgcg   840
gacctggaag cgttcctggg taaccgctac ccggcgtcta ctattccgca gatcgctcgt   900
cgcctgtacg aacataaccg tgttcgcctg ctggtagatg tgaactatac tccggttccg   960
ctacagccgc gcatcagccc gctgaacggt cgtgatctgg atatgtccct gtcttgcctg  1020
cgctctatgt ccccgatcca ccagaaatac atgcaggaca tgggcgttgg cgcgaccctg  1080
gtttgctctc tgatggtgtc tggtcgtctg tggggtctga tcgcttgcca ccactacgaa  1140
ccgcgcttcg ttccgttcca cattcgcgct gctggcgaag cgctggcgga aacttgtgcg  1200
atccgcatcg cgacgctgga gagctttgca cagtctcagg aaaatctcta cttccagagt  1260
gaattctgtg aacgcgagca gatccacctg gcgggctcca ttcagccgca cggtatcctg  1320
ctggctgtga aagagccgga caacgtggtg atccaggctt ctattaacgc tgcggagttc  1380
ctgaacacca actctgttgt tggccgtccg ctgcgtgacc tgggcggcga tctgcctttg  1440
cagatcctgc cgcacctgaa cggcccgctg cacctggctc cgatgaccct gcgttgtacc  1500
gtgggttctc cgccgcgtcg tgtggactgt accattcatc gtccgtctaa cggcggcctg  1560
atcgtagaac tggaaccagc aaccaagctc gagggaggca gccgggacca catggtgctg  1620
cacgagtacg tgaacgccgc cggcatcaca                                    1650

<210> SEQ ID NO 9
<211> LENGTH: 1653
<212> TYPE: DNA
<213> ORGANISM: Artificial Sequence
<220> FEATURE:
<223> OTHER INFORMATION: (Nucleic acid sequence of iTEV(+) 3.6)

<400> SEQUENCE: 9
atgtccaaag gagaagaact gtttaccggt gttgtgccaa ttttggttga actcgatggt    60
gatgtcaacg gacataagtt ctcagtgaga ggcgaaggag aaggtgacgc caccattgga   120
aaattgactc ttaaattcat ctgtactact ggtaaacttc ctgtaccatg gccgactctc   180
gtaacaacgc ttacgtacgg agttcagtgc ttttcgagat acccagacca tatgaaaaga   240
catgactttt ttaagtcggc tatgcctgaa ggttacgtgc aagaaagaac aatttcgttc   300
aaagatgatg gaaaatataa aactagagca gttgttaaat ttgaaggaga tactttggtt   360
aaccgcattg aactgaaagg aacagatttt aaagaagatg gtaatattct tggacacaaa   420
```

```
ctcgaataca attttaatag tcataacgta tacatcactg ctgataagca aaagaacgga    480
attaaagcga atttcacagt acgccataat gtagaagatg gcagtgttca acttgccgac    540
cattaccaac aaaacacccc tattggagac ggtccggtac ttcttcctga taatcactac    600
ctctcaacac aaacagtcct gagcaaagat ccaaatgaaa aaggaggcag cggatccacc    660
actaacattg cgccggctct ggacggtgcg tttcatcgta tcacttcttc atcctccctg    720
atgggcctgt gtgacgaaac cgcgactatt atccgtgaga ttactggcta cgaccgtgtg    780
atggtagtac gtttcgatga agagggtaat ggcgaaattc tgtccgaacg tcgtcgtgcg    840
gacctggaag cgttcctggg taaccgctac ccggcgtcta ctattccgca gatcgctcgt    900
cgcctgtacg aacataaccg tgttcgcctg ctggtagatg tgaactatac tccggttccg    960
ctacagccgc gcatcagccc gctgaacggt cgtgatctgg atatgtccct gtcttgcctg   1020
cgctctatgt ccccgatcca ccagaaatac atgcaggaca tgggcgttgg cgcgaccctg   1080
gtttgctctc tgatggtgtc tggtcgtctg tggggtctga tcgcttgcca ccactacgaa   1140
ccgcgcttcg ttccgttcca cattcgcgct gctggcgaag cgctggcgga aacttgtgcg   1200
atccgcatcg cgacgctgga gagctttgca cagtctcagt ccgaaaatct ctacttccag   1260
agtgaattct gtgaacgcga gcagatccac ctggcgggct ccattcagcc gcacggtatc   1320
ctgctggctg tgaaagagcc ggacaacgtg gtgatccagg cttctattaa cgctgcggag   1380
ttcctgaaca ccaactctgt tgttggccgt ccgctgcgtg acctgggcgg cgatctgcct   1440
ttgcagatcc tgccgcacct gaacggcccg ctgcacctgg ctcgatgac cctgcgttgt   1500 accgtgggtt ctccgccgcg tcgtgtggac tgtaccattc atcgtccgtc taacggcggc   1560
ctgatcgtag aactggaacc agcaaccaag ctcgagggag gcagccggga ccacatggtg   1620
ctgcacgagt acgtgaacgc cgccggcatc aca                                1653
```

<210> SEQ ID NO 10
<211> LENGTH: 1635
<212> TYPE: DNA
<213> ORGANISM: Artificial Sequence
<220> FEATURE:
<223> OTHER INFORMATION: (Nucleic acid sequence of iTEV(+) 6.01)

<400> SEQUENCE: 10

```
atgtccaaag agaagaaact gtttaccggt gttgtgccaa ttttggttga actcgatggt     60
gatgtcaacg gacataagtt ctcagtgaga ggcgaaggag aaggtgacgc caccattgga    120
aaattgactc ttaaattcat ctgtactact ggtaaacttc ctgtaccatg gccgactctc    180
gtaacaacgc ttacgtacgg agttcagtgc ttttcgagat acccagacca tatgaaaaga    240
catgactttt ttaagtcggc tatgcctgaa ggttacgtgc aagaaagaac aatttcgttc    300
aaagatgatg gaaaatataa aactagagca gttgttaaat ttgaaggaga tactttggtt    360
aaccgcattg aactgaaagg aacagatttt aaagaagatg gtaatattct ggacacaaaa    420
ctcgaataca attttaatag tcataacgta tacatcactg ctgataagca aaagaacgga    480
attaaagcga atttcacagt acgccataat gtagaagatg gcagtgttca acttgccgac    540
cattaccaac aaaacacccc tattggagac ggtccggtac ttcttcctga taatcactac    600
ctctcaacac aaacagtcct gagcaaagat ccaaatgaaa aaggaggcag cggatccacc    660
actaacattg cgccggctct ggacggtgcg tttcatcgta tcacttcttc atcctccctg    720
atgggcctgt gtgacgaaac agcgactatt atccgtgaga ttactggcta cgaccgtgtg    780
```

```
atggtagtac gtttcgatga agagggtaat gccgaaattc tgtccgaacg tcgtcgtgcg     840
gacctggaag cgttcctggg taaccgctac ccggcgtcta ctattccgca gatcgctcgt     900
cgcctgtatg aacataaccg tgttcgcctg ctggtagatg tgaactatac tccggttccg     960
ctacagccgc gcatcagccc gctgaacggt cgtgatctgg atatgtccct gtcttgcctg    1020
cgctctatgt ccccgatcca ccagaaatac atgcaggaca tgggcgttgg cgcgaccctg    1080
gttagctctc tgatggtgtc tggtcgtctg tggggtctga tcgcttgcca ccactacgaa    1140
ccgcgcttcg ttccgttcca aattcgcgct gcttgcgaag cgctggcgga aacttgtgcg    1200
aaccgcatcg cgacgctgga gagcgaaaat ctctacttcc agagtgaatt ctgtgaacgc    1260
gagcagatcc acctggcggg ctccattcag ccgcacggta tcctgctggc tgtgaaagag    1320
ccagacaacg tggtgatcca ggcttctatt aacgctgcgg agttcctgaa catcaactct    1380
gttgttggcc gtccgctgcg tgacctgggc ggcgatctgc ctttgcagat cctgccgcac    1440
ctgaacggcc cgctgcacct ggctccggtg accctgcgtt gtaccgtggg ttctccgccg    1500
cgtcgtgtgg actgtaccat tcatcgtccg tctaacggcg gcctgatcgt agaactggaa    1560
ccagcaacca agctcgaggg aggcagccgg gaccacatgg tgctgcacga gtacgtgaac    1620
gccgccggca tcaca                                                     1635
```

<210> SEQ ID NO 11
<211> LENGTH: 1635
<212> TYPE: DNA
<213> ORGANISM: Artificial Sequence
<220> FEATURE:
<223> OTHER INFORMATION: (Nucleic acid sequence of iTEV(+) 6.03)

<400> SEQUENCE: 11

```
atgtccaaag gagaagaact gtttaccggt gttgtgccaa ttttggttga actcgatggt      60
gatgtcaacg gacataagtt ctcagtgaga ggcgaaggag aaggtgacgc caccattgga     120
aaattgactc ttaaattcat ctgtactact ggtaaacttc ctgtaccatg gccgactctc     180
gtaacaacgc ttacgtacgg agttcagtgc ttttcgagat acccagacca tatgaaaaga     240
catgactttt ttaagtcggc tatgcctgaa ggttacgtgc aagaaagaac aatttcgttc     300
aaagatgatg gaaaatataa aactagagca gttgttaaat ttgaaggaga tactttggtt     360
aaccgcattg aactgaaagg aacagatttt aagaagatgg taatattctt ggacacaaaa     420
ctcgaataca attttaatag tcataacgta tacatcactg ctgataagca aagaacggga     480
attaaagcga atttcacagt acgccataat gtagaagatg gcagtgttca acttgccgac     540
cattaccaac aaaacacccc tattggagac ggtccggtac ttcttcctga taatcactac     600
ctctcaacac aaacagtcct gagcaaagat ccaaatgaaa aaggaggcag cggatccacc     660
actaacattg cgccggctct ggacggtgcg tttcatcgta tcacttcttc atcctccctg     720
atgggcctgt gtgacgaaac cgcgactatt atccgtgaga ttactggcta cgaccgtgtg     780
atggtagtac gtttcgatga agagggtaat gccgaaattc tgtccgaacg tcgtcgtgcg     840
gacctggaag cgttcctggg taaccgctac ccggcgtcta ctattccgca gatcgctcgt     900
cgcctgtacg aacataaccg tgttcgcctg ctggtagatg tgaactatac tccggttccg     960
ctacagccgc gcatcagccc gctgaacggt cgtgatctgg atatgtccct gtcttgcctg    1020
cgctctatgt ccccggtcca ccagaaatac atgcaggaca tgggcgttgg cgcgaccctg    1080
gtttgctctc tgatggtgtc tggtcgtttg tggggtctga tcgcttgcca ccactacgaa    1140
ccgcgcttcg ttccgttcca cattcgcgct gctggcgaag cgctggcgga aacttgtgcg    1200
```

```
aaccgcatcg cgacgctgga gagcgaaaat ctctacttcc agagtgaatt ctgtgaacgc   1260
gagcagatcc acctggcggg ctccattcag ccgcacggta tcctgctggc tgtgaaagag   1320
ccagacaacg tggtgatcca ggcttctatc aacgctgcgg agttcctgaa caccaactct   1380
gttgttggcc gtccgctgcg tgacctgggc ggcgatctgc ctttgcagat cctgccgcac   1440
ctgaacggcc cgctgcacct ggctccggtg accctgcgtt gtaccgtggg ttctccgccg   1500
cgccgtgtgg actgtaccat tcaccgtccg tctaacggcg gcctgatcgt agaactggaa   1560
ccagcaacca agctcgaggg aggcagccgg gaccacatgg tgctgcacga gtacgtgaac   1620
gccgccggca tcaca                                                    1635
```

<210> SEQ ID NO 12
<211> LENGTH: 1635
<212> TYPE: DNA
<213> ORGANISM: Artificial Sequence
<220> FEATURE:
<223> OTHER INFORMATION: (Nucleic acid sequence of iTEV(+) 6.04)

<400> SEQUENCE: 12

```
atgtccaaag gagaagaact gtttaccggt gttgtgccaa ttttggttga actcgatggt     60
gatgtcaacg gacataagtt ctcagtgaga ggcgaaggag aaggtgacgc caccattgga    120
aaattgactc ttaaattcat ctgtactact ggtaaacttc ctgtaccatg gccgactctc    180
gtaacaacgc ttacgtacgg agttcagtgc ttttcgagat acccagacca tatgaaaaga    240
catgactttt ttaagtcggc tatgcctgaa ggttacgtgc aagaaagaac aatttcgttc    300
aaagatgatg gaaaatataa actagagcag gttgttaaat ttgaaggaga cactttggtt    360
aaccgcattg aactgaaagg aacagatttt aagaagatgg taatattctg gacacaaaa    420 ctcgaataca actttaatag tcataacgta tacatcactg ctgataagca aaagaacgga    480
attaaagcga attcacagt acgccataat gtagaagatg gcagtgttca acttgccgac    540
cattaccaac aaaacacccc tattggagac ggtccggtac ttcttcctga taatcactac    600
ctctcaacac aaacagtcct gagcaaagat ccaaatgaaa aaggaggcag cggatccacc    660
actaacattg cgccggctct ggacggtgcg tttcatcgta tcacttcttc atcctccctg    720
atgggcctgt gtgacgaaac agcgactatt atccgtgaga ttactggcta cgaccgtgtg    780
atggtagtac gtttcgatga gagggtaat gccgaaattc tgtccgaacg tcgtcgtgcg    840
gacctggaag cgttcctggg taaccgctac ccggcgtcta ctattccgca gatcgctcgt    900
cgcctgtacg aacataaccg tgttcgcctg ctggtagatg tgaactatac tccggttccg    960
ctacagccgc gcatcagccc gctgaacggt cgtgatctgg atatgtccct gtcttgcctg   1020
cgctctatgt ccccgatcca ccagaaatac atgcaggaca tgggcgttgg cgcgaccctg   1080
gtttgctctc tgatggtgtc tggtcgtctg tggggtctga tcgcttgcca ccactacgaa   1140
ccgcgcttcg ttccgttcca cattcgcgct gctggcgaag cgctggcgga aacttgtgcg   1200
aaccgcatcg cgacgctgga gagcgaaaat ctctacttcc agagtgaatt ctgtgaacgc   1260
gagcagatcc acctggcggg ctccattcag ccgcacggta tcctgctggc tgtgaaagag   1320
ccagacaacg tggtgatcca ggcttctatt aacgctgcgg agttcctgaa caccaactct   1380
gttgttggcc gtccgctgcg tgacctgggc ggcgatctgc ctttgcagat cctgccgcac   1440
ctgaacggcc cgctgcacct ggctccggtg accctgcgtt gtaccgtggg ttctccgccg   1500
cgtcgtgtgg actgtaccat tcatcgtccg tctaacggcg gcctgatcgt agaactggaa   1560
```

```
ccagcaacca agctcgaggg aggcagccgg gaccacatgg tgctgcacga gtacgtgaac      1620
gccgccggca tcaca                                                       1635

<210> SEQ ID NO 13
<211> LENGTH: 1635
<212> TYPE: DNA
<213> ORGANISM: Artificial Sequence
<220> FEATURE:
<223> OTHER INFORMATION: (Nucleic acid sequence of iTEV(+) 6.05)

<400> SEQUENCE: 13
atgtccaaag gagaagaact gtttaccggt gttgtgccaa ttttggttga actcgatggt        60
gatgtcaacg gacataagtt ctcagtgaga ggcgaaggag aaggtgacgc caccattgga       120
aaattgactc ttaaattcat ctgtactact ggtaaacttc ctgtaccatg gccgactctc       180
gtaacaacgc ttacgtacgg agttcagtgc ttttcgagat acccagacca tatgaaaaga       240
catgactttt ttaagtcggc tatgcctgaa ggttacgtgc aagaaagaac aatttcgttc       300
aaagatgatg gaaaatataa aactagagca gttgttaaat ttgaaggaga tactttggtt       360
aaccgcattg aactgaaagg aacagatttt aaagaagatg gtaatattct tggacacaaa       420
ctcgaataca tttttaatag tcataacgta tacatcactg ctgataagca aaagaacgga       480
attaaagcga atttcacagt acgccataat gtagaagatg gcagtgttca acttgccgac       540 cattccaac aaaacacccc tattggagac ggtccggtac ttcttcctga taatcactac       600
ctctcaacac aaacagtcct gagcaaagat ccaaatgaaa aggaggcag cggatccacc        660 actaacattg cgccggctct ggacggtgcg tttcatcgta tcacttcttc atcctccctg       720
atgggcctgt gtgacgaaac cgcgactatt atccgtgaga ttactggcta cgaccgtgtg       780
atggtagtac gtttcgatga agagggtaat gccgaaattc tgtccgaacg tcgtcgtgcg       840
gacctggaag cgttcctggg taaccgctac ccggcgtcta ctattccgca gatcgctcgt       900
cgcctgtacg aacataaccg tgttcgcctg ctggtagatg tgaactatac tccggttccg       960
ctacagccgc gcatcagccc gctgaacggt cgtgatctgg atatgtccct gtcttgcctg      1020
cgctctatgt ccccgatcca ccagaaatac atgcaggaca tgggcgttgg cgcgaccctg      1080
gtttgctctc tgatggtgtc tggtcgtctg tggggtctga tcgcttgcca ccactacgaa      1140
ccgcgcttcg ttccgttcca cattcgcgct gctgtcgatg cgctggcgga aacttgtgcg      1200
atccgcatcg cgacgctgga gagcgaaaat ctctacttcc agagtgaatt ctgtgaacgc      1260
gagcagatcc acctggcggg ctccattcag ccgcacggta tcctgctggc tgtgaaagag      1320
ccagacaacg tggtgatcca agcttctatt aacgctgcgg agttcctgaa caccaactct      1380
gttgttggcc gtccgctgcg tgacctgggc ggcgatctgc ttttgcagat cctgccgcac      1440
ctgaacggcc cgctgcacct ggctccggtg accctgcgtt gtaccgtggg ttctccgccg      1500
cgtcgtgtgg actgtaccat tcatcgtccg tctaacggcg gcctgatcgt agaactggaa      1560
ccagcaacca agctcgaggg aggcagccgg gaccacatgg tgctgcacga gtacgtgaac      1620
gccgccggca tcaca                                                       1635

<210> SEQ ID NO 14
<211> LENGTH: 1635
<212> TYPE: DNA
<213> ORGANISM: Artificial Sequence
<220> FEATURE:
<223> OTHER INFORMATION: (Nucleic acid sequence of iTEV(+) 6.13)

<400> SEQUENCE: 14
```

```
atgtccaaag gagaagaact gtttaccggt gttgtgccaa ttttggttga actcgatggt    60
gatgtcaacg gacataagtt ctcagtgaga ggcgaaggag aaggtgacgc caccattgga   120
aaattgactc ttaaattcat ctgtactact ggtaaacttc ctgtaccatg gccgactctc   180
gtaacaacgc ttacgtacgg agttcagtgc ttttcgagat acccagacca tatgaaaaga   240
catgactttt ttaagtcggc tatgcctgaa ggttacgtgc aagaaagaac aatttcgttc   300
aaagatgatg gaaaatataa aactagagca gttgttaaat ttgaaggaga tactttggtt   360
aaccgcattg aactgaaagg aacagatttt aaagaagatg gtaatattct tggacacaaa   420
ctcgaataca attttaatag tcataacgta tacatcactg ctgataagca aaagaacgga   480
attaaagcga atttcacagt acgccataat gtagaagatg gcagtgttca acttgccgac   540
cattaccaac aaaacacccc tattggagac ggtccggtac ttcttcctga taatcactac   600
ctctcaacac aaacagtcct gagcaaagat ccaaatgaaa aaggaggcag cggatccacc   660
actaacattg cgccggctct ggacggtgcg tttcatcgta tcacttcttc atcctccctg   720
atgggcctgt gtgacgaaac cgcgactatt atccgtgaga ttactggcta cgaccgtgtg   780
atggtagtac gtttcgatga agagggtaat gccgaaattc tgtccgaacg tcgtcgtgcg   840
gacctggaag cgttcctggg taaccgctac ccggcgtcta ctattccgca gatcgctcgt   900
cgcctgtacg aacataaccg tgttcgcctg ctggtagatg tgaactatac tccggttccg   960
ctacagccgc gcatcagccc gctgaacggt cgtgatctgg atatgtccct gtcttgcctg  1020
cgctctatgt ccccgaacca ccagaaatac atgcaggaca tgggcgttgg cgcgaccctg  1080
gtttgctctc tgatggtgtc tggtcgtttg tggggtctga tcgcttgcca ccactacgaa  1140
ccgcgcttcg ttccgttcca cattcgcgct gctggcgaag cgctggcgga aacttgtgcg  1200
gcacgcatcg cgacgctgga gagcgaaaat ctctacttcc agagtgaatt ctgtgaacgc  1260
gagcagatcc acctggcggg ctccattcag ccgcacggta tcctgctggc tgtgaaagag  1320
ccagacaacg tggtgatcca ggcttctatc aacgctgcgg agttcctgaa caccaactct  1380
gttgttggcc gtccgctgcg tgacctgggc ggcgatctgc ctttgcagat cctgccgcac  1440
ctgaacggcc cgctgcacct ggctccggtg acctgcgtt gtaccgtggg ttctccgccg  1500
cgccgtgtgg actgtaccat tcaccgtccg tctaacggcg gcctgatcgt agaactggaa  1560
ccagcaacca agctcgaggg aggcagccgg gaccacatgt gctgcacga gtacgtgaac  1620
gccgccggca tcaca                                                    1635
```

<210> SEQ ID NO 15  
<211> LENGTH: 1179  
<212> TYPE: DNA  
<213> ORGANISM: Artificial Sequence  
<220> FEATURE:  
<223> OTHER INFORMATION: (Nucleic acid sequence of iTEV(+) 5.1)

<400> SEQUENCE: 15

```
atgggcggca gcaaggtgtc tgcacttaaa gaaaaggttt ccgcactcaa ggagaaagtt    60
tcagctttga agagaaaggt cagtgccctt aaggaaaaag tgagcgcgct gaaagaagga   120
ggcagcggat ccaccactaa cattgcgccg gctctggacg gtgcgtttca tcgtatcact   180
tcttcatcct ccctgatggg cctgtgtgac gaaaccgcga ctattatccg tgagattact   240
ggctacgacc gtgtgatggt agtacgtttc gatgaagagg gtaatggcga aattctgtcc   300
gaacgtcgtc gtgcggacct ggaagcgttc ctgggtaacc gctacccggc gtctactatt   360
```

| | |
|---|---|
| ccgcagatcg ctcgtcgcct gtacgaacat aaccgtgttc gcctgctggt agatgtgaac | 420 |
| tatactccgg ttccgctaca gccgcgcatc agcccgctga acggtcgtga tctggatatg | 480 |
| tccctgtctt gcctgcgctc tatgtccccg atccaccaga aatacatgca ggacatgggc | 540 |
| gttggcgcga ccctggtttg ctctctgatg gtgtctggtc gtctgtgggg tctgatcgct | 600 |
| tgccaccact acgaaccgcg cttcgttccg ttccacattc gcgctgctgg cgaagcgctg | 660 |
| gcggaaactt gtgcgatccg catcgcgacg ctggagagcg aaaatctcta cttccagagt | 720 |
| gaattctgtg aacgcgagca gatccacctg gcgggctcca ttcagccgca cggtatcctg | 780 |
| ctggctgtga agagccgga caacgtggtg atccaggctt ctattaacgc tgcggagttc | 840 |
| ctgaacacca actctgttgt tggccgtccg ctgcgtgacc tgggcggcga tctgcctttg | 900 |
| cagatcctgc cgcacctgaa cggcccgctg cacctggctc cgatgaccct gcgttgtacc | 960 |
| gtgggttctc cgccgcgtcg tgtggactgt accattcatc gtccgtctaa cggcggcctg | 1020 |
| atcgtagaac tggaaccagc aaccaagctc gagggtggcg ggtccggagg cagcgaagtg | 1080 |
| agcgcgctgg aaaaagaggt ctccgctctt gagaaggaag tttctgcctt ggagaaagag | 1140 |
| gtgagcgccc tggagaagga agtctctgcg cttgaaaaa | 1179 |

<210> SEQ ID NO 16
<211> LENGTH: 1179
<212> TYPE: DNA
<213> ORGANISM: Artificial Sequence
<220> FEATURE:
<223> OTHER INFORMATION: (Nucleic acid sequence of iTEV(+) 6.031)

<400> SEQUENCE: 16

| | |
|---|---|
| atgggcggca gcaaggtgtc tgcacttaaa gaaaaggttt ccgcactcaa ggagaaagtt | 60 |
| tcagctttga agagaaggt cagtgccctt aaggaaaaag tgagcgcgct gaaagaagga | 120 |
| ggcagcggat ccaccactaa cattgcgccg gctctggacg tgcgtttca tcgtatcact | 180 |
| tcttcatcct ccctgatggg cctgtgtgac gaaaccgcga ctattatccg tgagattact | 240 |
| ggctacgacc gtgtgatggt agtacgtttc gatgaagagg gtaatgccga aattctgtcc | 300 |
| gaacgtcgtc gtgcggacct ggaagcgttc ctgggtaacc gctaccggc gtctactatt | 360 |
| ccgcagatcg ctcgtcgcct gtacgaacat aaccgtgttc gcctgctggt agatgtgaac | 420 |
| tatactccgg ttccgctaca gccgcgcatc agcccgctga acggtcgtga tctggatatg | 480 |
| tccctgtctt gcctgcgctc tatgtccccg gtccaccaga aatacatgca ggacatgggc | 540 |
| gttggcgcga ccctggtttg ctctctgatg gtgtctggtc gtttgtgggg tctgatcgct | 600 |
| tgccaccact acgaaccgcg cttcgttccg ttccacattc gcgctgctgg cgaagcgctg | 660 |
| gcggaaactt gtgcgaaccg catcgcgacg ctggagagcg aaaatctcta cttccagagt | 720 |
| gaattctgtg aacgcgagca gatccacctg gcgggctcca ttcagccgca cggtatcctg | 780 |
| ctggctgtga agagccaga caacgtggtg atccaggctt ctatcaacgc tgcggagttc | 840 |
| ctgaacacca actctgttgt tggccgtccg ctgcgtgacc tgggcggcga tctgcctttg | 900 |
| cagatcctgc cgcacctgaa cggcccgctg cacctggctc cggtgaccct gcgttgtacc | 960 |
| gtgggttctc cgccgcgccg tgtggactgt accattcacc gtccgtctaa cggcggcctg | 1020 |
| atcgtagaac tggaaccagc aaccaagctc gagggtggcg ggtccggagg cagcgaagtg | 1080 |
| agcgcgctgg aaaaagaggt ctccgctctt gagaaggaag tttctgcctt ggagaaagag | 1140 |
| gtgagcgccc tggagaagga agtctctgcg cttgaaaaa | 1179 |

<210> SEQ ID NO 17
<211> LENGTH: 1632
<212> TYPE: DNA
<213> ORGANISM: Artificial Sequence
<220> FEATURE:
<223> OTHER INFORMATION: (Nucleic acid sequence of iCAS3(+) 3.0)

<400> SEQUENCE: 17

```
atgtccaaag gagaagaact gtttaccggt gttgtgccaa ttttggttga actcgatggt      60
gatgtcaacg gacataagtt ctcagtgaga ggcgaaggag aaggtgacgc caccattgga     120
aaattgactc ttaaattcat ctgtactact ggtaaacttc ctgtaccatg gccgactctc     180
gtaacaacgc ttacgtacgg agttcagtgc ttttcgagat acccagacca tatgaaaaga     240
catgactttt ttaagtcggc tatgcctgaa ggttacgtgc aagaaagaac aatttcgttc     300
aaagatgatg gaaaatataa aactagagca gttgttaaat ttgaaggaga tactttggtt     360
aaccgcattg aactgaaagg aacagatttt aaagaagatg gtaatattct tggacacaaa     420
ctcgaataca attttaatag tcataacgta tacatcactg ctgataagca aaagaacgga     480
attaaagcga atttcacagt acgccataat gtagaagatg gcagtgttca acttgccgac     540
cattaccaac aaaacacccc tattggagac ggtccggtac ttcttcctga taatcactac     600
ctctcaacac aaacagtcct gagcaaagat ccaaatgaaa aggaggcag cggatccacc      660
actaacattg cgccggctct ggacggtgcg tttcatcgta tcacttcttc atcctccctg     720
atgggcctgt gtgacgaaac cgcgactatt atccgtgaga ttactggcta cgaccgtgtg     780
atggtagtac gtttcgatga agagggtaat ggcgaaattc tgtccgaacg tcgtcgtgcg     840
gacctggaag cgttcctggg taaccgctac ccggcgtcta ctattccgca gatcgctcgt     900
cgcctgtacg aacataaccg tgttcgcctg ctggtagatg tgaactatac tccggttccg     960
ctacagccgc gcatcagccc gctgaacggt cgtgatctgg atatgtccct gtcttgcctg    1020
cgctctatgt ccccgatcca ccagaaatac atgcaggaca tgggcgttgg cgcgaccctg    1080
gtttgctctc tgatggtgtc tggtcgtctg tggggtctga tcgcttgcca ccactacgaa    1140
ccgcgcttcg ttccgttcca cattcgcgct gctggcgaag cgctggcgga acttgtgcg     1200
atccgcatcg cgacgctgga gagcggtgat gaagttgatg gtgaattctg tgaacgcgag    1260
cagatccacc tggcgggctc cattcagccg caccggtatcc tgctggctgt gaaagagccg    1320
gacaacgtgg tgatccaggc ttctattaac gctgcggagt cctgaacac caactctgtt    1380
gttggccgtc cgctgcgtga cctgggcggc gatctgcctt tgcagatcct gccgcacctg    1440
aacgcccgc tgcacctggc tccgatgacc ctgcgttgta ccgtgggttc tccgcgcgt     1500
cgtgtggact gtaccattca tcgtccgtct aacggcggcc tgatcgtaga actggaacca    1560
gcaaccaagc tcgagggagg cagccgggac cacatggtgc tgcacgagta cgtgaacgcc    1620
gccggcatca ca                                                         1632
```

<210> SEQ ID NO 18
<211> LENGTH: 1632
<212> TYPE: DNA
<213> ORGANISM: Artificial Sequence
<220> FEATURE:
<223> OTHER INFORMATION: (Nucleic acid sequence of iCAS3(+) 6.03)

<400> SEQUENCE: 18

```
atgtccaaag gagaagaact gtttaccggt gttgtgccaa ttttggttga actcgatggt      60
gatgtcaacg gacataagtt ctcagtgaga ggcgaaggag aaggtgacgc caccattgga     120
```

```
aaattgactc ttaaattcat ctgtactact ggtaaacttc ctgtaccatg gccgactctc    180
gtaacaacgc ttacgtacgg agttcagtgc ttttcgagat acccagacca tatgaaaaga    240
catgactttt ttaagtcggc tatgcctgaa ggttacgtgc aagaaagaac aatttcgttc    300
aaagatgatg gaaatataa aactagagca gttgttaaat ttgaaggaga tactttggtt     360
aaccgcattg aactgaaagg aacagatttt aaagaagatg gtaatattct tggacacaaa    420
ctcgaataca attttaatag tcataacgta tacatcactg ctgataagca aaagaacgga    480
attaaagcga atttcacagt acgccataat gtagaagatg gcagtgttca acttgccgac    540
cattaccaac aaaacacccc tattggagac ggtccggtac ttcttcctga taatcactac    600
ctctcaacac aaacagtcct gagcaaagat ccaaatgaaa aaggaggcag cggatccacc    660
actaacattg cgccggctct ggacggtgcg tttcatcgta tcacttcttc atcctccctg    720
atgggcctgt gtgacgaaac cgcgactatt atccgtgaga ttactggcta cgaccgtgtg    780
atggtagtac gtttcgatga agagggtaat gccgaaattc tgtccgaacg tcgtcgtgcg    840
gacctggaag cgttcctggg taaccgctac ccggcgtcta ctattccgca gatcgctcgt    900
cgcctgtacg aacataaccg tgttcgcctg ctggtagatg tgaactatac tccggttccg    960
ctacagccgc gcatcagccc gctgaacggt cgtgatctgg atatgtccct gtcttgcctg   1020
cgctctatgt ccccggtcca ccagaaatac atgcaggaca tgggcgttgg cgcgaccctg   1080
gtttgctctc tgatggtgtc tggtcgtttg tggggtctga tcgcttgcca ccactacgaa   1140
ccgcgcttcg ttccgttcca cattcgcgct gctggcgaag cgctggcgga aacttgtgcg   1200
aaccgcatcg cgacgctgga gagcggtgat gaagttgatg gtgaattctg tgaacgcgag   1260
cagatccacc tggcgggctc cattcagccg cacggtatcc tgctggctgt gaaagagcca   1320
gacaacgtgg tgatccaggc ttctatcaac gctgcggagt cctgaacac caactctgtt   1380 gttggccgtc cgctgcgtga cctgggcggc gatctgcctt tgcagatcct gccgcacctg   1440 aacgcccgc tgcacctggc tccggtgacc ctgcgttgta ccgtgggttc tccgccgcgc   1500
cgtgtggact gtaccattca ccgtccgtct aacggcggcc tgatcgtaga actggaacca   1560
gcaaccaagc tcgagggagg cagccgggac cacatggtgc tgcacgagta cgtgaacgcc   1620
gccggcatca ca                                                        1632
```

<210> SEQ ID NO 19
<211> LENGTH: 1176
<212> TYPE: DNA
<213> ORGANISM: Artificial Sequence
<220> FEATURE:
<223> OTHER INFORMATION: (Nucleic acid sequence of iCAS3(+) 6.031)

<400> SEQUENCE: 19

```
atgggcggca gcaaggtgtc tgcacttaaa gaaaaggttt ccgcactcaa ggagaaagtt     60
tcagctttga aagagaaggt cagtgcccct aaggaaaaag tgagcgcgct gaaagaagga    120
ggcagcggat ccaccactaa cattgcgccg gctctggacg gtgcgtttca tcgtatcact    180
tcttcatcct ccctgatggg cctgtgtgac gaaaccgcga ctattatccg tgagattact    240
ggctacgacc gtgtgatggt agtacgtttc gatgaagagg gtaatgccga aattctgtcc    300
gaacgtcgtc gtgcggacct ggaagcgttc ctgggtaacc gctacccggc gtctactatt    360
ccgcagatcg ctcgtcgcct gtacgaacat aaccgtgttc gcctgctggt agatgtgaac    420
tatactccgg ttccgctaca gccgcgcatc agccgctga acggtcgtga tctggatatg    480
tccctgtctt gcctgcgctc tatgtccccg gtccaccaga aatacatgca ggacatgggc    540
```

| | |
|---|---|
| gttggcgcga cctggtttg ctctctgatg gtgtctggtc gtttgtgggg tctgatcgct | 600 |
| tgccaccact acgaaccgcg cttcgttccg ttccacattc gcgctgctgg cgaagcgctg | 660 |
| gcggaaactt gtgcgaaccg catcgcgacg ctggagagcg tgatgaagt tgatggtgaa | 720 |
| ttctgtgaac gcgagcagat ccacctggcg ggctccattc agccgcacgg tatcctgctg | 780 |
| gctgtgaaag agccagacaa cgtggtgatc caggcttcta tcaacgctgc ggagttcctg | 840 |
| aacaccaact ctgttgttgg ccgtccgctg cgtgacctgg cggcgatct gcctttgcag | 900 |
| atcctgccgc acctgaacgg cccgctgcac ctggctccgg tgaccctgcg ttgtaccgtg | 960 |
| ggttctccgc cgcgccgtgt ggactgtacc attcaccgtc cgtctaacgg cggcctgatc | 1020 |
| gtagaactgg aaccagcaac caagctcgag ggtggcgggt ccggaggcag cgaagtgagc | 1080 |
| gcgctggaaa agaggtctc cgctcttgag aaggaagttt ctgccttgga aaagaggtg | 1140 |
| agcgccctgg agaaggaagt ctctgcgctt gaaaaa | 1176 |

<210> SEQ ID NO 20
<211> LENGTH: 1641
<212> TYPE: DNA
<213> ORGANISM: Artificial Sequence
<220> FEATURE:
<223> OTHER INFORMATION: (Nucleic acid sequence of iNS3(+) 3.1)

<400> SEQUENCE: 20

| | |
|---|---|
| atgtccaaag gagaagaact gtttaccggt gttgtgccaa ttttggttga actcgatggt | 60 |
| gatgtcaacg gacataagtt ctcagtgaga ggcgaaggag aaggtgacgc caccattgga | 120 |
| aaattgactc ttaaattcat ctgtactact ggtaaacttc ctgtaccatg gccgactctc | 180 |
| gtaacaacgc ttacgtacgg agttcagtgc ttttcgagat acccagacca tatgaaaaga | 240 |
| catgactttt ttaagtcggc tatgcctgaa ggttacgtgc aagaaagaac aatttcgttc | 300 |
| aaagatgatg gaaatataa aactagagca gttgttaaat ttgaaggaga tactttggtt | 360 |
| aaccgcattg aactgaaagg aacagatttt aagaagatg gtaatattct tggacacaaa | 420 |
| ctcgaataca tttttaatag tcataacgta tacatcactg ctgataagca aaagaacgga | 480 |
| attaaagcga atttcacagt acgccataat gtagaagatg gcagtgttca acttgccgac | 540 |
| cattaccaac aaaacacccc tattggagac ggtccggtac ttcttcctga taatcactac | 600 |
| ctctcaacac aaacagtcct gagcaaagat ccaaatgaaa aaggaggcag cggatccacc | 660 |
| actaacattg cgccggctct ggacggtgcg tttcatcgta tcacttcttc atcctccctg | 720 |
| atgggcctgt gtgacgaaac cgcgactatt atccgtgaga ttactggcta cgaccgtgtg | 780 |
| atggtagtac gtttcgatga agagggtaat ggcgaaattc tgtccgaacg tcgtcgtgcg | 840 |
| gacctggaag cgttcctggg taaccgctac ccggcgtcta ctattccgca gatcgctcgt | 900 |
| cgcctgtacg aacataaccg tgttcgcctg ctggtagatg tgaactatac tccggttccg | 960 |
| ctacagccgc gcatcagccc gctgaacggt cgtgatctgg atatgtccct gtcttgcctg | 1020 |
| cgctctatgt ccccgatcca ccagaaatac atgcaggaca tgggcgttgg cgcgaccctg | 1080 |
| gtttgctctc tgatggtgtc tggtcgtctg tgggtctga tcgcttgcca ccactacgaa | 1140 |
| ccgcgcttcg ttccgttcca cattcgcgct gctggcgaag cgctggcgga aacttgtgcg | 1200 |
| atccgcatcg cgacgctgga gagcgaggac gtggtgtgct gctcaatgag cgaattctgt | 1260 |
| gaacgcgagc agatccacct ggcgggctcc attcagccgc acggtatcct gctggctgtg | 1320 |
| aaagagccgg acaacgtggt gatccaggct tctattaacg ctgcggagtt cctgaacacc | 1380 |

| aactctgttg ttggccgtcc gctgcgtgac ctgggcggcg atctgccttt gcagatcctg | 1440 |
| ccgcacctga acggcccgct gcacctggct ccgatgaccc tgcgttgtac cgtgggttct | 1500 |
| ccgccgcgtc gtgtggactg taccattcat cgtccgtcta acggcggcct gatcgtagaa | 1560 |
| ctggaaccag caaccaagct cgagggaggc agccgggacc acatggtgct gcacgagtac | 1620 |
| gtgaacgccg ccggcatcac a | 1641 |

<210> SEQ ID NO 21
<211> LENGTH: 1638
<212> TYPE: DNA
<213> ORGANISM: Artificial Sequence
<220> FEATURE:
<223> OTHER INFORMATION: (Nucleic acid sequence of iNS3(+) 3.2)

<400> SEQUENCE: 21

| atgtccaaag gagaagaact gtttaccggt gttgtgccaa ttttggttga actcgatggt | 60 |
| gatgtcaacg gacataagtt ctcagtgaga ggcgaaggag aaggtgacgc caccattgga | 120 |
| aaattgactc ttaaattcat ctgtactact ggtaaacttc ctgtaccatg gccgactctc | 180 |
| gtaacaacgc ttacgtacgg agttcagtgc ttttcgagat acccagacca tatgaaaaga | 240 |
| catgactttt ttagtcggc tatgcctgaa ggttacgtgc aagaaagaac aatttcgttc | 300 |
| aaagatgatg gaaatataa actagagca gttgttaaat ttgaaggaga cttttggtt | 360 |
| aaccgcattg aactgaaagg aacagatttt aagaagatg gtaatattct tggacacaaa | 420 |
| ctcgaataca attttaatag tcataacgta tacatcactg ctgataagca aagaacgga | 480 |
| attaaagcga atttcacagt acgccataat gtagaagatg gcagtgttca acttgccgac | 540 |
| cattaccaac aaaacacccc tattggagac ggtccggtac ttcttcctga taatcactac | 600 |
| ctctcaacac aaacagtcct gagcaaagat ccaaatgaaa aaggaggcag cggatccacc | 660 |
| actaacattg cgccggctct ggacggtgcg tttcatcgta tcacttcttc atcctccctg | 720 |
| atgggcctgt gtgacgaaac cgcgactatt atccgtgaga ttactggcta cgaccgtgtg | 780 |
| atggtagtac gtttcgatga agagggtaat ggcgaaattc tgtccgaacg tcgtcgtgcg | 840 |
| gacctggaag cgttcctggg taaccgctac cggcgtccta ctattccgca gatcgctcgt | 900 |
| cgcctgtacg aacataaccg tgttcgcctg ctggtagatg tgaactatac tccggttccg | 960 |
| ctacagccgc gcatcagccc gctgaacggt cgtgatctgg atatgtccct gtcttgcctg | 1020 |
| cgctctatgt ccccgatcca ccagaaatac atgcaggaca tgggcgttgg cgcgaccctg | 1080 |
| gtttgctctc tgatggtgtc tggtcgtctg tggggtctga tcgcttgcca ccactacgaa | 1140 |
| ccgcgcttcg ttccgttcca cattcgcgct gctggcgaag cgctggcgga acttgtgcg | 1200 |
| atccgcatcg cgacgctgga gagcgaggac gtggtgtgct gctcaatgga attctgtgaa | 1260 |
| cgcgagcaga tccacctggc gggctccatt cagccgcacg gtatcctgct ggctgtgaaa | 1320 |
| gagccggaca acgtggtgat ccaggcttct attaacgctg cggagttcct gaacaccaac | 1380 |
| tctgttgttg ccgtccgct gcgtgacctg ggcggcgatc tgccttttgca gatcctgccg | 1440 |
| cacctgaacg gcccgctgca cctggctccg atgaccctgc gttgtaccgt gggttctccg | 1500 |
| ccgcgtcgtg tggactgtac cattcatcgt ccgtctaacg gcggcctgat cgtagaactg | 1560 |
| gaaccagcaa ccaagctcga gggaggcagc cgggaccaca tggtgctgca cgagtacgtg | 1620 |
| aacgccgccg gcatcaca | 1638 |

<210> SEQ ID NO 22
<211> LENGTH: 1635

```
<212> TYPE: DNA
<213> ORGANISM: Artificial Sequence
<220> FEATURE:
<223> OTHER INFORMATION: (Nucleic acid sequence of iNS3(+) 3.3)

<400> SEQUENCE: 22
atgtccaaag gagaagaact gtttaccggt gttgtgccaa ttttggttga actcgatggt      60
gatgtcaacg gacataagtt ctcagtgaga ggcgaaggag aaggtgacgc caccattgga     120
aaattgactc ttaaattcat ctgtactact ggtaaacttc ctgtaccatg gccgactctc     180
gtaacaacgc ttacgtacgg agttcagtgc ttttcgagat acccagacca tatgaaaaga     240
catgactttt ttaagtcggc tatgcctgaa ggttacgtgc aagaaagaac aatttcgttc     300
aaagatgatg gaaaatataa aactagagca gttgttaaat ttgaaggaga tactttggtt     360
aaccgcattg aactgaaagg aacagatttt aaagaagatg gtaatattct tggacacaaa     420
ctcgaataca atttttaatag tcataacgta tacatcactg ctgataagca aagaacgga      480
attaaagcga atttcacagt acgccataat gtagaagatg gcagtgttca acttgccgac     540
cattaccaac aaaacacccc tattggagac ggtccggtac ttcttcctga taatcactac     600
ctctcaacac aaacagtcct gagcaaagat ccaaatgaaa aaggaggcag cggatccacc     660
actaacattg cgccggctct ggacggtgcg tttcatcgta tcacttcttc atcctccctg     720
atgggcctgt gtgacgaaac cgcgactatt atccgtgaga ttactggcta cgaccgtgtg     780
atggtagtac gtttcgatga gagggtaat ggcgaaattc tgtccgaacg tcgtcgtgcg      840
gacctggaag cgttcctggg taaccgctac ccggcgtcta ctattccgca gatcgctcgt     900
cgcctgtacg aacataaccg tgttcgcctg ctggtagatg tgaactatac tccggttccg     960
ctacagccgc gcatcagccc gctgaacggt cgtgatctgg atatgtccct gtcttgcctg    1020
cgctctatgt ccccgatcca ccagaaatac atgcaggaca tgggcgttgg cgcgaccctg    1080
gtttgctctc tgatggtgtc tggtcgtctg tggggtctga tcgcttgcca ccactacgaa    1140
ccgcgcttcg ttccgttcca cattcgcgct gctggcgaag cgctggcgga aacttgtgcg    1200
atccgcatcg cgacgctgga gagcgaggac gtggtgtgct gctcagaatt ctgtgaacgc    1260
gagcagatcc acctggcggg ctccattcag ccgcacggta tcctgctggc tgtgaaagag    1320
ccggacaacg tggtgatcca ggcttctatt aacgctgcgg agttcctgaa caccaactct    1380
gttgttggcc gtccgctgcg tgacctgggc ggcgatctgc ctttgcagat cctgccgcac    1440
ctgaacggcc cgctgcacct ggctccgatg accctgcgtt gtaccgtggg ttctccgccg    1500
cgtcgtgtgg actgtaccat tcatcgtccg tctaacggcg gcctgatcgt agaactggaa    1560
ccagcaacca agctcgaggg aggcagccgg gaccacatgg tgctgcacga gtacgtgaac    1620
gccgccggca tcaca                                                    1635

<210> SEQ ID NO 23
<211> LENGTH: 1641
<212> TYPE: DNA
<213> ORGANISM: Artificial Sequence
<220> FEATURE:
<223> OTHER INFORMATION: (Nucleic acid sequence of iCalpain(+) 1.0)

<400> SEQUENCE: 23
atgtccaaag gagaagaact gtttaccggt gttgtgccaa ttttggttga actcgatggt      60
gatgtcaacg gacataagtt ctcagtgaga ggcgaaggag aaggtgacgc caccattgga     120
aaattgactc ttaaattcat ctgtactact ggtaaacttc ctgtaccatg gccgactctc     180
```

```
gtaacaacgc ttacgtacgg agttcagtgc ttttcgagat acccagacca tatgaaaaga    240
catgactttt ttaagtcggc tatgcctgaa ggttacgtgc aagaaagaac aatttcgttc    300
aaagatgatg gaaatataa aactagagca gttgttaaat ttgaaggaga actttggtt     360 aaccgcattg aactgaaagg aacagatttt aaagaagatg gtaatattct tggacacaaa    420
ctcgaataca attttaatag tcataacgta tacatcactg ctgataagca aaagaacgga    480
attaaagcga atttcacagt acgccataat gtagaagatg gcagtgttca acttgccgac    540
cattaccaac aaaacacccc tattggagac ggtccggtac ttcttcctga taatcactac    600
ctctcaacac aaacagtcct gagcaaagat ccaaatgaaa aaggaggcag cggatccacc    660
actaacattg cgccggctct ggacggtgcg tttcatcgta tcacttcttc atcctccctg    720
atgggcctgt gtgacgaaac cgcgactatt atccgtgaga ttactggcta cgaccgtgtg    780
atggtagtac gtttcgatga agagggtaat ggcgaaattc tgtccgaacg tcgtcgtgcg    840
gacctggaag cgttcctggg taaccgctac ccggcgtcta ctattccgca gatcgctcgt    900
cgcctgtacg aacataaccg tgttcgcctg ctggtagatg tgaactatac tccggttccg    960
ctacagccgc gcatcagccc gctgaacggt cgtgatctgg atatgtccct gtcttgcctg   1020
cgctctatgt ccccgatcca ccagaaatac atgcaggaca tgggcgttgg cgcgaccctg   1080
gtttgctctc tgatggtgtc tggtcgtctg tggggtctga tcgcttgcca ccactacgaa   1140
ccgcgcttcg ttccgttcca cattcgcgct gctggcgaag cgctggcgga aacttgtgcg   1200
atccgcatcg cgacgctgga gagccagcag gaggtatacg catgatgcc tcgcgattgt   1260 gaacgcgagc agatccacct ggcgggctcc attcagccgc acggtatcct gctggctgtg   1320
aaagagccgg acaacgtggt gatccaggct tctattaacg ctgcggagtt cctgaacacc   1380
aactctgttg ttggccgtcc gctgcgtgac ctgggcggcg atctgccttt gcagatcctg   1440
ccgcacctga acggcccgct gcacctggct ccgatgaccc tgcgttgtac cgtgggttct   1500
ccgccgcgtc gtgtggactg taccattcat cgtccgtcta acggcggcct gatcgtagaa   1560
ctggaaccag caaccaagct cgagggaggc agccgggacc acatggtgct gcacgagtac   1620
gtgaacgccg ccggcatcac a                                              1641
```

<210> SEQ ID NO 24
<211> LENGTH: 557
<212> TYPE: PRT
<213> ORGANISM: Artificial Sequence
<220> FEATURE:
<223> OTHER INFORMATION: (Amino acid sequence of iTEV(+) 1.0)

<400> SEQUENCE: 24

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
                20                  25                  30

Gly Glu Gly Asp Ala Thr Ile Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val

```
                100              105                110
Lys Phe Glu Gly Asp Thr Leu Val Asn Arg Ile Glu Leu Lys Gly Thr
            115                  120              125

Asp Phe Lys Glu Asp Gly Asn Ile Leu Gly His Lys Leu Glu Tyr Asn
130             135                  140

Phe Asn Ser His Asn Val Tyr Ile Thr Ala Asp Lys Gln Lys Asn Gly
145                 150                  155              160

Ile Lys Ala Asn Phe Thr Val Arg His Asn Val Glu Asp Gly Ser Val
                165                  170              175

Gln Leu Ala Asp His Tyr Gln Gln Asn Thr Pro Ile Gly Asp Gly Pro
            180                  185              190

Val Leu Leu Pro Asp Asn His Tyr Leu Ser Thr Gln Thr Val Leu Ser
        195                  200              205

Lys Asp Pro Asn Glu Lys Gly Gly Ser Gly Ser Thr Thr Asn Ile Ala
210                  215                  220

Pro Ala Leu Asp Gly Ala Phe His Arg Ile Thr Ser Ser Ser Ser Leu
225                 230                  235              240

Met Gly Leu Cys Asp Glu Thr Ala Thr Ile Ile Arg Glu Ile Thr Gly
                245                  250                  255

Tyr Asp Arg Val Met Val Arg Phe Asp Glu Gly Asn Gly Glu
                260                  265              270

Ile Leu Ser Glu Arg Arg Ala Asp Leu Glu Ala Phe Leu Gly Asn
            275                  280              285

Arg Tyr Pro Ala Ser Thr Ile Pro Gln Ile Ala Arg Arg Leu Tyr Glu
            290                  295              300

His Asn Arg Val Arg Leu Leu Val Asp Val Asn Tyr Thr Pro Val Pro
305                  310                  315              320

Leu Gln Pro Arg Ile Ser Pro Leu Asn Gly Arg Asp Leu Asp Met Ser
                325                  330                  335

Leu Ser Cys Leu Arg Ser Met Ser Pro Ile His Gln Lys Tyr Met Gln
                340                  345                  350

Asp Met Gly Val Gly Ala Thr Leu Val Cys Ser Leu Met Val Ser Gly
            355                  360                  365

Arg Leu Trp Gly Leu Ile Ala Cys His His Tyr Glu Pro Arg Phe Val
            370                  375              380

Pro Phe His Ile Arg Ala Ala Gly Glu Ala Leu Ala Glu Thr Cys Ala
385                  390                  395              400

Ile Arg Ile Ala Thr Leu Glu Ser Phe Ala Gln Ser Gln Ser Lys Glu
                405                  410              415

Asn Leu Tyr Phe Gln Ser Glu Phe Ala Phe Leu Ala Asn Cys Glu Arg
                420                  425              430

Glu Gln Ile His Leu Ala Gly Ser Ile Gln Pro His Gly Ile Leu Leu
            435                  440              445

Ala Val Lys Glu Pro Asp Asn Val Val Ile Gln Ala Ser Ile Asn Ala
450                  455                  460

Ala Glu Phe Leu Asn Thr Asn Ser Val Val Gly Arg Pro Leu Arg Asp
465             470                  475              480

Leu Gly Gly Asp Leu Pro Leu Gln Ile Leu Pro His Leu Asn Gly Pro
                485                  490              495

Leu His Leu Ala Pro Met Thr Leu Arg Cys Thr Val Gly Ser Pro Pro
            500                  505              510

Arg Arg Val Asp Cys Thr Ile His Arg Pro Ser Asn Gly Gly Leu Ile
            515                  520              525
```

```
Val Glu Leu Glu Pro Ala Thr Lys Leu Glu Gly Gly Ser Arg Asp His
    530                 535                 540

Met Val Leu His Glu Tyr Val Asn Ala Ala Gly Ile Thr
545                 550                 555

<210> SEQ ID NO 25
<211> LENGTH: 552
<212> TYPE: PRT
<213> ORGANISM: Artificial Sequence
<220> FEATURE:
<223> OTHER INFORMATION: (Amino acid sequence of iTEV(+) 2.1)

<400> SEQUENCE: 25

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Ser Thr Thr Asn Ile Ala
    210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Val Arg Phe Asp Glu Glu Gly Asn Gly Glu
            260                 265                 270

Ile Leu Ser Glu Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
    290                 295                 300

His Asn Arg Val Arg Leu Leu Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335
```

```
Leu Ser Cys Leu Arg Ser Met Ser Pro Ile His Gln Lys Tyr Met Gln
                340                 345                 350

Asp Met Gly Val Gly Ala Thr Leu Val Cys Ser Leu Met Val Ser Gly
            355                 360                 365

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Phe Ala Gln Ser Gln Ser Lys Glu
                405                 410                 415

Asn Leu Tyr Phe Gln Ser Glu Phe Cys Glu Arg Glu Gln Ile His Leu
            420                 425                 430

Ala Gly Ser Ile Gln Pro His Gly Ile Leu Leu Ala Val Lys Glu Pro
        435                 440                 445

Asp Asn Val Val Ile Gln Ala Ser Ile Asn Ala Ala Glu Phe Leu Asn
    450                 455                 460

Thr Asn Ser Val Val Gly Arg Pro Leu Arg Asp Leu Gly Gly Asp Leu
465                 470                 475                 480

Pro Leu Gln Ile Leu Pro His Leu Asn Gly Pro Leu His Leu Ala Pro
                485                 490                 495

Met Thr Leu Arg Cys Thr Val Gly Ser Pro Pro Arg Arg Val Asp Cys
            500                 505                 510

Thr Ile His Arg Pro Ser Asn Gly Gly Leu Ile Val Glu Leu Glu Pro
        515                 520                 525

Ala Thr Lys Leu Glu Gly Gly Ser Arg Asp His Met Val Leu His Glu
    530                 535                 540

Tyr Val Asn Ala Ala Gly Ile Thr
545                 550

<210> SEQ ID NO 26
<211> LENGTH: 545
<212> TYPE: PRT
<213> ORGANISM: Artificial Sequence
<220> FEATURE:
<223> OTHER INFORMATION: (Amino acid sequence of iTEV(+) 3.0)

<400> SEQUENCE: 26

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140
```

```
Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
                195                 200                 205

Lys Asp Pro Asn Glu Lys Gly Gly Ser Gly Ser Thr Thr Asn Ile Ala
            210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Glu Gly Asn Gly Glu
                260                 265                 270

Ile Leu Ser Glu Arg Arg Ala Asp Leu Glu Ala Phe Leu Gly Asn
            275                 280                 285

Arg Tyr Pro Ala Ser Thr Ile Pro Gln Ile Ala Arg Arg Leu Tyr Glu
290                 295                 300

His Asn Arg Val Arg Leu Leu Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Cys Ser Leu Met Val Ser Gly
            355                 360                 365

Arg Leu Trp Gly Leu Ile Ala Cys His His Tyr Glu Pro Arg Phe Val
    370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Glu Asn Leu Tyr Phe Gln Ser Glu
                405                 410                 415

Phe Cys Glu Arg Glu Gln Ile His Leu Ala Gly Ser Ile Gln Pro His
                420                 425                 430

Gly Ile Leu Leu Ala Val Lys Glu Pro Asp Asn Val Val Ile Gln Ala
            435                 440                 445

Ser Ile Asn Ala Ala Glu Phe Leu Asn Thr Asn Ser Val Val Gly Arg
450                 455                 460

Pro Leu Arg Asp Leu Gly Gly Asp Leu Pro Leu Gln Ile Leu Pro His
465                 470                 475                 480

Leu Asn Gly Pro Leu His Leu Ala Pro Met Thr Leu Arg Cys Thr Val
                485                 490                 495

Gly Ser Pro Pro Arg Arg Val Asp Cys Thr Ile His Arg Pro Ser Asn
            500                 505                 510

Gly Gly Leu Ile Val Glu Leu Glu Pro Ala Thr Lys Leu Glu Gly Gly
            515                 520                 525

Ser Arg Asp His Met Val Leu His Glu Tyr Val Asn Ala Ala Gly Ile
    530                 535                 540

Thr
545
```

<210> SEQ ID NO 27
<211> LENGTH: 546
<212> TYPE: PRT
<213> ORGANISM: Artificial Sequence
<220> FEATURE:
<223> OTHER INFORMATION: (Amino acid sequence of iTEV(+) 3.1)

<400> SEQUENCE: 27

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Ser Thr Thr Asn Ile Ala
    210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Glu Gly Asn Gly Glu
            260                 265                 270

Ile Leu Ser Glu Arg Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
    290                 295                 300

His Asn Arg Val Arg Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Cys Ser Leu Met Val Ser Gly
        355                 360                 365
```

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Phe Glu Asn Leu Tyr Phe Gln Ser
                405                 410                 415

Glu Phe Cys Glu Arg Glu Gln Ile His Leu Ala Gly Ser Ile Gln Pro
            420                 425                 430

His Gly Ile Leu Leu Ala Val Lys Glu Pro Asp Asn Val Val Ile Gln
        435                 440                 445

Ala Ser Ile Asn Ala Ala Glu Phe Leu Asn Thr Asn Ser Val Val Gly
450                 455                 460

Arg Pro Leu Arg Asp Leu Gly Asp Leu Pro Leu Gln Ile Leu Pro
465                 470                 475                 480

His Leu Asn Gly Pro Leu His Leu Ala Pro Met Thr Leu Arg Cys Thr
                485                 490                 495

Val Gly Ser Pro Pro Arg Arg Val Asp Cys Thr Ile His Arg Pro Ser
            500                 505                 510

Asn Gly Gly Leu Ile Val Glu Leu Pro Ala Thr Lys Leu Glu Gly
        515                 520                 525

Gly Ser Arg Asp His Met Val Leu His Glu Tyr Val Asn Ala Ala Gly
530                 535                 540

Ile Thr
545

<210> SEQ ID NO 28
<211> LENGTH: 547
<212> TYPE: PRT
<213> ORGANISM: Artificial Sequence
<220> FEATURE:
<223> OTHER INFORMATION: (Amino acid sequence of iTEV(+) 3.2)

<400> SEQUENCE: 28

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

-continued

```
Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Ser Thr Thr Asn Ile Ala
210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Glu Gly Asn Gly Glu
            260                 265                 270

Ile Leu Ser Glu Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Cys Ser Leu Met Val Ser Gly
        355                 360                 365

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Phe Ala Glu Asn Leu Tyr Phe Gln
                405                 410                 415

Ser Glu Phe Cys Glu Arg Glu Gln Ile His Leu Ala Gly Ser Ile Gln
            420                 425                 430

Pro His Gly Ile Leu Leu Ala Val Lys Glu Pro Asp Asn Val Val Ile
        435                 440                 445

Gln Ala Ser Ile Asn Ala Ala Glu Phe Leu Asn Thr Asn Ser Val Val
450                 455                 460

Gly Arg Pro Leu Arg Asp Leu Gly Gly Asp Leu Pro Leu Gln Ile Leu
465                 470                 475                 480

Pro His Leu Asn Gly Pro Leu His Leu Ala Pro Met Thr Leu Arg Cys
                485                 490                 495

Thr Val Gly Ser Pro Pro Arg Arg Val Asp Cys Thr Ile His Arg Pro
            500                 505                 510

Ser Asn Gly Gly Leu Ile Val Glu Leu Glu Pro Ala Thr Lys Leu Glu
        515                 520                 525

Gly Gly Ser Arg Asp His Met Val Leu His Glu Tyr Val Asn Ala Ala
530                 535                 540

Gly Ile Thr
545
```

<210> SEQ ID NO 29
<211> LENGTH: 548
<212> TYPE: PRT
<213> ORGANISM: Artificial Sequence
<220> FEATURE:
<223> OTHER INFORMATION: (Amino acid sequence of iTEV(+) 3.3)

<400> SEQUENCE: 29

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Ser Thr Thr Asn Ile Ala
210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Glu Gly Asn Gly Glu
            260                 265                 270

Ile Leu Ser Glu Arg Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Cys Ser Leu Met Val Ser Gly
        355                 360                 365

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Phe Ala Gln Glu Asn Leu Tyr Phe

```
                    405                 410                 415
Gln Ser Glu Phe Cys Glu Arg Glu Gln Ile His Leu Ala Gly Ser Ile
                420                 425                 430
Gln Pro His Gly Ile Leu Leu Ala Val Lys Glu Pro Asp Asn Val Val
            435                 440                 445
Ile Gln Ala Ser Ile Asn Ala Ala Glu Phe Leu Asn Thr Asn Ser Val
        450                 455                 460
Val Gly Arg Pro Leu Arg Asp Leu Gly Asp Leu Pro Leu Gln Ile
465                 470                 475                 480
Leu Pro His Leu Asn Gly Pro Leu His Leu Ala Pro Met Thr Leu Arg
                485                 490                 495
Cys Thr Val Gly Ser Pro Pro Arg Arg Val Asp Cys Thr Ile His Arg
                500                 505                 510
Pro Ser Asn Gly Gly Leu Ile Val Glu Leu Glu Pro Ala Thr Lys Leu
            515                 520                 525
Glu Gly Gly Ser Arg Asp His Met Val Leu His Glu Tyr Val Asn Ala
        530                 535                 540
Ala Gly Ile Thr
545

<210> SEQ ID NO 30
<211> LENGTH: 549
<212> TYPE: PRT
<213> ORGANISM: Artificial Sequence
<220> FEATURE:
<223> OTHER INFORMATION: (Amino acid sequence of iTEV(+) 3.4)

<400> SEQUENCE: 30

Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Arg Gly Glu
                20                  25                  30
Gly Glu Gly Asp Ala Thr Ile Gly Lys Leu Thr Leu Lys Phe Ile Cys
            35                  40                  45
Thr Thr Gly Lys Leu Pro Val Pro Trp Pro Thr Leu Val Thr Thr Leu
        50                  55                  60
Thr Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Ser Phe Lys Asp Asp Gly Lys Tyr Lys Thr Arg Ala Val Val
            100                 105                 110
Lys Phe Glu Gly Asp Thr Leu Val Asn Arg Ile Glu Leu Lys Gly Thr
        115                 120                 125
Asp Phe Lys Glu Asp Gly Asn Ile Leu Gly His Lys Leu Glu Tyr Asn
    130                 135                 140
Phe Asn Ser His Asn Val Tyr Ile Thr Ala Asp Lys Gln Lys Asn Gly
145                 150                 155                 160
Ile Lys Ala Asn Phe Thr Val Arg His Asn Val Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Thr Val Leu Ser
        195                 200                 205
Lys Asp Pro Asn Glu Lys Gly Gly Ser Gly Ser Thr Thr Asn Ile Ala
```

```
Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
            245                 250                 255

Tyr Asp Arg Val Met Val Val Arg Phe Asp Glu Glu Gly Asn Gly Glu
        260                 265                 270

Ile Leu Ser Glu Arg Arg Ala Asp Leu Glu Ala Phe Leu Gly Asn
    275                 280                 285

Arg Tyr Pro Ala Ser Thr Ile Pro Gln Ile Ala Arg Arg Leu Tyr Glu
290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Cys Ser Leu Met Val Ser Gly
        355                 360                 365

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Phe Ala Gln Ser Glu Asn Leu Tyr
                405                 410                 415

Phe Gln Ser Glu Phe Cys Glu Arg Glu Gln Ile His Leu Ala Gly Ser
            420                 425                 430

Ile Gln Pro His Gly Ile Leu Leu Ala Val Lys Glu Pro Asp Asn Val
        435                 440                 445

Val Ile Gln Ala Ser Ile Asn Ala Ala Glu Phe Leu Asn Thr Asn Ser
450                 455                 460

Val Val Gly Arg Pro Leu Arg Asp Leu Gly Gly Asp Leu Pro Leu Gln
465                 470                 475                 480

Ile Leu Pro His Leu Asn Gly Pro Leu His Leu Ala Pro Met Thr Leu
                485                 490                 495

Arg Cys Thr Val Gly Ser Pro Pro Arg Arg Val Asp Cys Thr Ile His
            500                 505                 510

Arg Pro Ser Asn Gly Gly Leu Ile Val Glu Leu Glu Pro Ala Thr Lys
        515                 520                 525

Leu Glu Gly Gly Ser Arg Asp His Met Val Leu His Glu Tyr Val Asn
530                 535                 540

Ala Ala Gly Ile Thr
545

<210> SEQ ID NO 31
<211> LENGTH: 550
<212> TYPE: PRT
<213> ORGANISM: Artificial Sequence
<220> FEATURE:
<223> OTHER INFORMATION: (Amino acid sequence of iTEV(+) 3.5)

<400> SEQUENCE: 31

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
```

```
            20                  25                  30
Gly Glu Gly Asp Ala Thr Ile Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Thr Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Ser Phe Lys Asp Gly Lys Tyr Lys Thr Arg Ala Val Val
            100                 105                 110
Lys Phe Glu Gly Asp Thr Leu Val Asn Arg Ile Glu Leu Lys Gly Thr
        115                 120                 125
Asp Phe Lys Glu Asp Gly Asn Ile Leu Gly His Lys Leu Glu Tyr Asn
    130                 135                 140
Phe Asn Ser His Asn Val Tyr Ile Thr Ala Asp Lys Gln Lys Asn Gly
145                 150                 155                 160
Ile Lys Ala Asn Phe Thr Val Arg His Asn Val Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Thr Val Leu Ser
        195                 200                 205
Lys Asp Pro Asn Glu Lys Gly Gly Ser Gly Ser Thr Thr Asn Ile Ala
    210                 215                 220
Pro Ala Leu Asp Gly Ala Phe His Arg Ile Thr Ser Ser Ser Ser Leu
225                 230                 235                 240
Met Gly Leu Cys Asp Glu Thr Ala Thr Ile Ile Arg Glu Ile Thr Gly
                245                 250                 255
Tyr Asp Arg Val Met Val Val Arg Phe Asp Glu Glu Gly Asn Gly Glu
            260                 265                 270
Ile Leu Ser Glu Arg Arg Arg Ala Asp Leu Glu Ala Phe Leu Gly Asn
        275                 280                 285
Arg Tyr Pro Ala Ser Thr Ile Pro Gln Ile Ala Arg Arg Leu Tyr Glu
    290                 295                 300
His Asn Arg Val Arg Leu Leu Asp Val Asn Tyr Thr Pro Val Pro
305                 310                 315                 320
Leu Gln Pro Arg Ile Ser Pro Leu Asn Gly Arg Asp Leu Asp Met Ser
                325                 330                 335
Leu Ser Cys Leu Arg Ser Met Ser Pro Ile His Gln Lys Tyr Met Gln
            340                 345                 350
Asp Met Gly Val Gly Ala Thr Leu Val Cys Ser Leu Met Val Ser Gly
        355                 360                 365
Arg Leu Trp Gly Leu Ile Ala Cys His His Tyr Glu Pro Arg Phe Val
    370                 375                 380
Pro Phe His Ile Arg Ala Ala Gly Glu Ala Leu Ala Glu Thr Cys Ala
385                 390                 395                 400
Ile Arg Ile Ala Thr Leu Glu Ser Phe Ala Gln Ser Gln Glu Asn Leu
                405                 410                 415
Tyr Phe Gln Ser Glu Phe Cys Glu Arg Glu Gln Ile His Leu Ala Gly
            420                 425                 430
Ser Ile Gln Pro His Gly Ile Leu Leu Ala Val Lys Glu Pro Asp Asn
        435                 440                 445
```

Val Val Ile Gln Ala Ser Ile Asn Ala Ala Glu Phe Leu Asn Thr Asn
450                 455                 460

Ser Val Val Gly Arg Pro Leu Arg Asp Leu Gly Asp Leu Pro Leu
465                 470                 475                 480

Gln Ile Leu Pro His Leu Asn Gly Pro Leu His Leu Ala Pro Met Thr
                485                 490                 495

Leu Arg Cys Thr Val Gly Ser Pro Pro Arg Arg Val Asp Cys Thr Ile
            500                 505                 510

His Arg Pro Ser Asn Gly Gly Leu Ile Val Glu Leu Glu Pro Ala Thr
        515                 520                 525

Lys Leu Glu Gly Gly Ser Arg Asp His Met Val Leu His Glu Tyr Val
    530                 535                 540

Asn Ala Ala Gly Ile Thr
545                 550

<210> SEQ ID NO 32
<211> LENGTH: 551
<212> TYPE: PRT
<213> ORGANISM: Artificial Sequence
<220> FEATURE:
<223> OTHER INFORMATION: (Amino acid sequence of iTEV(+) 3.6)

<400> SEQUENCE: 32

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Ser Gly Ser Thr Thr Asn Ile Ala
    210                 215                 220

Pro Ala Leu Asp Gly Ala Phe His Arg Ile Thr Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Glu Gly Asn Gly Glu
            260                 265                 270

Ile Leu Ser Glu Arg Arg Ala Asp Leu Glu Ala Phe Leu Gly Asn
            275                 280                 285

Arg Tyr Pro Ala Ser Thr Ile Pro Gln Ile Ala Arg Arg Leu Tyr Glu
            290                 295                 300

His Asn Arg Val Arg Leu Leu Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Cys Ser Leu Met Val Ser Gly
            355                 360                 365

Arg Leu Trp Gly Leu Ile Ala Cys His His Tyr Glu Pro Arg Phe Val
            370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Phe Ala Gln Ser Gln Ser Glu Asn
                405                 410                 415

Leu Tyr Phe Gln Ser Glu Phe Cys Glu Arg Glu Gln Ile His Leu Ala
            420                 425                 430

Gly Ser Ile Gln Pro His Gly Ile Leu Leu Ala Val Lys Glu Pro Asp
            435                 440                 445

Asn Val Val Ile Gln Ala Ser Ile Asn Ala Ala Glu Phe Leu Asn Thr
            450                 455                 460

Asn Ser Val Val Gly Arg Pro Leu Arg Asp Leu Gly Gly Asp Leu Pro
465                 470                 475                 480

Leu Gln Ile Leu Pro His Leu Asn Gly Pro Leu His Leu Ala Pro Met
                485                 490                 495

Thr Leu Arg Cys Thr Val Gly Ser Pro Pro Arg Arg Val Asp Cys Thr
            500                 505                 510

Ile His Arg Pro Ser Asn Gly Gly Leu Ile Val Glu Leu Glu Pro Ala
            515                 520                 525

Thr Lys Leu Glu Gly Gly Ser Arg Asp His Met Val Leu His Glu Tyr
            530                 535                 540

Val Asn Ala Ala Gly Ile Thr
545                 550

<210> SEQ ID NO 33
<211> LENGTH: 545
<212> TYPE: PRT
<213> ORGANISM: Artificial Sequence
<220> FEATURE:
<223> OTHER INFORMATION: (Amino acid sequence of iTEV(+) 6.01)

<400> SEQUENCE: 33

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
                20                  25                  30

Gly Glu Gly Asp Ala Thr Ile Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

```
Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Ser Thr Thr Asn Ile Ala
210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Val Arg Phe Asp Glu Glu Gly Asn Ala Glu
            260                 265                 270

Ile Leu Ser Glu Arg Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Ser Ser Leu Met Val Ser Gly
        355                 360                 365

Arg Leu Trp Gly Leu Ile Ala Cys His His Tyr Glu Pro Arg Phe Val
370                 375                 380

Pro Phe Gln Ile Arg Ala Ala Cys Glu Ala Leu Ala Glu Thr Cys Ala
385                 390                 395                 400

Asn Arg Ile Ala Thr Leu Glu Ser Glu Asn Leu Tyr Phe Gln Ser Glu
                405                 410                 415

Phe Cys Glu Arg Glu Gln Ile His Leu Ala Gly Ser Ile Gln Pro His
            420                 425                 430

Gly Ile Leu Leu Ala Val Lys Glu Pro Asp Asn Val Val Ile Gln Ala
        435                 440                 445

Ser Ile Asn Ala Ala Glu Phe Leu Asn Ile Asn Ser Val Val Gly Arg
450                 455                 460

Pro Leu Arg Asp Leu Gly Gly Asp Leu Pro Leu Gln Ile Leu Pro His
465                 470                 475                 480
```

```
Leu Asn Gly Pro Leu His Leu Ala Pro Val Thr Leu Arg Cys Thr Val
            485                 490                 495
Gly Ser Pro Pro Arg Arg Val Asp Cys Thr Ile His Arg Pro Ser Asn
            500                 505                 510
Gly Gly Leu Ile Val Glu Leu Glu Pro Ala Thr Lys Leu Glu Gly Gly
            515                 520                 525
Ser Arg Asp His Met Val Leu His Glu Tyr Val Asn Ala Ala Gly Ile
            530                 535                 540
Thr
545

<210> SEQ ID NO 34
<211> LENGTH: 545
<212> TYPE: PRT
<213> ORGANISM: Artificial Sequence
<220> FEATURE:
<223> OTHER INFORMATION: (Amino acid sequence of iTEV(+) 6.03)

<400> SEQUENCE: 34

Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Arg Gly Glu
            20                  25                  30
Gly Glu Gly Asp Ala Thr Ile Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Thr Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Ser Phe Lys Asp Asp Gly Lys Tyr Lys Thr Arg Ala Val Val
            100                 105                 110
Lys Phe Glu Gly Asp Thr Leu Val Asn Arg Ile Glu Leu Lys Gly Thr
        115                 120                 125
Asp Phe Lys Glu Asp Gly Asn Ile Leu Gly His Lys Leu Glu Tyr Asn
    130                 135                 140
Phe Asn Ser His Asn Val Tyr Ile Thr Ala Asp Lys Gln Lys Asn Gly
145                 150                 155                 160
Ile Lys Ala Asn Phe Thr Val Arg His Asn Val Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Thr Val Leu Ser
        195                 200                 205
Lys Asp Pro Asn Glu Lys Gly Gly Ser Gly Ser Thr Thr Asn Ile Ala
    210                 215                 220
Pro Ala Leu Asp Gly Ala Phe His Arg Ile Thr Ser Ser Ser Ser Leu
225                 230                 235                 240
Met Gly Leu Cys Asp Glu Thr Ala Thr Ile Ile Arg Glu Ile Thr Gly
                245                 250                 255
Tyr Asp Arg Val Met Val Val Arg Phe Asp Glu Gly Asn Ala Glu
            260                 265                 270
Ile Leu Ser Glu Arg Arg Arg Ala Asp Leu Glu Ala Phe Leu Gly Asn
        275                 280                 285
```

Arg Tyr Pro Ala Ser Thr Ile Pro Gln Ile Ala Arg Leu Tyr Glu
    290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Val His Gln Lys Tyr Met Gln
                340                 345                 350

Asp Met Gly Val Gly Ala Thr Leu Val Cys Ser Leu Met Val Ser Gly
                355                 360                 365

Arg Leu Trp Gly Leu Ile Ala Cys His His Tyr Glu Pro Arg Phe Val
    370                 375                 380

Pro Phe His Ile Arg Ala Ala Gly Glu Ala Leu Ala Glu Thr Cys Ala
385                 390                 395                 400

Asn Arg Ile Ala Thr Leu Glu Ser Glu Asn Leu Tyr Phe Gln Ser Glu
                405                 410                 415

Phe Cys Glu Arg Glu Gln Ile His Leu Ala Gly Ser Ile Gln Pro His
                420                 425                 430

Gly Ile Leu Leu Ala Val Lys Glu Pro Asp Asn Val Val Ile Gln Ala
            435                 440                 445

Ser Ile Asn Ala Ala Glu Phe Leu Asn Thr Asn Ser Val Val Gly Arg
    450                 455                 460

Pro Leu Arg Asp Leu Gly Asp Leu Pro Leu Gln Ile Leu Pro His
465                 470                 475                 480

Leu Asn Gly Pro Leu His Leu Ala Pro Val Thr Leu Arg Cys Thr Val
                485                 490                 495

Gly Ser Pro Pro Arg Arg Val Asp Cys Thr Ile His Arg Pro Ser Asn
                500                 505                 510

Gly Gly Leu Ile Val Glu Leu Glu Pro Ala Thr Lys Leu Glu Gly Gly
            515                 520                 525

Ser Arg Asp His Met Val Leu His Glu Tyr Val Asn Ala Ala Gly Ile
    530                 535                 540

Thr
545

<210> SEQ ID NO 35
<211> LENGTH: 544
<212> TYPE: PRT
<213> ORGANISM: Artificial Sequence
<220> FEATURE:
<223> OTHER INFORMATION: (Amino acid sequence of iTEV(+) 6.04)

<400> SEQUENCE: 35

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
                20                  25                  30

Glu Gly Asp Ala Thr Ile Gly Lys Leu Thr Leu Lys Phe Ile Cys Thr
            35                  40                  45

Thr Gly Lys Leu Pro Val Pro Trp Pro Thr Leu Val Thr Thr Leu Thr
    50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

-continued

```
Ile Ser Phe Lys Asp Asp Gly Lys Tyr Lys Thr Arg Ala Val Val Lys
            100                 105                 110

Phe Glu Gly Asp Thr Leu Val Asn Arg Ile Glu Leu Lys Gly Thr Asp
        115                 120                 125

Phe Lys Glu Asp Gly Asn Ile Leu Gly His Lys Leu Glu Tyr Asn Phe
    130                 135                 140

Asn Ser His Asn Val Tyr Ile Thr Ala Asp Lys Gln Lys Asn Gly Ile
145                 150                 155                 160

Lys Ala Asn Phe Thr Val Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Thr Val Leu Ser Lys
        195                 200                 205

Asp Pro Asn Glu Lys Gly Gly Ser Gly Ser Thr Thr Asn Ile Ala Pro
    210                 215                 220

Ala Leu Asp Gly Ala Phe His Arg Ile Thr Ser Ser Ser Leu Met
225                 230                 235                 240

Gly Leu Cys Asp Glu Thr Ala Thr Ile Ile Arg Glu Ile Thr Gly Tyr
                245                 250                 255

Asp Arg Val Met Val Arg Phe Asp Glu Glu Gly Asn Ala Glu Ile
            260                 265                 270

Leu Ser Glu Arg Arg Arg Ala Asp Leu Glu Ala Phe Leu Gly Asn Arg
        275                 280                 285

Tyr Pro Ala Ser Thr Ile Pro Gln Ile Ala Arg Arg Leu Tyr Glu His
    290                 295                 300

Asn Arg Val Arg Leu Leu Val Asp Val Asn Tyr Thr Pro Val Pro Leu
305                 310                 315                 320

Gln Pro Arg Ile Ser Pro Leu Asn Gly Arg Asp Leu Asp Met Ser Leu
                325                 330                 335

Ser Cys Leu Arg Ser Met Ser Pro Ile His Gln Lys Tyr Met Gln Asp
            340                 345                 350

Met Gly Val Gly Ala Thr Leu Val Cys Ser Leu Met Val Ser Gly Arg
        355                 360                 365

Leu Trp Gly Leu Ile Ala Cys His His Tyr Glu Pro Arg Phe Val Pro
    370                 375                 380

Phe His Ile Arg Ala Ala Gly Glu Ala Leu Ala Glu Thr Cys Ala Asn
385                 390                 395                 400

Arg Ile Ala Thr Leu Glu Ser Glu Asn Leu Tyr Phe Gln Ser Glu Phe
                405                 410                 415

Cys Glu Arg Glu Gln Ile His Leu Ala Gly Ser Ile Gln Pro His Gly
            420                 425                 430

Ile Leu Leu Ala Val Lys Glu Pro Asp Asn Val Val Ile Gln Ala Ser
        435                 440                 445

Ile Asn Ala Ala Glu Phe Leu Asn Thr Asn Ser Val Val Gly Arg Pro
    450                 455                 460

Leu Arg Asp Leu Gly Gly Asp Leu Pro Leu Gln Ile Leu Pro His Leu
465                 470                 475                 480

Asn Gly Pro Leu His Leu Ala Pro Val Thr Leu Arg Cys Thr Val Gly
                485                 490                 495

Ser Pro Pro Arg Arg Val Asp Cys Thr Ile His Arg Pro Ser Asn Gly
            500                 505                 510

Gly Leu Ile Val Glu Leu Glu Pro Ala Thr Lys Leu Glu Gly Gly Ser
```

```
            515                 520                 525
Arg Asp His Met Val Leu His Glu Tyr Val Asn Ala Ala Gly Ile Thr
        530                 535                 540

<210> SEQ ID NO 36
<211> LENGTH: 545
<212> TYPE: PRT
<213> ORGANISM: Artificial Sequence
<220> FEATURE:
<223> OTHER INFORMATION: (Amino acid sequence of iTEV(+) 6.05)

<400> SEQUENCE: 36

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Ser Thr Thr Asn Ile Ala
    210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Val Arg Phe Asp Glu Gly Asn Ala Glu
            260                 265                 270

Ile Leu Ser Glu Arg Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
    290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
```

```
                    340                 345                 350
Asp Met Gly Val Gly Ala Thr Leu Val Cys Ser Leu Met Val Ser Gly
            355                 360                 365
Arg Leu Trp Gly Leu Ile Ala Cys His His Tyr Glu Pro Arg Phe Val
        370                 375                 380
Pro Phe His Ile Arg Ala Ala Val Asp Ala Leu Ala Glu Thr Cys Ala
385                 390                 395                 400
Ile Arg Ile Ala Thr Leu Glu Ser Glu Asn Leu Tyr Phe Gln Ser Glu
                405                 410                 415
Phe Cys Glu Arg Glu Gln Ile His Leu Ala Gly Ser Ile Gln Pro His
            420                 425                 430
Gly Ile Leu Leu Ala Val Lys Glu Pro Asp Asn Val Val Ile Gln Ala
        435                 440                 445
Ser Ile Asn Ala Ala Glu Phe Leu Asn Thr Asn Ser Val Val Gly Arg
    450                 455                 460
Pro Leu Arg Asp Leu Gly Gly Asp Leu Pro Leu Gln Ile Leu Pro His
465                 470                 475                 480
Leu Asn Gly Pro Leu His Leu Ala Pro Val Thr Leu Arg Cys Thr Val
                485                 490                 495
Gly Ser Pro Pro Arg Arg Val Asp Cys Thr Ile His Arg Pro Ser Asn
            500                 505                 510
Gly Gly Leu Ile Val Glu Leu Glu Pro Ala Thr Lys Leu Glu Gly Gly
        515                 520                 525
Ser Arg Asp His Met Val Leu His Glu Tyr Val Asn Ala Ala Gly Ile
    530                 535                 540
Thr
545

<210> SEQ ID NO 37
<211> LENGTH: 545
<212> TYPE: PRT
<213> ORGANISM: Artificial Sequence
<220> FEATURE:
<223> OTHER INFORMATION: (Amino acid sequence of iTEV(+) 6.13)

<400> SEQUENCE: 37

Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Arg Gly Glu
            20                  25                  30
Gly Glu Gly Asp Ala Thr Ile Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Thr Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Ser Phe Lys Asp Asp Gly Lys Tyr Lys Thr Arg Ala Val Val
            100                 105                 110
Lys Phe Glu Gly Asp Thr Leu Val Asn Arg Ile Glu Leu Lys Gly Thr
        115                 120                 125
Asp Phe Lys Glu Asp Gly Asn Ile Leu Gly His Lys Leu Glu Tyr Asn
    130                 135                 140
Phe Asn Ser His Asn Val Tyr Ile Thr Ala Asp Lys Gln Lys Asn Gly
```

```
145                 150                 155                 160
Ile Lys Ala Asn Phe Thr Val Arg His Asn Val Glu Asp Gly Ser Val
                165                 170                 175
Gln Leu Ala Asp His Tyr Gln Gln Asn Thr Pro Ile Gly Asp Gly Pro
                180                 185                 190
Val Leu Leu Pro Asp Asn His Tyr Leu Ser Thr Gln Thr Val Leu Ser
                195                 200                 205
Lys Asp Pro Asn Glu Lys Gly Gly Ser Gly Ser Thr Thr Asn Ile Ala
210                 215                 220
Pro Ala Leu Asp Gly Ala Phe His Arg Ile Thr Ser Ser Ser Ser Leu
225                 230                 235                 240
Met Gly Leu Cys Asp Glu Thr Ala Thr Ile Ile Arg Glu Ile Thr Gly
                245                 250                 255
Tyr Asp Arg Val Met Val Val Arg Phe Asp Glu Glu Gly Asn Ala Glu
                260                 265                 270
Ile Leu Ser Glu Arg Arg Arg Ala Asp Leu Glu Ala Phe Leu Gly Asn
                275                 280                 285
Arg Tyr Pro Ala Ser Thr Ile Pro Gln Ile Ala Arg Arg Leu Tyr Glu
290                 295                 300
His Asn Arg Val Arg Leu Leu Val Asp Val Asn Tyr Thr Pro Val Pro
305                 310                 315                 320
Leu Gln Pro Arg Ile Ser Pro Leu Asn Gly Arg Asp Leu Asp Met Ser
                325                 330                 335
Leu Ser Cys Leu Arg Ser Met Ser Pro Asn His Gln Lys Tyr Met Gln
                340                 345                 350
Asp Met Gly Val Gly Ala Thr Leu Val Cys Ser Leu Met Val Ser Gly
                355                 360                 365
Arg Leu Trp Gly Leu Ile Ala Cys His His Tyr Glu Pro Arg Phe Val
                370                 375                 380
Pro Phe His Ile Arg Ala Ala Gly Glu Ala Leu Ala Glu Thr Cys Ala
385                 390                 395                 400
Ala Arg Ile Ala Thr Leu Glu Ser Glu Asn Leu Tyr Phe Gln Ser Glu
                405                 410                 415
Phe Cys Glu Arg Glu Gln Ile His Leu Ala Gly Ser Ile Gln Pro His
                420                 425                 430
Gly Ile Leu Leu Ala Val Lys Glu Pro Asp Asn Val Val Ile Gln Ala
                435                 440                 445
Ser Ile Asn Ala Ala Glu Phe Leu Asn Thr Asn Ser Val Val Gly Arg
                450                 455                 460
Pro Leu Arg Asp Leu Gly Gly Asp Leu Pro Leu Gln Ile Leu Pro His
465                 470                 475                 480
Leu Asn Gly Pro Leu His Leu Ala Pro Val Thr Leu Arg Cys Thr Val
                485                 490                 495
Gly Ser Pro Pro Arg Arg Val Asp Cys Thr Ile His Arg Pro Ser Asn
                500                 505                 510
Gly Gly Leu Ile Val Glu Leu Glu Pro Ala Thr Lys Leu Glu Gly Gly
                515                 520                 525
Ser Arg Asp His Met Val Leu His Glu Tyr Val Asn Ala Ala Gly Ile
                530                 535                 540
Thr
545

<210> SEQ ID NO 38
```

<211> LENGTH: 393
<212> TYPE: PRT
<213> ORGANISM: Artificial Sequence
<220> FEATURE:
<223> OTHER INFORMATION: (Amino acid sequence of iTEV(+) 5.1)

<400> SEQUENCE: 38

```
Met Gly Gly Ser Lys Val Ser Ala Leu Lys Glu Lys Val Ser Ala Leu
1               5                   10                  15

Lys Glu Lys Val Ser Ala Leu Lys Glu Lys Val Ser Ala Leu Lys Glu
            20                  25                  30

Lys Val Ser Ala Leu Lys Glu Gly Gly Ser Gly Ser Thr Thr Asn Ile
        35                  40                  45

Ala Pro Ala Leu Asp Gly Ala Phe His Arg Ile Thr Ser Ser Ser Ser
    50                  55                  60

Leu Met Gly Leu Cys Asp Glu Thr Ala Thr Ile Ile Arg Glu Ile Thr
65                  70                  75                  80

Gly Tyr Asp Arg Val Met Val Arg Phe Asp Glu Glu Gly Asn Gly
                85                  90                  95

Glu Ile Leu Ser Glu Arg Arg Ala Asp Leu Glu Ala Phe Leu Gly
                100                 105                 110

Asn Arg Tyr Pro Ala Ser Thr Ile Pro Gln Ile Ala Arg Arg Leu Tyr
            115                 120                 125

Glu His Asn Arg Val Arg Leu Leu Val Asp Val Asn Tyr Thr Pro Val
130                 135                 140

Pro Leu Gln Pro Arg Ile Ser Pro Leu Asn Gly Arg Asp Leu Asp Met
145                 150                 155                 160

Ser Leu Ser Cys Leu Arg Ser Met Ser Pro Ile His Gln Lys Tyr Met
                165                 170                 175

Gln Asp Met Gly Val Gly Ala Thr Leu Val Cys Ser Leu Met Val Ser
            180                 185                 190

Gly Arg Leu Trp Gly Leu Ile Ala Cys His His Tyr Glu Pro Arg Phe
        195                 200                 205

Val Pro Phe His Ile Arg Ala Ala Gly Glu Ala Leu Ala Glu Thr Cys
    210                 215                 220

Ala Ile Arg Ile Ala Thr Leu Glu Ser Glu Asn Leu Tyr Phe Gln Ser
225                 230                 235                 240

Glu Phe Cys Glu Arg Glu Gln Ile His Leu Ala Gly Ser Ile Gln Pro
                245                 250                 255

His Gly Ile Leu Leu Ala Val Lys Glu Pro Asp Asn Val Val Ile Gln
            260                 265                 270

Ala Ser Ile Asn Ala Ala Glu Phe Leu Asn Thr Asn Ser Val Val Gly
        275                 280                 285

Arg Pro Leu Arg Asp Leu Gly Asp Leu Pro Leu Gln Ile Leu Pro
    290                 295                 300

His Leu Asn Gly Pro Leu His Leu Ala Pro Met Thr Leu Arg Cys Thr
305                 310                 315                 320

Val Gly Ser Pro Pro Arg Arg Val Asp Cys Thr Ile His Arg Pro Ser
                325                 330                 335

Asn Gly Gly Leu Ile Val Glu Leu Glu Pro Ala Thr Lys Leu Glu Gly
            340                 345                 350

Gly Gly Ser Gly Gly Ser Glu Val Ser Ala Leu Glu Lys Glu Val Ser
        355                 360                 365

Ala Leu Glu Lys Glu Val Ser Ala Leu Glu Lys Glu Val Ser Ala Leu
    370                 375                 380
```

Glu Lys Glu Val Ser Ala Leu Glu Lys
385                 390

<210> SEQ ID NO 39
<211> LENGTH: 393
<212> TYPE: PRT
<213> ORGANISM: Artificial Sequence
<220> FEATURE:
<223> OTHER INFORMATION: (Amino acid sequence of iTEV(+) 6.031)

<400> SEQUENCE: 39

Met Gly Gly Ser Lys Val Ser Ala Leu Lys Glu Lys Val Ser Ala Leu
1               5                   10                  15

Lys Glu Lys Val Ser Ala Leu Lys Glu Lys Val Ser Ala Leu Lys Glu
                20                  25                  30

Lys Val Ser Ala Leu Lys Glu Gly Gly Ser Gly Ser Thr Thr Asn Ile
            35                  40                  45

Ala Pro Ala Leu Asp Gly Ala Phe His Arg Ile Thr Ser Ser Ser Ser
        50                  55                  60

Leu Met Gly Leu Cys Asp Glu Thr Ala Thr Ile Ile Arg Glu Ile Thr
65                  70                  75                  80

Gly Tyr Asp Arg Val Met Val Val Arg Phe Asp Glu Gly Asn Ala
                85                  90                  95

Glu Ile Leu Ser Glu Arg Arg Ala Asp Leu Glu Ala Phe Leu Gly
                100                 105                 110

Asn Arg Tyr Pro Ala Ser Thr Ile Pro Gln Ile Ala Arg Arg Leu Tyr
                115                 120                 125

Glu His Asn Arg Val Arg Leu Leu Val Asp Val Asn Tyr Thr Pro Val
            130                 135                 140

Pro Leu Gln Pro Arg Ile Ser Pro Leu Asn Gly Arg Asp Leu Asp Met
145                 150                 155                 160

Ser Leu Ser Cys Leu Arg Ser Met Ser Pro Val His Gln Lys Tyr Met
                165                 170                 175

Gln Asp Met Gly Val Gly Ala Thr Leu Val Cys Ser Leu Met Val Ser
                180                 185                 190

Gly Arg Leu Trp Gly Leu Ile Ala Cys His His Tyr Glu Pro Arg Phe
            195                 200                 205

Val Pro Phe His Ile Arg Ala Ala Gly Glu Ala Leu Ala Glu Thr Cys
        210                 215                 220

Ala Asn Arg Ile Ala Thr Leu Glu Ser Glu Asn Leu Tyr Phe Gln Ser
225                 230                 235                 240

Glu Phe Cys Glu Arg Glu Gln Ile His Leu Ala Gly Ser Ile Gln Pro
                245                 250                 255

His Gly Ile Leu Leu Ala Val Lys Glu Pro Asp Asn Val Val Ile Gln
            260                 265                 270

Ala Ser Ile Asn Ala Ala Glu Phe Leu Asn Thr Asn Ser Val Val Gly
        275                 280                 285

Arg Pro Leu Arg Asp Leu Gly Gly Asp Leu Pro Leu Gln Ile Leu Pro
    290                 295                 300

His Leu Asn Gly Pro Leu His Leu Ala Pro Val Thr Leu Arg Cys Thr
305                 310                 315                 320

Val Gly Ser Pro Pro Arg Arg Val Asp Cys Thr Ile His Arg Pro Ser
                325                 330                 335

Asn Gly Gly Leu Ile Val Glu Leu Glu Pro Ala Thr Lys Leu Glu Gly
            340                 345                 350

```
Gly Gly Ser Gly Gly Ser Glu Val Ser Ala Leu Glu Lys Glu Val Ser
            355                 360                 365
Ala Leu Glu Lys Glu Val Ser Ala Leu Glu Lys Glu Val Ser Ala Leu
        370                 375                 380
Glu Lys Glu Val Ser Ala Leu Glu Lys
385                 390
```

<210> SEQ ID NO 40
<211> LENGTH: 544
<212> TYPE: PRT
<213> ORGANISM: Artificial Sequence
<220> FEATURE:
<223> OTHER INFORMATION: (Amino acid sequence of iCAS3(+) 3.0)

<400> SEQUENCE: 40

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Ser Thr Thr Asn Ile Ala
    210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Val Arg Phe Asp Glu Glu Gly Asn Gly Glu
            260                 265                 270

Ile Leu Ser Glu Arg Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
    290                 295                 300

His Asn Arg Val Arg Leu Leu Val Asp Val Asn Tyr Thr Pro Val Pro
305                 310                 315                 320
```

-continued

```
Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
            340                 345                 350

Asp Met Gly Val Gly Ala Thr Leu Val Cys Ser Leu Met Val Ser Gly
        355                 360                 365

Arg Leu Trp Gly Leu Ile Ala Cys His His Tyr Glu Pro Arg Phe Val
    370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Gly Asp Glu Val Asp Gly Glu Phe
                405                 410                 415

Cys Glu Arg Glu Gln Ile His Leu Ala Gly Ser Ile Gln Pro His Gly
            420                 425                 430

Ile Leu Leu Ala Val Lys Glu Pro Asp Asn Val Val Ile Gln Ala Ser
        435                 440                 445

Ile Asn Ala Ala Glu Phe Leu Asn Thr Asn Ser Val Val Gly Arg Pro
    450                 455                 460

Leu Arg Asp Leu Gly Gly Asp Leu Pro Leu Gln Ile Leu Pro His Leu
465                 470                 475                 480

Asn Gly Pro Leu His Leu Ala Pro Met Thr Leu Arg Cys Thr Val Gly
                485                 490                 495

Ser Pro Pro Arg Arg Val Asp Cys Thr Ile His Arg Pro Ser Asn Gly
            500                 505                 510

Gly Leu Ile Val Glu Leu Glu Pro Ala Thr Lys Leu Glu Gly Gly Ser
        515                 520                 525

Arg Asp His Met Val Leu His Glu Tyr Val Asn Ala Ala Gly Ile Thr
    530                 535                 540

<210> SEQ ID NO 41
<211> LENGTH: 544
<212> TYPE: PRT
<213> ORGANISM: Artificial Sequence
<220> FEATURE:
<223> OTHER INFORMATION: (Amino acid sequence of iCAS3(+) 6.03)

<400> SEQUENCE: 41

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140
```

```
Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
                195                 200                 205

Lys Asp Pro Asn Glu Lys Gly Gly Ser Gly Ser Thr Thr Asn Ile Ala
            210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Gly Asn Ala Glu
            260                 265                 270

Ile Leu Ser Glu Arg Arg Arg Ala Asp Leu Glu Ala Phe Leu Gly Asn
                275                 280                 285

Arg Tyr Pro Ala Ser Thr Ile Pro Gln Ile Ala Arg Arg Leu Tyr Glu
            290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Val His Gln Lys Tyr Met Gln
                340                 345                 350

Asp Met Gly Val Gly Ala Thr Leu Val Cys Ser Leu Met Val Ser Gly
            355                 360                 365

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Asn Arg Ile Ala Thr Leu Glu Ser Gly Asp Glu Val Asp Gly Glu Phe
                405                 410                 415

Cys Glu Arg Glu Gln Ile His Leu Ala Gly Ser Ile Gln Pro His Gly
            420                 425                 430

Ile Leu Leu Ala Val Lys Glu Pro Asp Asn Val Val Ile Gln Ala Ser
                435                 440                 445

Ile Asn Ala Ala Glu Phe Leu Asn Thr Asn Ser Val Val Gly Arg Pro
450                 455                 460

Leu Arg Asp Leu Gly Gly Asp Leu Pro Leu Gln Ile Leu Pro His Leu
465                 470                 475                 480

Asn Gly Pro Leu His Leu Ala Pro Val Thr Leu Arg Cys Thr Val Gly
                485                 490                 495

Ser Pro Pro Arg Arg Val Asp Cys Thr Ile His Arg Pro Ser Asn Gly
            500                 505                 510

Gly Leu Ile Val Glu Leu Glu Pro Ala Thr Lys Leu Glu Gly Gly Ser
            515                 520                 525

Arg Asp His Met Val Leu His Glu Tyr Val Asn Ala Ala Gly Ile Thr
            530                 535                 540

<210> SEQ ID NO 42
<211> LENGTH: 392
```

<212> TYPE: PRT
<213> ORGANISM: Artificial Sequence
<220> FEATURE:
<223> OTHER INFORMATION: (Amino acid sequence of iCAS3(+) 6.031)

<400> SEQUENCE: 42

Met Gly Gly Ser Lys Val Ser Ala Leu Lys Glu Lys Val Ser Ala Leu
1               5                   10                  15

Lys Glu Lys Val Ser Ala Leu Lys Glu Lys Val Ser Ala Leu Lys Glu
            20                  25                  30

Lys Val Ser Ala Leu Lys Glu Gly Gly Ser Gly Ser Thr Thr Asn Ile
        35                  40                  45

Ala Pro Ala Leu Asp Gly Ala Phe His Arg Ile Thr Ser Ser Ser
    50                  55                  60

Leu Met Gly Leu Cys Asp Glu Thr Ala Thr Ile Ile Arg Glu Ile Thr
65                  70                  75                  80

Gly Tyr Asp Arg Val Met Val Val Arg Phe Asp Glu Glu Gly Asn Ala
                85                  90                  95

Glu Ile Leu Ser Glu Arg Arg Ala Asp Leu Glu Ala Phe Leu Gly
            100                 105                 110

Asn Arg Tyr Pro Ala Ser Thr Ile Pro Gln Ile Ala Arg Arg Leu Tyr
            115                 120                 125

Glu His Asn Arg Val Arg Leu Leu Val Asp Val Asn Tyr Thr Pro Val
130                 135                 140

Pro Leu Gln Pro Arg Ile Ser Pro Leu Asn Gly Arg Asp Leu Asp Met
145                 150                 155                 160

Ser Leu Ser Cys Leu Arg Ser Met Ser Pro Val His Gln Lys Tyr Met
                165                 170                 175

Gln Asp Met Gly Val Gly Ala Thr Leu Val Cys Ser Leu Met Val Ser
            180                 185                 190

Gly Arg Leu Trp Gly Leu Ile Ala Cys His His Tyr Glu Pro Arg Phe
        195                 200                 205

Val Pro Phe His Ile Arg Ala Ala Gly Glu Ala Leu Ala Glu Thr Cys
    210                 215                 220

Ala Asn Arg Ile Ala Thr Leu Glu Ser Gly Asp Glu Val Asp Gly Glu
225                 230                 235                 240

Phe Cys Glu Arg Glu Gln Ile His Leu Ala Gly Ser Ile Gln Pro His
                245                 250                 255

Gly Ile Leu Leu Ala Val Lys Glu Pro Asp Asn Val Ile Gln Ala
            260                 265                 270

Ser Ile Asn Ala Ala Glu Phe Leu Asn Thr Asn Ser Val Val Gly Arg
    275                 280                 285

Pro Leu Arg Asp Leu Gly Gly Asp Leu Pro Leu Gln Ile Leu Pro His
290                 295                 300

Leu Asn Gly Pro Leu His Leu Ala Pro Val Thr Leu Arg Cys Thr Val
305                 310                 315                 320

Gly Ser Pro Pro Arg Arg Val Asp Cys Thr Ile His Arg Pro Ser Asn
                325                 330                 335

Gly Gly Leu Ile Val Glu Leu Glu Pro Ala Thr Lys Leu Glu Gly Gly
            340                 345                 350

Gly Ser Gly Gly Ser Glu Val Ser Ala Leu Glu Lys Glu Val Ser Ala
        355                 360                 365

Leu Glu Lys Glu Val Ser Ala Leu Glu Lys Glu Val Ser Ala Leu Glu
    370                 375                 380

Lys Glu Val Ser Ala Leu Glu Lys
385                 390

<210> SEQ ID NO 43
<211> LENGTH: 546
<212> TYPE: PRT
<213> ORGANISM: Artificial Sequence
<220> FEATURE:
<223> OTHER INFORMATION: (Amino acid sequence of iNS3(+) 3.1)

<400> SEQUENCE: 43

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Ile Gly Lys Leu Thr Leu Lys Phe Ile Cys Thr
        35                  40                  45

Thr Gly Lys Leu Pro Val Pro Trp Pro Thr Leu Val Thr Thr Leu Thr
50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Lys Tyr Lys Thr Arg Ala Val Val Lys
            100                 105                 110

Phe Glu Gly Asp Thr Leu Val Asn Arg Ile Glu Leu Lys Gly Thr Asp
        115                 120                 125

Phe Lys Glu Asp Gly Asn Ile Leu Gly His Lys Leu Glu Tyr Asn Phe
130                 135                 140

Asn Ser His Asn Val Tyr Ile Thr Ala Asp Lys Gln Lys Asn Gly Ile
145                 150                 155                 160

Lys Ala Asn Phe Thr Val Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Thr Val Leu Ser Lys
        195                 200                 205

Asp Pro Asn Glu Lys Gly Gly Ser Gly Ser Thr Thr Asn Ile Ala Pro
210                 215                 220

Ala Leu Asp Gly Ala Phe His Arg Ile Thr Ser Ser Ser Leu Met
225                 230                 235                 240

Gly Leu Cys Asp Glu Thr Ala Thr Ile Ile Arg Glu Ile Thr Gly Tyr
                245                 250                 255

Asp Arg Val Met Val Val Arg Phe Asp Glu Glu Gly Asn Gly Glu Ile
            260                 265                 270

Leu Ser Glu Arg Arg Arg Ala Asp Leu Glu Ala Phe Leu Gly Asn Arg
        275                 280                 285

Tyr Pro Ala Ser Thr Ile Pro Gln Ile Ala Arg Arg Leu Tyr Glu His
290                 295                 300

Asn Arg Val Arg Leu Leu Val Asp Val Asn Tyr Thr Pro Val Pro Leu
305                 310                 315                 320

Gln Pro Arg Ile Ser Pro Leu Asn Gly Arg Asp Leu Asp Met Ser Leu
                325                 330                 335

Ser Cys Leu Arg Ser Met Ser Pro Ile His Gln Lys Tyr Met Gln Asp
            340                 345                 350

```
Met Gly Val Gly Ala Thr Leu Val Cys Ser Leu Met Ser Gly Arg
            355                 360                 365

Leu Trp Gly Leu Ile Ala Cys His His Tyr Glu Pro Arg Phe Val Pro
370                 375                 380

Phe His Ile Arg Ala Ala Gly Glu Ala Leu Ala Glu Thr Cys Ala Ile
385                 390                 395                 400

Arg Ile Ala Thr Leu Glu Ser Glu Asp Val Val Cys Cys Ser Met Ser
                405                 410                 415

Glu Phe Cys Glu Arg Glu Gln Ile His Leu Ala Gly Ser Ile Gln Pro
            420                 425                 430

His Gly Ile Leu Leu Ala Val Lys Glu Pro Asp Asn Val Val Ile Gln
        435                 440                 445

Ala Ser Ile Asn Ala Ala Glu Phe Leu Asn Thr Asn Ser Val Val Gly
    450                 455                 460

Arg Pro Leu Arg Asp Leu Gly Gly Asp Leu Pro Leu Gln Ile Leu Pro
465                 470                 475                 480

His Leu Asn Gly Pro Leu His Leu Ala Pro Met Thr Leu Arg Cys Thr
                485                 490                 495

Val Gly Ser Pro Pro Arg Arg Val Asp Cys Thr Ile His Arg Pro Ser
            500                 505                 510

Asn Gly Gly Leu Ile Val Glu Leu Glu Pro Ala Thr Lys Leu Glu Gly
        515                 520                 525

Gly Ser Arg Asp His Met Val Leu His Glu Tyr Val Asn Ala Ala Gly
    530                 535                 540

Ile Thr
545

<210> SEQ ID NO 44
<211> LENGTH: 546
<212> TYPE: PRT
<213> ORGANISM: Artificial Sequence
<220> FEATURE:
<223> OTHER INFORMATION: (Amino acid sequence of iNS3(+) 3.2)

<400> SEQUENCE: 44

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160
```

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
            195                 200                 205

Lys Asp Pro Asn Glu Lys Gly Gly Ser Gly Ser Thr Thr Asn Ile Ala
            210                 215                 220

Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Gly Asn Gly Glu
            260                 265                 270

Ile Leu Ser Glu Arg Arg Ala Asp Leu Glu Ala Phe Leu Gly Asn
            275                 280                 285

Arg Tyr Pro Ala Ser Thr Ile Pro Gln Ile Ala Arg Arg Leu Tyr Glu
            290                 295                 300

His Asn Arg Val Arg Leu Leu Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
                340                 345                 350

Asp Met Gly Val Gly Ala Thr Leu Val Cys Ser Leu Met Val Ser Gly
            355                 360                 365

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Glu Asp Val Val Cys Cys Ser Met
                405                 410                 415

Glu Phe Cys Glu Arg Glu Gln Ile His Leu Ala Gly Ser Ile Gln Pro
            420                 425                 430

His Gly Ile Leu Leu Ala Val Lys Glu Pro Asp Asn Val Val Ile Gln
            435                 440                 445

Ala Ser Ile Asn Ala Ala Glu Phe Leu Asn Thr Asn Ser Val Val Gly
450                 455                 460

Arg Pro Leu Arg Asp Leu Gly Asp Leu Pro Leu Gln Ile Leu Pro
465                 470                 475                 480

His Leu Asn Gly Pro Leu His Leu Ala Pro Met Thr Leu Arg Cys Thr
            485                 490                 495

Val Gly Ser Pro Pro Arg Arg Val Asp Cys Thr Ile His Arg Pro Ser
            500                 505                 510

Asn Gly Gly Leu Ile Val Glu Leu Glu Pro Ala Thr Lys Leu Glu Gly
            515                 520                 525

Gly Ser Arg Asp His Met Val Leu His Glu Tyr Val Asn Ala Ala Gly
530                 535                 540

Ile Thr
545

<210> SEQ ID NO 45
<211> LENGTH: 544
<212> TYPE: PRT

<213> ORGANISM: Artificial Sequence
<220> FEATURE:
<223> OTHER INFORMATION: (Amino acid sequence of iNS3(+) 3.3)

<400> SEQUENCE: 45

```
Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Ile Gly Lys Leu Thr Leu Lys Phe Ile Cys Thr
        35                  40                  45

Thr Gly Lys Leu Pro Val Pro Trp Pro Thr Leu Val Thr Thr Leu Thr
    50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Lys Tyr Lys Thr Arg Ala Val Val Lys
            100                 105                 110

Phe Glu Gly Asp Thr Leu Val Asn Arg Ile Glu Leu Lys Gly Thr Asp
        115                 120                 125

Phe Lys Glu Asp Gly Asn Ile Leu Gly His Lys Leu Glu Tyr Asn Phe
    130                 135                 140

Asn Ser His Asn Val Tyr Ile Thr Ala Asp Lys Gln Lys Asn Gly Ile
145                 150                 155                 160

Lys Ala Asn Phe Thr Val Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Thr Val Leu Ser Lys
        195                 200                 205

Asp Pro Asn Glu Lys Gly Gly Ser Gly Ser Thr Thr Asn Ile Ala Pro
    210                 215                 220

Ala Leu Asp Gly Ala Phe His Arg Ile Thr Ser Ser Ser Ser Leu Met
225                 230                 235                 240

Gly Leu Cys Asp Glu Thr Ala Thr Ile Ile Arg Glu Ile Thr Gly Tyr
                245                 250                 255

Asp Arg Val Met Val Val Arg Phe Asp Glu Gly Asn Gly Glu Ile
            260                 265                 270

Leu Ser Glu Arg Arg Arg Ala Asp Leu Glu Ala Phe Leu Gly Asn Arg
        275                 280                 285

Tyr Pro Ala Ser Thr Ile Pro Gln Ile Ala Arg Arg Leu Tyr Glu His
    290                 295                 300

Asn Arg Val Arg Leu Leu Val Asp Val Asn Tyr Thr Pro Val Pro Leu
305                 310                 315                 320

Gln Pro Arg Ile Ser Pro Leu Asn Gly Arg Asp Leu Asp Met Ser Leu
                325                 330                 335

Ser Cys Leu Arg Ser Met Ser Pro Ile His Gln Lys Tyr Met Gln Asp
            340                 345                 350

Met Gly Val Gly Ala Thr Leu Val Cys Ser Leu Met Val Ser Gly Arg
        355                 360                 365

Leu Trp Gly Leu Ile Ala Cys His His Tyr Glu Pro Arg Phe Val Pro
    370                 375                 380

Phe His Ile Arg Ala Ala Gly Glu Ala Leu Ala Glu Thr Cys Ala Ile
```

```
385                 390                 395                 400
Arg Ile Ala Thr Leu Glu Ser Glu Asp Val Val Cys Cys Ser Glu Phe
                405                 410                 415

Cys Glu Arg Glu Gln Ile His Leu Ala Gly Ser Ile Gln Pro His Gly
                420                 425                 430

Ile Leu Leu Ala Val Lys Glu Pro Asp Asn Val Val Ile Gln Ala Ser
                435                 440                 445

Ile Asn Ala Ala Glu Phe Leu Asn Thr Asn Ser Val Val Gly Arg Pro
450                 455                 460

Leu Arg Asp Leu Gly Gly Asp Leu Pro Leu Gln Ile Leu Pro His Leu
465                 470                 475                 480

Asn Gly Pro Leu His Leu Ala Pro Met Thr Leu Arg Cys Thr Val Gly
                485                 490                 495

Ser Pro Pro Arg Arg Val Asp Cys Thr Ile His Arg Pro Ser Asn Gly
                500                 505                 510

Gly Leu Ile Val Glu Leu Glu Pro Ala Thr Lys Leu Glu Gly Gly Ser
                515                 520                 525

Arg Asp His Met Val Leu His Glu Tyr Val Asn Ala Ala Gly Ile Thr
                530                 535                 540

<210> SEQ ID NO 46
<211> LENGTH: 547
<212> TYPE: PRT
<213> ORGANISM: Artificial Sequence
<220> FEATURE:
<223> OTHER INFORMATION: (Amino acid sequence of iCalpain(+) 1.0)

<400> SEQUENCE: 46

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
                20                  25                  30

Gly Glu Gly Asp Ala Thr Ile Gly Lys Leu Thr Leu Lys Phe Ile Cys
                35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
                100                 105                 110

Lys Phe Glu Gly Asp Thr Leu Val Asn Arg Ile Glu Leu Lys Gly Thr
                115                 120                 125

Asp Phe Lys Glu Asp Gly Asn Ile Leu Gly His Lys Leu Glu Tyr Asn
                130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Thr Val Leu Ser
                195                 200                 205

Lys Asp Pro Asn Glu Lys Gly Gly Ser Gly Ser Thr Thr Asn Ile Ala
```

```
                210                 215                 220
Pro Ala Leu Asp Gly Ala Phe His Arg Ile Thr Ser Ser Ser Ser Leu
225                 230                 235                 240

Met Gly Leu Cys Asp Glu Thr Ala Thr Ile Ile Arg Glu Ile Thr Gly
                245                 250                 255

Tyr Asp Arg Val Met Val Arg Phe Asp Glu Glu Gly Asn Gly Glu
            260                 265                 270

Ile Leu Ser Glu Arg Arg Ala Asp Leu Glu Ala Phe Leu Gly Asn
        275                 280                 285

Arg Tyr Pro Ala Ser Thr Ile Pro Gln Ile Ala Arg Arg Leu Tyr Glu
290                 295                 300

His Asn Arg Val Arg Leu Leu Val Asp Val Asn Tyr Thr Pro Val Pro
305                 310                 315                 320

Leu Gln Pro Arg Ile Ser Pro Leu Asn Gly Arg Asp Leu Asp Met Ser
                325                 330                 335

Leu Ser Cys Leu Arg Ser Met Ser Pro Ile His Gln Lys Tyr Met Gln
                340                 345                 350

Asp Met Gly Val Gly Ala Thr Leu Val Cys Ser Leu Met Val Ser Gly
            355                 360                 365

Arg Leu Trp Gly Leu Ile Ala Cys His His Tyr Glu Pro Arg Phe Val
370                 375                 380

Pro Phe His Ile Arg Ala Ala Gly Glu Ala Leu Ala Glu Thr Cys Ala
385                 390                 395                 400

Ile Arg Ile Ala Thr Leu Glu Ser Gln Gln Glu Val Tyr Gly Met Met
                405                 410                 415

Pro Arg Asp Cys Glu Arg Glu Gln Ile His Leu Ala Gly Ser Ile Gln
                420                 425                 430

Pro His Gly Ile Leu Leu Ala Val Lys Glu Pro Asp Asn Val Val Ile
            435                 440                 445

Gln Ala Ser Ile Asn Ala Ala Glu Phe Leu Asn Thr Asn Ser Val Val
450                 455                 460

Gly Arg Pro Leu Arg Asp Leu Gly Gly Asp Leu Pro Leu Gln Ile Leu
465                 470                 475                 480

Pro His Leu Asn Gly Pro Leu His Leu Ala Pro Met Thr Leu Arg Cys
                485                 490                 495

Thr Val Gly Ser Pro Pro Arg Arg Val Asp Cys Thr Ile His Arg Pro
            500                 505                 510

Ser Asn Gly Gly Leu Ile Val Glu Leu Glu Pro Ala Thr Lys Leu Glu
        515                 520                 525

Gly Gly Ser Arg Asp His Met Val Leu His Glu Tyr Val Asn Ala Ala
530                 535                 540

Gly Ile Thr
545

<210> SEQ ID NO 47
<211> LENGTH: 7
<212> TYPE: PRT
<213> ORGANISM: Artificial Sequence
<220> FEATURE:
<223> OTHER INFORMATION: (iTEV cleavage sequence)

<400> SEQUENCE: 47

Glu Asn Leu Tyr Phe Gln Ser
1               5
```

```
<210> SEQ ID NO 48
<211> LENGTH: 6
<212> TYPE: PRT
<213> ORGANISM: Artificial Sequence
<220> FEATURE:
<223> OTHER INFORMATION: (iCAS3 cleavage sequence)

<400> SEQUENCE: 48

Gly Asp Glu Val Asp Gly
1               5

<210> SEQ ID NO 49
<211> LENGTH: 9
<212> TYPE: PRT
<213> ORGANISM: Artificial Sequence
<220> FEATURE:
<223> OTHER INFORMATION: (iNS3 cleavage sequence)

<400> SEQUENCE: 49

Glu Asp Val Val Cys Cys Ser Met Ser
1               5

<210> SEQ ID NO 50
<211> LENGTH: 8
<212> TYPE: PRT
<213> ORGANISM: Artificial Sequence
<220> FEATURE:
<223> OTHER INFORMATION: (iNS3 cleavage sequence)

<400> SEQUENCE: 50

Glu Asp Val Val Cys Cys Ser Met
1               5

<210> SEQ ID NO 51
<211> LENGTH: 7
<212> TYPE: PRT
<213> ORGANISM: Artificial Sequence
<220> FEATURE:
<223> OTHER INFORMATION: (iNS3 cleavage sequence)

<400> SEQUENCE: 51

Glu Asp Val Val Cys Cys Ser
1               5

<210> SEQ ID NO 52
<211> LENGTH: 11
<212> TYPE: PRT
<213> ORGANISM: Artificial Sequence
<220> FEATURE:
<223> OTHER INFORMATION: (iCalpain cleavage sequence)

<400> SEQUENCE: 52

Gln Gln Glu Val Tyr Gly Met Met Pro Arg Asp
1               5                   10
```

GENETICALLY ENCODED INFRARED FLUORESCENT PROTEASE REPORTERS

CROSS-REFERENCES TO RELATED APPLICATIONS

This application is the U.S. National Phase of International Application No. PCT/US2015/024307 filed Apr. 3, 2015, which claims the benefit under 35 U.S.C. § 119(e) of U.S. Provisional Application No. 61/974,857 filed on Apr. 3, 2014, which are incorporated herein by reference in their entirety for all purposes.

GOVERNMENT SUPPORT

This invention was made with government support under Grant No. GM105446 awarded by the National Institutes of Health. The government has certain rights in the invention.

FIELD OF THE INVENTION

This invention relates the rational design of genetically encoded infrared fluorescent protease sensors.

BACKGROUND OF THE INVENTION

Human genome contains ~600 proteases and homologs, similar to the number of protein kinases (~500). Proteases are initially described as destructive enzymes that recycle proteins into amino acids. After many years of study, our understanding of protease function has shifted from the nonspecific degradative function to specific proteolytic reactions that regulate protein trafficking, localization, activity and interaction with other proteins, and cleave and activate pro-hormones and peptide neurotransmitter precursors. Proteases therefore regulate many biological processes, including basic molecular processes such as DNA replication and transcription, unfolded protein response and protein degradation; cellular processes such as cell differentiation, proliferation and programmed cell death; tissue morphogenesis and homeostasis such as angiogenesis, neurogenesis, blood coagulation and wound repair. It is thus not surprising that changes to proteolytic systems lead to many diseases including cancer, neurodegenerative and cardiovascular diseases. Many pathogens and viruses also utilize proteases for their invasion and replication in host. In short, proteases play important roles in the development and homeostasis of all living organisms, and are important drug targets.

In view of the important role of proteases, it would be beneficial to monitor, track, and image protease activity. Moreso, it would be ideal to monitor, track, and image protease activity in vivo. One such approach is the design of a protease reporter wherein the protease reporter becomes fluorescent only when activated by a protease. However, there are limitations to the use of known fluoresecent reporters.

For example, although the availability of a wide variety of naturally occurring fluorescent proteins and spectral variants of the proteins has allowed for substantial advances, limitations to the use of fluorescent proteins remain. In particular, the use of fluorescent proteins in intact animals such as mice has been hindered by poor penetration of excitation light. For example, visibly fluorescent proteins have been cloned from jellyfish and corals and have revolutionized many areas of molecular and cell biology through in vivo expression, in vitro expression, protein labeling, and protein engineering; however, the use of such fluorescent proteins for imaging studies in intact animals (e.g., a mouse or human) is limited due to the excitation and emission maxima of the fluorescent proteins.

Specifically, the excitation and emission maxima of these fluorescent proteins generally do not exceeded 598 and 655 nm respectively (D. Shcherbo et al., Nat. Methods 4, 741 (2007); M. A. Shkrob et al., Biochem. J. 392, 649 (2005); L. Wang, W. C. Jackson, P. A. Steinbach, R. Y. Tsien, Proc. Natl. Acad. Sci. U.S.A. 101, 16745 (2004)). One exception are the phytochrome-based fluorescent proteins that have an excitation maximum of 644 nm and an emission maximum of 672 nm (A. J. Fischer, J. C. Lagarias, Proc. Natl. Acad. Sci. U.S.A. 101, 17334 (2004)). However, neither the traditional fluorescent protein cloned from marine animals or the phytochrom-based fluorescent proteins are well equipped for in vivo imaging in whole, living animals.

For example, Green Fluorsecent Proteins are commonly used in fluorescent reporter assays. GFPs are involved in bioluminescence in a variety of marine invertebrates, including jellyfish such as *Aequorea Victoria* (Morise, H., et al., Biochemistry 13:2656-2662 (1974); Prendergast, F. G., and Mann, K. G., Biochemistry 17:3448-3453 (1978); Ward, W. W., Photochem. Photobiol. Rev. 4:1-57 (1979) and the sea pansy *Renilla reniformis* (Ward, W. W., and Cormier, M. J., Photochem. Photobiol. 27:389-396 (1978); Ward, W. W., et al., Photochem. Photobiol. 31:611-615 (1980)). The GFP isolated from *A. victoria* has been cloned and the primary amino acid structure has been deduced. The chromophore of *A. victoria* GFP is a hexapeptide composed of amino acid residues 64-69 in which the amino acids at positions 65-67 (serine, tyrosine and glycine) form a heterocyclic ring (Prasher, D. C., et al., Gene 111:229-233 (1992); Cody, C. W., et al., Biochemistry 32:1212-1218 (1993)). Resolution of the crystal structure of GFP has shown that the chromophore is contained in a central α-helical region surrounded by an 11-stranded β-barrel (Ormo, M., et al., Science 273:1392-1395 (1996); Yang, F., et al., Nature Biotech. 14:1246-1251 (1996)). Upon purification, native GFP demonstrates an absorption maximum at 395 nm and an emission maximum at 509 nm (Morise, H., et al., Biochemistry 13:2656-2662 (1974); Ward, W. W., et al., Photochem. Photobiol. 31:611-615 (1980)) with exceptionally stable and virtually non-photobleaching fluorescence (Chalfie, M., et al., Science 263:802-805 (1994)).

GFP has been used as a fluorescent label in protein localization and conformation studies and has been used as a reporter gene in transfected prokaryotic and eukaryotic cells (Heim, R., et al., Proc. Natl. Acad. Sci. USA 91:1250-1254 (1994); Yokoe, H., and Meyer, T., Nature Biotech. 14:1252-1256 (1996); Chalfie, M., et al., Science 263:802-805 (1994); Wang, S., and Hazelrigg, T., Nature 369:400-403 (1994)). GFP has also been used in fluorescence resonance energy transfer studies of protein-protein interactions (Heim, R., and Tsien, R. Y., Curr. Biol. 6:178-182 (1996)). Since GFP is naturally fluorescent, exogenous substrates and cofactors are not necessary for induction of fluorescence. Furthermore, the GFP cDNA containing the complete coding region is less than 1 kb and is easily manipulated and inserted into a variety of vectors for use in creating stable transfectants (Chalfie, M., et al., Science 263:802-805 (1994)). However, despite the relative ease at expressing the GFPs, they offer limited use for studying protease activity in vivo.

In vivo optical imaging of deep tissues in animals is most feasible between 650 and 900 nm because such wavelengths minimize the absorbance by hemoglobin, water, and lipids as well as light scattering (F. F. Jobsis, Science 198, 1264

(1977)); R. Weissleder and V. Ntziachristos, *Nat. Med.* 9, 123 (2003)). Accordingly, the emission maximum of 598 and the absorption maximum of 655 nm of traditional fluorescent proteins (e.g., fluorescent proteins cloned from jellyfish and corals) are ineffective at in vivo optical imaging of deep tissues in animals. Thus, genetically encoded, infrared fluorescent proteins (IFPs) are particularly valuable for whole-body imaging in cancer, stem cell biology, gene therapy, and other areas of biomedical research and treatment.

Furthermore, although many protease-activity based chemical dyes have been developed and applied to the study of disease models, these non-genetically encoded fluorophores are very difficult, if not impossible, to be used in the study of animal development. The fluorescence resonance energy transfer (FRET)-based reporters using GFP and derivatives have been successfully used in detecting protease activity with spatiotemporal resolution in cultured cells. However, the signal of these FRET reporters is weak (several to several tens percent change), which is very challenging in imaging protease activity in animals, due to tissue auto-fluorescence in the visible-wavelength region, cellular heterogeneity and three-dimensional architecture in tissues. It is thus not surprising that FRET sensors are rarely used in whole-animal imaging.

To overcome this problem, other mechanism based reporters have been developed, such as those based on degradation signal or aggregation motif. However, these biological mechanism based reporters are highly dependent on cellular context. For example, the GFP aggregation-based reporter achieves ~50 fold signal gain in *E. coli*, but its signal is significantly decreased to only ~1-3 fold change in mammalian cells [Nicholls, S. B., Chu, J., Abbruzzese, G., Tremblay, K. D., and Hardy, J. A. (2011). Mechanism of a Genetically Encoded Dark-to-Bright Reporter for Caspase Activity. J Biol Chem 286, 24977-24986]. Therefore, a protease reporter based on physical/chemical mechanism would be ideal for its robust use in animals.

In addition the protease reporter being based on a physical/chemical mechanism, an ideal reporter should not be fluorescent until activated by its protease. The novel genetically encoded iProtease described herein is thus an ideal protease reporter, not only because it overcomes the limitations of previously reported chemical dyes and genetically encoded reporters, it is also because its infrared fluorescence is optimized for whole-animal imaging. The rationally designed iProtease provides a general scaffold for further design of many if not all proteases with specific proteolytic activity, and opens opportunity in the study of proteases in animal development and disease. It can also be used in drug development under biological context.

BRIEF SUMMARY OF THE INVENTION

Accordingly, the present invention provides a variant polypeptide of a parent polypeptide, where the variant polypeptide comprises at least 90% identity to an amino acid sequence selected from the group comprising SEQ ID NOS:24-46.

In a further embodiment and in accordance with the above, the variant polypeptide has at least 95% identity to an amino acid sequence selected from the group comprising SEQ ID NOS:24-46.

In a still further embodiment and in accordance with any of the above, the variant polypeptide includes an amino acid sequence selected from the group comprising SEQ ID NOS:24-46.

In one aspect, the present invention provides an isolated polynucleotide encoding a polypeptide with at least 90% identity to a nucleic acid sequence selected from the group comprising SEQ ID NOS:1-23.

In a further embodiment and in accordance with the above, the isolated polynucleotide has at least 95% identity to a nucleic acid sequence selected from the group comprising SEQ ID NOS:1-23.

In a still further embodiment and in accordance with any of the above, the isolated polynucleotide includes a nucleic acid sequence selected from the group comprising SEQ ID NOS:1-23.

In a still further embodiment and in accordance with any of the above, the present invention provides a vector comprising the polynucleotide sequence of any of SEQ ID NOS: 1-23.

In a still further embodiment and in accordance with any of the above, the present invention provides a host cell comprising the vector comprising any of the above polynucleotide sequences.

In a still further embodiment and in accordance with any of the above, the present invention provides a kit comprising any of the above described polynucleotides.

In a further aspect, the present invention provides a method of in vivo optical imaging, the method comprising the step of: expressing in a cell a polynucleotide encoding a first protein, the first protein comprising a protein encoded by a polynucleotide of any of the polynucleotides described above. In a further embodiment, the cell is a bacterial or mammalian cell. In a still further embodiment, the in vivo imaging is performed in a living animal. In a yet further embodiment, the animal is a human.

In a further aspect, the present invention provides a method of detecting protease activity, the method comprising expressing a polypeptide according to any of those described above in a cell, wherein the polypeptide is cleaved in the presence of a protease and wherein the polypeptide emits infrared fluorescence upon cleavage. In a further embodiment, the polypeptide is selected from the group consisting of SEQ ID NOS: 24-39 and the protease is a tobacco etch virus protease. In a still further embodiment, the polypeptide is selected from the group consisting of SEQ ID NOS: 40-42 and the protease is a caspase protease. In a yet further embodiment, the caspase protease is a caspase 3 protease or a caspase 7 protease. In a further embodiment, the polypeptide is selected from the group consisting of SEQ ID NOS: 43-45 and the protease is a Hepatitis C NS3 protease. In a still further embodiment, the polypeptide is SEQ ID NO:46 and the protease is a calpain protease.

In a further aspect, the present invention provides a method of making an infrared fluorescent protease reporter from an infrared protein (IFP) comprising: a. making a circular permutation to the IFP wherein the original N- and C-termini are linked together by a protease cleavage sequence, b. cutting the sequence between the PAS and GAF domains to create new N- and C-termini such that the C-terminus is on the PAS domain and the N-terminus is on the GAF domain, c. adding a split GFP to the new N- and C-termini, d. and truncating the original N- and C-termini so that the distance between the catalytic cysteine and the carboxyl end of the GAF is larger than the length of protease cleavage sequence. In a further embodiment, the infrared fluorescent protease reporter has an amino acid sequence that is at least 90% identical to an amino acid sequence selected from the group consisting of SEQ ID NOS:24-46. In a still further embodiment, the infrared fluorescent protease reporter has an amino acid sequence that is at least 95% identical to an amino acid sequence selected from the group consisting of SEQ ID NOS:24-46. In a still further embodiment, the infrared fluorescent protease reporter has an amino acid sequence selected from the group consisting of SEQ ID NOS:24-46.

In a further aspect, the present invention provides a method of detecting apoptosis, the method comprising expressing an infrared fluorescent protease reporter that has an amino acid sequence of that is at least 90% identical to an amino acid sequence selected from the group consisting of SEQ ID NOS:40-42 in a cell, wherein the infrared fluorescent protease reporter fluoresces in response to the activation of apoptosis. In a further embodiment, the infrared fluorescent protease reporter has an amino acid sequence that is at least 95% identical to an amino acid sequence selected from the group consisting of SEQ ID NOS:40-42. In a still further embodiment, the infrared fluorescent protease reporter has an amino acid sequence selected from the group consisting of SEQ ID NOS:40-42.

In a further aspect, the present invention provides a method of detecting the efficacy of a therapy designed to induce apoptosis comprising: a. administering an infrared fluorescent protease reporter that has an amino acid sequence of that is at least 90% identical to an amino acid sequence selected from the group consisting of SEQ ID NOS:40-42 to a subject; b. detecting the infrared fluorescence of the infrared fluorescent protease reporter, c. administering an apoptosis-inducing drug to the subject, d. detecting the infrared fluorescence of the infrared fluorescent protease reporter after the administration of the apoptosis-inducing drug, wherein an increase in infrared fluorescence is indicative of increased apopositis and the efficacy of the apoptosis-inducing drug. In a further embodiment, the infrared fluorescent protease reporter has an amino acid sequence that is at least 95% identical to an amino acid sequence selected from the group consisting of SEQ ID NOS:24-46. In a still further embodiment, the infrared fluorescent protease reporter has an amino acid sequence selected from the group consisting of SEQ ID NOS:24-46. In a yet further embodiment, the apopotosis-inducing drug is administered to treat a proliferative disorder. In a further embodiment, the apopotosis-inducing drug is administered to treat cancer.

In a further aspect, the present invention provides a method of detecting calpain activity, the method comprising expressing an infrared fluorescent protease reporter that has an amino acid sequence of that is at least 90% identical to an amino acid sequence of SEQ ID NO:46 in a cell, wherein the infrared fluorescent protease reporter fluoresces in response to the activation of apoptosis. In a further embodiment, the infrared fluorescent protease reporter has an amino acid sequence that is at least 95% identical to amino acid sequence of SEQ ID NO:46. In a yet further embodiment, the infrared fluorescent protease reporter has an amino acid sequence of SEQ ID NO:46.

In a further aspect, the present invention provides a method of detecting the efficacy of a therapy designed to inhibit calpain activity comprising: a. administering an infrared fluorescent protease reporter that has an amino acid sequence of that is at least 90% identical to an amino acid sequence of SEQ ID NO:46; b. detecting the infrared fluorescence of the infrared fluorescent protease reporter, c. administering calpain inhibitor to the subject, d. detecting the infrared fluorescence of the infrared fluorescent protease reporter after the administration of the calpain inhibitor, wherein decrease in infrared fluorescence is indicative of decreased calpain activity and efficacy of the calpain inhibitor. In a further embodiment, the infrared fluorescent protease reporter that has an amino acid sequence of that is at least 95% identical to amino acid sequence of SEQ ID NO:46. In a still further embodiment, the infrared fluorescent protease reporter that has an amino acid sequence of SEQ ID NO:46. In a yet further embodiment, the calpain inhibitor is administered to treat a proliferative disorder. In a further embodiment, the calpain inhibitor is administered to treat cancer. In a still further embodiment the calpain is calpain 1 or calpain 2.

BRIEF DESCRIPTION OF THE DRAWINGS

FIG. 1A shows the modeled structure of the monomeric infrared fluorescent protein (mIFP). The PAS and GAF domains are shown in cyan and yellow, respectively. The catalytic cysteine and the chromophore (biliverdin, abbreviated as BV) are shown in red and purple, respectively. FIG. 1B shows the strategy for rational design of iProtease. mIFP is shown by the cartoon (BV in purple, cysteine in orange). The dashed line represents protease cleavage sequence. The large and small green boxes represent amino (N) and carboxyl (C) part of split GFP. Steps of the design (1-3): 1, Circular permutation; 2, Adding N- and C-part of the split GFP; 3, Truncation at the old N and C terminus of mIFP; 4, Protease cleavage (activation). The "inactive" (i.e. uncleaved) iProtease is only green fluorescent; the "active" (i.e. cleaved) iProtease is both green and infrared fluorescent. FIG. 1C shows the proof of principle: infrared fluorescent TEV protease sensor (iTEV) using TEV specific cleavage sequence (ENLYFQS). Mammalian cells (HEK293) express: 1) iTEV (top); 2) iTEV and TEV protease (bottom).

Figures 1A, 1B, 1C:
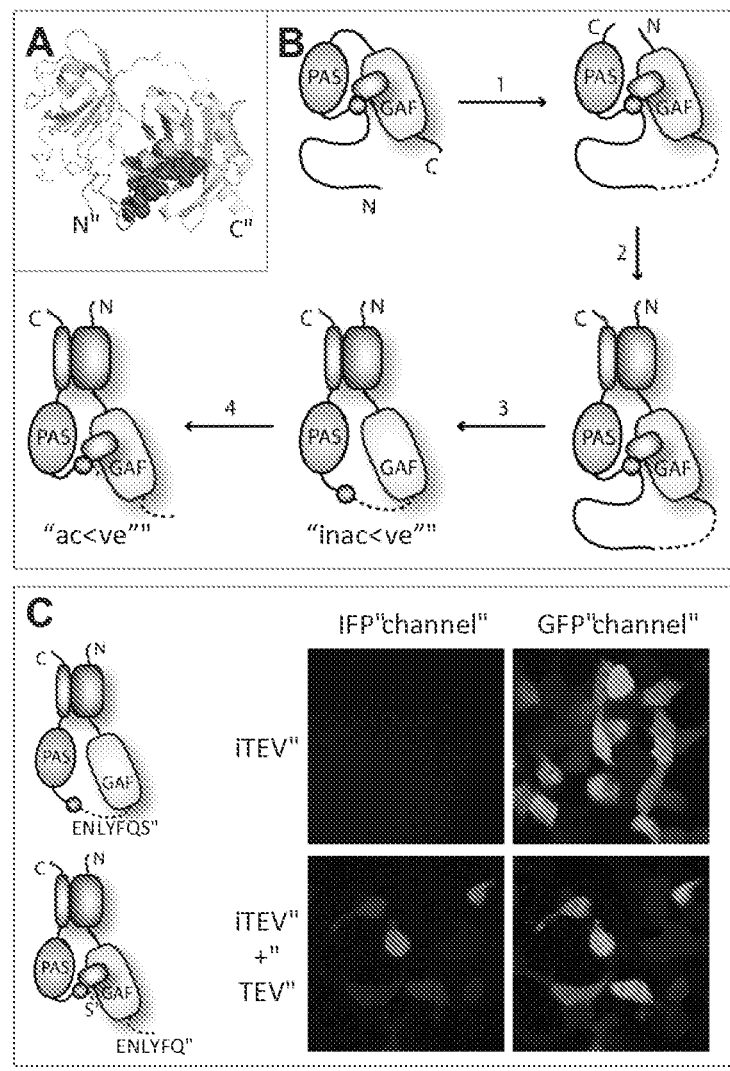
FIG. 1A-FIG. 1C show the rational design of genetically encoded infrared fluorescent protease sensor (iProtease).

The design provided in FIGS. 1A-1C is general and can be used to design any protease sensors. Two nonlimiting examples of protease sensors are described herein: TEV protease and caspase-3.

Figures 2A, 2B, 2C, 2D, 2E, 2F, 2G, 2H:
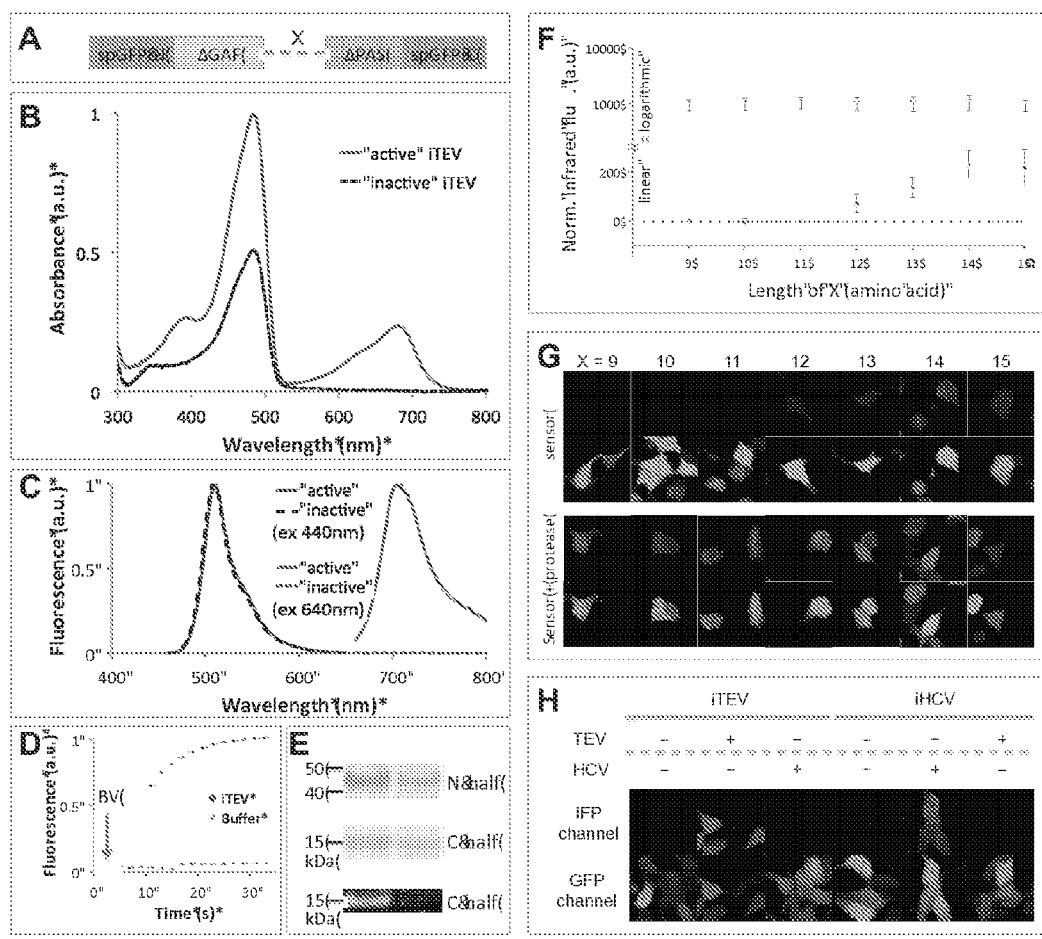

FIG. 2A-FIG. 2H shows the characterization of iProtease. FIG. 2A shows the absorbance spectra of the "active" and "inactive" iTEV. Note: "active" iTEV was prepared by purifying iTEV from the mixture of iTEV, TEV and BV; "inactive" iTEV was prepared by purifying iTEV from the mixture of iTEV and BV. The "inactive" iTEV is normalized to 0.5 so that its spectrum does not overlap with that of "active" iTEV. FIG. 2B shows the absorbance spectra of the "active" and "inactive" iTEV. Note: "active" iTEV was prepared by purifying iTEV from the mixture of iTEV, TEV and BV; "inactive" iTEV was prepared by purifying iTEV from the mixture of iTEV and BV. The "inactive" iTEV is normalized to 0.5 so that its spectrum does not overlap with that of "active" iTEV. FIG. 2C shows the emission spectra of "active" and "inactive" iTEV upon excitation at 440 or 640 nm. (-) Emission spectra of "active" iTEV excited at 440 nm; (---) Emission spectra of "inactive" iTEV excited at 440 nm; (-) Emission spectra of "active" iTEV excited at 640 nm; (---) Emission spectra of "inactive" iTEV excited at 640 nm. FIG. 2D shows the chromophore binding kinetics: infrared fluorescence monitored over time (second) upon adding BV to the activated iTEV (i.e. iTEV that was purified from the mixture of iTEV and TEV in the absence of BV. FIG. 2E shows the Coomassie blue staining and zinc-induced fluorescence assay (bottom) of the "active" (first row) and activated (second row) iTEV. FIG. 2F shows the normalized (by GFP) infrared fluorescence of iTEV (X=9) and its derivatives (X=10 to 15) plotted against the length X. The red and blue squares correspond to cells expressing the sensor and the sensor plus protease, respectively. The dashed line has Y-axis value 0 (i.e. zero infrared fluorescence). FIG. 2G shows representative images of mammalian cells (HEK293) expressing the iTEV and its derivatives as in F. First and second row: IFP and GFP channel of cells expressing the sensor only. Third and fourth row: IFP and GFP channel of cells expressing both the sensor and protease. FIG. 2H shows the specificity of iProtease: HEK293 cells expressing the iTEV with co-expression of TEV protease or the Hepatitis C Virus NS3/4A protease (HCV); or HEK293 cells expressing the HCV NS3/4A protease sensor (iHCV) with co-expression of the NS3/4A protease or TEV protease.

Figures 3A, 3B, 3C:
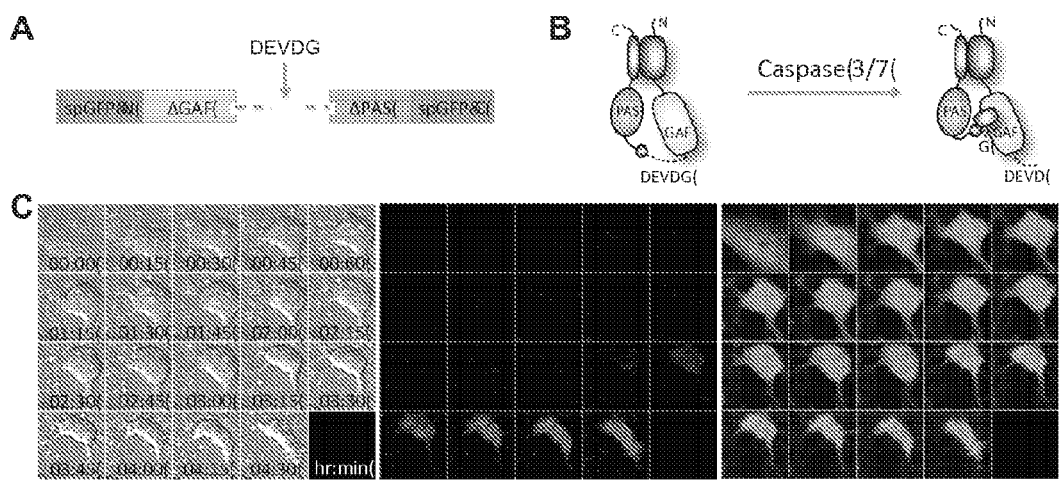

FIG. 3A-FIG. 3C show the genetically encoded infrared fluorescent executioner-caspase reporter (iCasper). FIG. 3A shows the construction of iCasper. FIG. 3B shows a cartoon of the cleavage and activation of iCasper. FIG. 3C shows time lapse images of human glioblastoma cells LN229 expressing iCasper upon addition of 1 uM Staurosporin. Left: DIC; middle: IFP channel; right: GFP channel.

Figure 4:
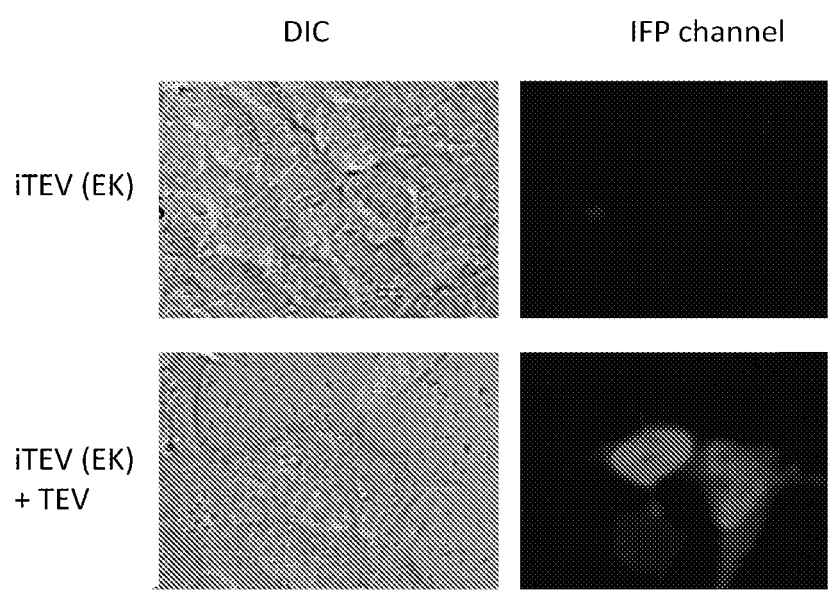

FIG. 4 shows the genetically encoded infrared fluorescent protease sensor using heterodimeric coiled coils instead of split GFP. HEK293 cells were transfected with the iTEV (EK) sensor without (top two panels) or with (bottom two panels) TEV protease.

Figure 5:
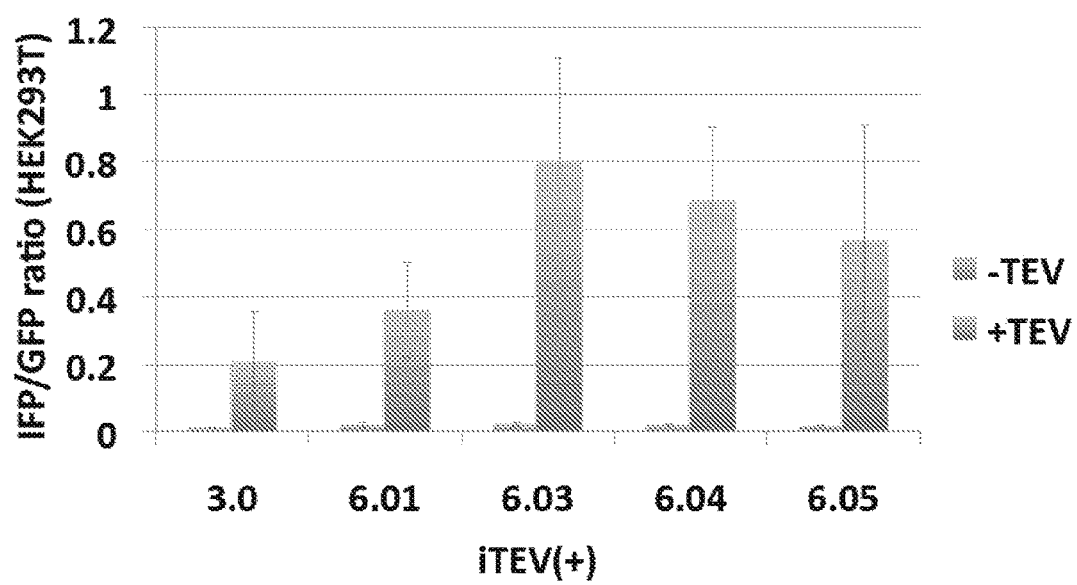

FIG. 5 shows the IFP/GFP ratios of iTEV and iTEV mutants (iTEV(+) 6.01, iTEV(+) 6.03, iTEV(+) 6.04, and iTEV(+) 6.05) expressed in Human Embryonic Kidney (HEK293T) cells in the presence (TEV+) or absence (TEV−) of TEV protease. As shown in the graph of FIG. 5, the cells increased in infrared fluorescence in the presence of TEV, demonstrating that the subject iTEVs disclosed herein can be activated by TEV protease.

DETAILED DESCRIPTION OF THE INVENTION

Introduction

GFP and its red homologs are powerful tools for cell and molecular biology (Day, R. N. & Davidson, M. W. The fluorescent protein palette: tools for cellular imaging. *Chem Soc Rev* 38, 2887-2921 (2009); Tsien, R. Y. Constructing and exploiting the fluorescent protein paintbox (Nobel Lecture). *Angew Chem Int Ed Engl* 48, 5612-5626 (2009)). Through protein engineering, these fluorescent proteins (FPs) now cover UV-visible spectrum every ~30 nm from 400 to 600 nm (excitation maxima) (Kremers, G. J., Gilbert, S. G., Cranfill, P. J., Davidson, M. W. & Piston, D. W. Fluorescent proteins at a glance. *Journal of Cell Science* 124, 2676-2676 (2011)). They have been widely used in multicolor protein labeling in living cells, which enables study of spatiotemporal dynamics of multiple proteins and protein-protein interactions (Sakaue-Sawano, A. et al. Visualizing Spatiotemporal Dynamics of Multicellular Cell-Cycle Progression. *Cell* 132, 487-498 (2008)). They have also been used in developing other technologies such as genetically encoded Forster (or fluorescence) resonance energy transfer (FRET) for reporting activities of an enzyme such as kinase (Zhang, J., Hupfeld, C. J., Taylor, S. S., Olefsky, J. M. & Tsien, R. Y. Insulin disrupts beta-adrenergic signalling to protein kinase A in adipocytes. *Nature* 437, 569-573 (2005); Wang, Y. et al. Visualizing the mechanical activation of Src. *Nature* 434, 1040-1045 (2005)), and monitoring small signaling molecules such as calcium and cAMP (Miyawaki, A. et al. Fluorescent indicators for Ca2+ based on green fluorescent proteins and calmodulin. *Nature* 388, 882-887 (1997); Zaccolo, M. Discrete Microdomains with High Concentration of cAMP in Stimulated Rat Neonatal Cardiac Myocytes. *Science* 295, 1711-1715 (2002)).

Recently, this FP palette has been extended into the near-infrared region by the introduction of bacterial phytochrome-derived IFPs of which the scaffold is different from the β-can fold of GFP (Shu, X. et al. Mammalian expression of infrared fluorescent proteins engineered from a bacterial phytochrome. *Science* 324, 804-807 (2009); Filonov, G. S. et al. Bright and stable near-infrared fluorescent protein for in vivo imaging. *Nat Biotechnol* 29, 757-761 (2011)).

Recently, infrared fluorescent proteins (IFPs) have been engineered from bacterial phytochromes (BphPs), which belong to the phytochrome (Phy) red/far-red photoreceptor superfamily (Giraud, E. & Verméglio, A. Bacteriophytochromes in anoxygenic photosynthetic bacteria. *Photosyn Res* 97, 141-153 (2008)). In addition to BphPs, the Phy superfamily also includes plant phytochromes (Phys), cyanobacterial phytochromes (Cphs) and fungal phytochromes (Fphs) (Karniol, B., Wagner, J. R., Walker, J. M. & Vierstra, R. D. Phylogenetic analysis of the phytochrome superfamily reveals distinct microbial subfamilies of photoreceptors. *Biochem J* 392, 103 (2005)).

The Phy superfamily utilizes a covalently bound tetrapyrrole bilin to sense red and far-red, which allows the organism to adapt to changes of light environment. BphPs use a linear tetrapyrrole bilin, biliverdin (BV), which is a catabolic metabolite of heme by heme oxygenase. BphPs are composed of an N-terminal PAS domain, followed by GAF domain and PHY domain, and a signal transduction domain at C-terminus that is often a histidine kinase. BphPs contain intrinsic lyase activity and therefore they autocatalytically incorporate the bilin chromophore. BV binds to GAF domain non-covalently and forms a thioether bond between its A-ring vinyl group and a conserved cysteine at N-terminus (Wagner, J. R., Brunzelle, J. S., Forest, K. T. & Vierstra, R. D. A light-sensing knot revealed by the structure of the chromophore-binding domain of phytochrome. *Nature* 438, 325-331 (2005)).

Upon light excitation the D-ring of BV rotates, resulting in a conformational change of the protein and leads to activation of histidine kinase (Yang, X., Ren, Z., Kuk, J. & Moffat, K. Temperature-scan cryocrystallography reveals reaction intermediates in bacteriophytochrome. *Nature* 479, 428-432 (2011)). This kinase activation results in changes of gene expression, which allows optimal development of bacteria according to the light environment (Giraud, E. & Verméglio, A. Bacteriophytochromes in anoxygenic photosynthetic bacteria. *Photosyn Res* 97, 141-153 (2008)). This biological function suggests that BphPs are highly efficient at non-radiative decay of its excited state, and therefore the radiative decay efficiency is negligible. In other words, BphPs are probably optimized through evolution to be non-fluorescent.

IFPs are composed of the N-terminal PAS and GAF domains of BphPs, and autocatalytically incorporate the chromophore biliverdin (BV). BV is a catabolic metabolite of heme by heme oxygenase and is non-fluorescent by itself. BV binds to the GAF domain non-covalently and forms a thioether bond with a conserved cysteine at N-terminus of IFPs (FIG. 1A) (Wagner, J. R., Brunzelle, J. S., Forest, K. T. & Vierstra, R. D. A light-sensing knot revealed by the structure of the chromophore-binding domain of phytochrome. *Nature* 438, 325-331 (2005)).

BphP-derived IFPs can provide an orthogonal color to GFP and its red homologs in protein labeling. As a protein fusion tag, FP has to be monomeric so that it will not perturb the stoichiometry of the protein of interest. However, most Phys including BphPs function as multimeric complexes through oligomeric interaction at the N-terminal photosensory core domain (PAS-GAF-PHY) or at the C-terminal module (Giraud, E. & Verméglio, A. Bacteriophytochromes in anoxygenic photosynthetic bacteria. *Photosyn Res* 97, 141-153 (2008)). Both IFP1.4 and iRFP were derived from dimeric BphPs.

The invention described herein discloses the novel design of infrared fluorescent protease reporter that becomes fluorescent only when activated by a protease. Specifically, a naturally-monomeric IFP (mIFP) was engineered so that its chromophore incorporation is regulated by protease activity.

Definitions

Unless specifically indicated otherwise, all technical and scientific terms used herein have the same meaning as commonly understood by those of ordinary skill in the art to which this invention belongs. In addition, method or materials that are substantially equivalent to a method or material described herein can be used in the practice of the present invention. For purposes of the present invention, the following terms are defined.

"A" or "the" as used herein not only includes aspects with one member, but also includes aspects with more than one member. For example, an embodiment including "an IFP" should be understood to present certain aspects with two or more IFPs.

"Or" as used herein should in general be construed non-exclusively. For example, an embodiment of "a variant phytochrome comprising the mutations E158V, A185S, or I203N" would typically present aspects with any one, two, or all three of the mutations.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, "patient" or "subject" refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient." In preferred embodiments, a patient is a human.

The term "phytochrome" refers to a class of plant- and bacteria-derived proteins. Naturally occurring, non-mutant phytochromes generally absorb in the red portion of the visible spectrum. "Bacteriophytochrome" refers to a phytochrome derived from bacteria.

The term "isolated" as used herein with respect to nucleic acids, such as DNA or RNA, refers to molecules separated from other DNAs, or RNAs, respectively that are present in the natural source of the macromolecule. Isolated is meant to include nucleic acid fragments which are not naturally occurring as fragments and would not be found in the natural state. The term isolated as used herein also refers to a nucleic acid or peptide that is substantially free of cellular material, viral material, or culture medium when produced by recombinant DNA techniques, or chemical precursors, or other chemicals when chemically synthesized.

More broadly, the term "isolated" or "purified" refers to a material that is substantially or essentially free from other components that normally accompany the material in its native state in nature. Purity or homogeneity generally are determined using analytical chemistry techniques such as polyacrylamide gel electrophoresis, high-performance liquid chromatography (HPLC), and the like. A polynucleotide or a polypeptide is considered to be isolated when it is the predominant species present in a preparation. Generally, an isolated protein or nucleic acid molecule represents greater than 50% of the macromolecular species present in a preparation, usually represents greater than 80% or 90% of all macromolecular species present, often represents greater than 95%, of the macromolecular species, and, in particular, may be a polypeptide or polynucleotide that purified to essential homogeneity such that it is the only species detected when it is examined using conventional methods for determining the purity of such a molecule.

The term "naturally occurring" is used to refer to a protein, nucleic acid molecule, cell, or other material that exists in the natural world, for example, a polypeptide or polynucleotide sequence that is present in an organism, including in a virus. In general, at least one instance of a naturally occurring material existed in the world prior to its creation, duplication, or identification by a human. A naturally occurring material can be in its form as it exists in the natural world, or can be modified by the hand of man such that, for example, it is in an isolated form.

The term "nucleic acid" or "polynucleotide" refers to deoxyribonucleotides or ribonucleotides and polymers thereof in either single- or double-stranded form, and complements thereof. The term refers to all forms of nucleic acids (e.g., gene, pre-mRNA, mRNA) and their polymorphic variants, alleles, mutants, and interspecies homologs. The term nucleic acid is used interchangeably with gene, cDNA, mRNA, oligonucleotide, and polynucleotide. The term encompasses nucleic acids that are naturally occurring or recombinant. Nucleic acids can (1) code for an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence.

Relating specifically to the non-naturally occurring IFPs described herein, the term "polynucleotide" includes, but is not limited to, cDNA and RNA.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N terminal end or the C-terminal end. Truncated versions of nucleic acid or polypeptide sequences can be naturally occurring or recombinantly created.

Nucleic acids can contain known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein variant of the invention linked to a polypeptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced there from, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

An expression control sequence refers to a nucleotide sequence that regulates the transcription or translation of a polynucleotide or the localization of a polypeptide to which it is operatively linked Expression control sequences are "operatively linked" when the expression control sequence regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cistemae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see also Hancock et al., *EMBO J.* 10:4033-4039, 1991; Buss et al., *Mol. Cell. Biol.* 8:3960-3963, 1988; and U.S. Pat. No. 5,776,689; each of which is incorporated herein by reference).

The term "operatively linked" or "operably linked" or "operatively joined" or the like, when used to describe chimeric (i.e., fusion) proteins, refer to polypeptide sequences that are placed in a physical and functional relationship to each other. In a most preferred embodiment, the functions of the polypeptide components of the chimeric protein are unchanged compared to the functional activities of the parts in isolation. For example, a fluorescent protein of the present invention can be fused to a polypeptide of interest. In this case, it is preferable that the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention. As used herein, the fusion proteins of the invention can be in a monomeric state, or in a multimeric state (e.g., dimeric).

As used herein, the term "brightness," with reference to a fluorescent protein, is measured as the product of the extinction coefficient (EC) at a given wavelength and the fluorescence quantum yield (QY).

As used herein, the term "IR" or "infrared" includes wavelengths in the infrared and far red spectrum. One of skill in the art is able to measure the emission wavelength of each of the fluorescent molecules described herein to determine whether an individual molecule should be classified as infrared or far red.

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound.

The term "label" refers to a composition that is detectable with or without instrumentation, for example, by visual inspection, spectroscopy, or a photochemical, biochemical, immunochemical, or chemical reaction. Useful labels include, for example, phosphorus-32, a fluorescent dye, a fluorescent protein, an electron-dense reagent, an enzyme such as is commonly used in an ELISA, or a small molecule (such as biotin, digoxigenin, or other haptens or peptides) for which an antiserum or antibody, which can be a monoclonal antibody, is available. It will be recognized that a fluorescent protein variant of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and the isolation of the expressed protein, respectively. A label useful for purposes of the present invention generally generates a measurable signal such as a radioactive signal, fluorescent light, enzyme activity, and the like, either of which can be used, for example, to quantitate the amount of the fluorescent protein variant in a sample.

The term "polypeptide" or "protein" refers to a polymer of two or more amino acid residues. The terms apply to amino acid polymers in which one or more amino acid residue is an artificial, chemical analogue of a corresponding naturally occurring amino acid, as well as to polymers of naturally occurring amino acids. The term "recombinant protein" refers to a protein that is produced by expression of a nucleotide sequence encoding the amino acid sequence of the protein from a recombinant DNA molecule.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

The term "immunoassay" refers to an assay that utilizes an antibody to specifically bind an analyte. An immunoassay is characterized by the use of specific binding properties of a particular antibody to isolate, to target, or to quantify the analyte.

The term "identical" or "identity" or "percent identity," or "sequence identity" in the context of two or more nucleic acids or polypeptide sequences that correspond to each other refer to two or more sequences or subsequences that are the same or have a specified percentage of amino acid residues or nucleotides that are the same (e.g., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical" and are embraced by the term "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists for a specified entire sequence or a specified portion thereof or over a region of the sequence that is at least about 25 amino acids or nucleotides in length, or more preferably over a region that is 50-100 amino acids or nucleotides in length. A corresponding region is any region within the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted (e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein.

Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K)
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 90% sequence identity with each other, or with a reference sequence over a given comparison window. Thus, substantially similar sequences include those having, for example, at least 90% sequence identity, at least 95% sequence identity, at least 97% sequence identity, or at least 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature, under defined ionic strength and pH, at which 50% of the target sequence hybridizes to a perfectly matched probe.

Fluorescent molecules are useful in fluorescence resonance energy transfer (FRET), which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize Ro, which represents the distance at which energy transfer efficiency is 50%. However, the excitation spectra of the donor and acceptor should overlap as little as possible so that a wavelength region can be found at which the donor can be excited efficiently without directly exciting the acceptor: Fluorescence arising from direct excitation of the acceptor can be difficult to distinguish from fluorescence arising from FRET. Similarly, the emission spectra of the donor and acceptor should overlap as little as possible so that the two emissions can be clearly distinguished. High-fluorescence quantum yield of the acceptor moiety is desirable if the emission from the acceptor is to be measured either as the sole readout or as part of an emission ratio. One factor to be considered in choosing the donor and acceptor pair is the efficiency of FRET between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type Bradyrhizobium fluorescent proteins and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" or "FP" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of the Bradyrhizobium sp. phytochrome can be derived from the naturally occurring phytochrome by engineering mutations such as amino acid substitutions into the reference protein.

The term "infrared fluorescent protein," or "IFP" is used in the broadest sense. Although it specifically covers the Bradyrhizobium sp. ORS278 phytochrome BrBphP, it also refers to fluorescent proteins from any other species and variant proteins thereof as long as they retain the ability to fluoresce infrared light.

As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 80%, or at least about 85%, 86%, 87%, 88%, 89%, 90%, 91%, 92%, 93%, 94%, 95%, 96%, 97%, 98%, 99%, or more sequence identity with the reference fluorescent protein, and particularly has a contiguous sequence of at least about 200 amino acids that shares at least about 95% sequence identity with the reference fluorescent protein. In yet other embodiments, the related fluorescent protein may be compared over a region of about 50, or about 75, 100, 125, 150, 200, 250, 300, 350, or the full-length of the protein.

As used herein, the term "IFP-conjugate" and "fusion protein" refer to an IFP protein that is conjugated to a moiety. In certain embodiments the moiety targets a specific protein. For example, an IFP-conjugate can be an IFP-antibody conjugate. In a second non-limiting example, the IFP-conjugate can be an IFP-protein conjugate (e.g., a protein that localizes in particular organelles of a cell or an protein that binds to receptors of cells). For example, the IFP can be genetically engineered to express on a cytosolic protein to target and label the cytosol of transfected cell. An IFP-protein conjugate may also be an IFP that is conjugated to a ligand that binds certain receptors (e.g., EGFR) that are differentially expressed on cancer cells. The IFP-conjugate can be a genetically encoded conjugate such as a single polynucleotide that encodes a chimeric protein (e.g., an actin-IFP or ligand-IFP chimera). Alternatively, the IFP-conjugate can be formed from one or more covalent bonds. For example, an IFP can be linked to an antibody by one or more disulfide bonds.

The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein.

The term "substitution" refers to includes the replacement of one or more amino acid residues either by other naturally occurring amino acids, (conservative and non-conservative substitutions), by non-naturally occurring amino acids (conservative and non-conservative substitutions), or with organic moieties which serve either as true peptidoniimetics (e.g., having the same steric and electrochemical properties as the replaced amino acid), or merely serve as spacers in lieu of an amino acid, so as to keep the spatial relations between the amino acid spanning this replaced amino acid.

Infrared Fluorescent Proteins

The mIFPs of the present invention replace or supplement existing GFP and RFP variants in many applications because the near-infrared wavelengths of fluorescence with biliverdin as cofactor penetrate thick and pigmented tissue much better, have less background due to cellular autofluorescence, are more easily excited by cheap and versatile semiconductor light sources such as laser diodes, and can be detected with no interference from most standard fluorophores. The ability to load the same protein with protoporphyrin IX adds the possibility of correlated electron-microscopic visualization (e.g., usage as a contrast agent), detection and measurement of long-range protein-protein interactions, and controlled photoablation of the host cell or protein. A great many different phytochromes exist in bacteria and plants, so there is abundant raw material from which to evolve other IFPs.

mIFPs can be imaged over spatial scales from subcellular resolution up to strongly pigmented organs within intact whole mammals, whereas luciferase-based bioluminescence is useful mainly for whole-body imaging (C. H. Contag, M. H. Bachmann, *Annu. Rev. Biomed. Eng.* 4, 235 (2002)). The wavelengths of mIFPs are particularly well-suited to optical tomographic reconstruction (V. Ntziachristos et al., *Proc. Natl. Acad. Sci. U.S.A.* 101, 12294 (2004)). Even for microscopic imaging where existing fluorescent proteins are highly effective, mIFPs should reduce the contribution of cellular autofluorescence, enable excitation by cheap laser diodes, add new wavelengths for multicolor labeling, and accept resonance energy transfer from other dyes, fluorescent proteins, or bioluminescent proteins.

The usefulness of mIFPs in protein localization and trafficking may enable new medical, surgical, or diagnostic uses for in vivo imaging. For example, mIFPs that are localized in cancer cells could be used to guide excision of tumor bodies and margins during surgery, as the resulting fluorescence would indicate the boundaries of the tumor's infiltration into healthy tissue.

Biliverdin ("BV") is uniquely advantageous as a cofactor because it is spontaneously and irreversibly incorporated into bacteriophytochromes, nontoxic at appropriate doses (R. Ollinger et al., *Antioxid. Redox. Signal* 9, 2175 (2007); N. Atsunori et al., *Gastroenterology* 127, 595 (2004)), nonfluorescent by itself, endogenously produced, and can be further supplemented either by expression of heme oxygenase or by direct administration of commercially available material. Heme oxygenase is an important enzyme in its own right and is involved in various diseases (N. G. Abraham, A. Kappas, *Pharmacol. Rev.* 60, 79 (2008)). Its cumulative activity could be monitored by mIFP fluorescence if apoprotein expression were in excess over BV.

More than 1500 bacteriophytochrome-like sequences are already available in the NCBI and CAMERA databases (D. B. Rusch et al., *PLoS Biol.* 5, e77 (2007)). These genes should provide raw material for selection and directed evolution of photochemical transducers based on a scaffold completely independent of the 11-stranded beta-barrel of coelenterate fluorescent proteins.

Infrared Fluorescent Protease Sensors

The Infrared Fluorescent Protease Sensors ("iProteases") of the present invention are genetically encoded infrared fluorescent protease sensors (see e.g., FIGS. 1-5, Examples 1-4, and Sequences).

In the "inactive" state, the iProtease is not infrared fluorescent. Once the protease cleavage sequence is recognized and cleaved by its protease, the catalytic cysteine can then move back to the binding cavity and the chromophore can be incorporated into the protein. Therefore, once activated by its protease, the "active" iProtease becomes infrared fluorescent. On the other hand, both "inactive" and "active" iProtease is green fluorescent from the recombined split GFP, independent of the protease's activity, which can be used to monitor the expression of the sensor in cells.

The iProteases was engineered from mIFP. The sensor became infrared fluorescent upon cleavage by the specific protease. The sensor also contains a GFP variant (Split GFP), which is constitutively fluorescent. Multiple iProteases were designed and constructed.

In one embodiment, iProteases were designed to detect the Tobacco Etch Virus (TEV) protease. These TEV protease sensors ("iTEV") contain the cleavage sequence ENLYFQS (SEQ ID NO:47) (followed by EF from the EcoRI restriction site). The iTEV was used as a platform for engineering better iProtease sensors. The signal of iTEV was improved by truncating the two domains of mIFP (PAS and GAF) near the cleavage site. Mutants generated as a result of truncation were (numbers in the parenthesis refer to the residue numbers in mIFP):

iTEV(+) 1.0—GAF(125-320)-cleavage site-PAS(13-124) (SEQ ID NOS:1 and 24)

iTEV(+) 2.1—GAF(125-320)-cleavage site-PAS(18-124) (SEQ ID NOS:2 and 25)

iTEV(+) 3.0—GAF(125-313)-cleavage site-PAS(18-124) (SEQ ID NOS:3 and 26)

iTEV(+) 3.1—GAF(125-314)-cleavage site-PAS(18-124) (SEQ ID NOS:4 and 27)

iTEV(+) 3.2—GAF(125-315)-cleavage site-PAS(18-124) (SEQ ID NOS:5 and 28)

iTEV(+) 3.3—GAF(125-316)-cleavage site-PAS(18-124) (SEQ ID NOS:6 and 29)

iTEV(+) 3.4—GAF(125-317)-cleavage site-PAS(18-124) (SEQ ID NOS:7 and 30)

iTEV(+) 3.5—GAF(125-318)-cleavage site-PAS(18-124) (SEQ ID NOS:8 and 31)

iTEV(+) 3.6—GAF(125-320)-cleavage site-PAS(18-124) (SEQ ID NOS:9 and 32)

The best variant from truncation was iTEV(+) 3.0 (referred to as "iTEV" herein). Further improvement of iTEV (+) 3.0 was done by random mutagenesis to yield the following improved mutants (residue number refers to the mIFP):

iTEV(+) 6.01—iTEV(+) 3.0 with 7 mutations: G176A C267S H292Q G297C I306N T58I M90V (SEQ ID NOS:10 and 33)

iTEV(+) 6.03—iTEV(+) 3.0 with 4 mutations: G176A I251V I306N M90V (SEQ ID NOS:11 and 34)

iTEV(+) 6.04—iTEV(+) 3.0 with 3 mutations: G176A I306N M90V (SEQ ID NOS:12 and 35)

iTEV(+) 6.05—iTEV(+) 3.0 with 7 mutations: G176A G297V E298D M90V (SEQ ID NOS:13 and 36)

iTEV(+) 6.13—iTEV(+) 3.0 with 4 mutations: G176A I251N I306A M90V (SEQ ID NOS:14 and 37)

The Split-GFP on iTEV(+) could be replaced by the K5 and E5 coils. Two variants were created:

iTEV(+) 5.1 (referred to as "iTEV (EK)" herein)—iTEV (+) 3.0, with Split GFP replaced by the K5 and E5 coils (SEQ ID NOS:15 and 38)

iTEV(+) 6.031—iTEV(+) 6.03, with Split GFP replaced by the K5 and E5 coils (SEQ ID NOS:16 and 39)

Other protease sensors were made be replacing the cleavage sequence in iTEV(+) with other cleavage sequences.

In another embodiment, iProteases were designed to detect Caspase 3 and/or Caspase 7 activity ("iCAS3(+) sensors"). The iCAS3(+) sensor was built to detect executioner caspases' (caspase 3/7) activity:

iCAS3(+) 3.0 (referred to as "iCAS3" and "iCasper" herein)—iTEV(+) 3.0 with ENLYFQS replaced by GDEVDG (SEQ ID NOS:17, 40, and 48)

iCAS3(+) 6.03—iTEV(+) 6.03 with ENLYFQS replaced by GDEVDG (SEQ ID NOS:18, 41, and 48)

iCAS3(+) 6.031—iTEV(+) 6.031 with ENLYFQS replaced by GDEVDG (SEQ ID NOS:19, 42, and 48)

In another embodiment iProteases were designed to detect Hepatitis C NS3 protease (the "iNS3(+) sensor"):

iNS3(+) 3.1 (referred to as "iHCV" herein)—iTEV(+) 3.0 with ENLYFQS replaced by EDVVCCSMS. (SEQ ID NOS: 20, 43, and 49)

iNS3(+) 3.2—iTEV(+) 3.0 with ENLYFQS replaced by EDVVCCSM (SEQ ID NOS:21, 44, and 50)

iNS3(+) 3.3—iTEV(+) 3.0 with ENLYFQS replaced by EDVVCCS (SEQ ID NOS:22, 45, and 51)

In another embodiment iProteases were designed to detect calpain activity (the "Calpain(+) sensor"):

iCalpain(+) 1.0—iTEV(+) 3.0 with ENLYFQSEF replaced by QQEVYGMMPRD (SEQ ID NOS:23, 46, and 52)

Preparation and Expression of Recombinant Nucleic Acids

To obtain high level expression of a cloned gene or genome, the nucleic acid can be cloned into an expression vector that contains a strong promoter to direct transcription, a transcription/translation terminator, and if for a nucleic acid encoding a protein, a ribosome binding site for translational initiation. Suitable bacterial promoters are well known in the art and described (e.g., in Sambrook et al., and Ausubel et al., supra. Bacterial expression systems for expressing the protein are available in, e.g., *E. coli*, *Bacillus* sp., and *Salmonella* (Palva et al., *Gene* 22:229-235 (1983)); Mosbach et al., *Nature* 302:543-545 (1983)). Kits for such expression systems are commercially available. Eukaryotic expression systems for mammalian cells, yeast, and insect cells are well known in the art and are also commercially available. Retroviral expression systems can be used in the present invention.

Selection of the promoter used to direct expression of a heterologous nucleic acid depends on the particular application. In certain embodiments the promoter is preferably positioned about the same distance from the heterologous transcription start site as it is from the transcription start site in its natural setting. As is known in the art, however, some variation in this distance can be accommodated without loss of promoter function. Accordingly, in certain embodiments the promoter is positioned to yield optimal expression of the protein encoded by the heterologous nucleic acid. Heterologous refers to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

In addition to the promoter, in certain embodiments the expression vector also contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. In certain embodiments, additional elements of the cassette can include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region can be obtained from the same gene as the promoter sequence or can be obtained from different genes.

One of skill in the art will know how to select an expression vector based on the size of the insert and the cell-type to be transfected or transformed. For example, any of the conventional vectors used for expression in eukaryotic or prokaryotic cells can be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags can be included in an expression cassette for nucleic acid rescue. Markers such as fluorescent proteins, green or red fluorescent protein, 13-gal, CAT, and the like can be included in the vectors as markers for vector transduction.

In certain embodiments, regulatory elements can be incorporated into the expression vectors. Expression vectors containing regulatory elements include but are not limited to SV40 vectors, papilloma virus vectors, retroviral vectors, and vectors derived from Epstein-Barr virus. Other exemplary eukaryotic vectors include but are not limited to pMSG, pAV009/A$^+$, pMT010/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

In certain embodiments expression of proteins from eukaryotic vectors can also be regulated using inducible promoters. With inducible promoters, expression levels are tied to the concentration of inducing agents, such as tetracycline, by the incorporation of response elements for these agents into the promoter. Generally, high level expression is obtained from inducible promoters only in the presence of the inducing agent; basal expression levels are minimal.

In certain embodiments, a multicistronic vector comprises a nucleic acid that encodes an IFP disclosed herein and one or more additional genes.

In certain embodiments the vector has a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

Additional elements that are incorporated into expression vectors include but are not limited to a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is based on various factors. For example, antibiotic resistance genes will be chosen and incorporated into an expression vector based on the organism and/or cell line that is to be transfected/transformed. In other examples, antibiotic resistance genes are chosen based on the a series of co-transfections and multi-gene selection criteria. The prokaryotic sequences are preferably chosen such that they do not interfere with the replication of the DNA in eukaryotic cells, if necessary.

Standard transfection and transformation techniques are known to one of skill in the art. These techniques can be used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). In certain embodiments, transformation and transfection of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (1983)).

Furthermore, one of skill in the art will know that any of the well-known procedures for introducing foreign nucleotide sequences into host cells (e.g., transformation or transfection) can be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing mIFP proteins and nucleic acids.

After the expression vector is introduced into the cells, the transfected cells are cultured under conditions favoring expression of the protein of choice, which is recovered from the culture using standard techniques identified below.

Both naturally occurring and recombinant mIFP proteins can be purified, for example, for use in diagnostic assays, for making antibodies (for diagnosis and therapy) and vaccines, and for assaying for anti-viral compounds. Naturally occurring protein can be purified from animal and plant tissue, e.g., from primate tissue samples. Recombinant protein can be purified from any suitable expression system.

Purification iProteases

The iProteases can be purified to substantial purity by standard techniques, including selective precipitation (e.g., with such substances such as ammonium sulfate), column chromatography, immunopurification methods, and other techniques known to one of skill in the art (see, e.g., Scopes, *Protein Purification: Principles and Practice* (1982); U.S. Pat. No. 4,673,641; Ausubel et a.l, supra; and Sambrook et al., supra).

A number of procedures known to one of skill in the art can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein can be purified using immunoaffinity columns. Recombinant protein can be purified from any suitable source, include yeast, insect, bacterial, and mammalian cells.

Recombinant proteins can be expressed and purified by transformed bacteria in large amounts, typically after promoter induction; but expression can be constitutive. For example, promoter induction with IPTG is one example of an inducible promoter system. Bacteria are grown according to standard procedures in the art. Fresh or frozen bacteria cells are used for isolation of protein.

Proteins expressed in bacteria can form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCl pH 7.5, 50 mM NaCl, 5 mM MgCl2, 1 mM DTT, 0.1 mM ATP, and 1 mM PMSF. One of skill in the art will know that the stability of the protein will determine the lysis and purification buffer components. For example, one of skill in the art will know that protease inhibitor cocktails can be used to minimize and/or prevent protein degradation. Such protease inhibitor cocktails may include but are not limited to PMSF. Similarly, one of skill in the art will know that detergents and/or surfactants may be added to prevent protein aggregation, to enhance purification, and increase solubilization. Specifically, non-ionic, zwitterionic, and ionic detergents can be used. Such detergents and surfactants include but are not limited to Tween, Triton (e.g., Triton X-100), octylglucoside, DM, DDM, Chaps, Zwittergents (e.g., zwittergent 3-12), sodium deoxycholate, and glycerol. Furthermore, one of skill in the art will know that reducing agents can be used to prevent aggregation and enhance purification of proteins. Reducing agents include, but are not limited to, 2-mercaptoethanol, DTT, and TCEP. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies can be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation can occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Solubility fractionation can be used as a standard protein separation technique for purifying proteins. As an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates using column chromatography. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

The invention provides kits for practicing the assays described herein. Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize the proteins encoded by the biomarkers of the invention.

Diagnostic Tests & Imaging

In certain embodiments, a nucleic acid encoding any of the iProteases described herein, is used in an energy transfer experiment, wherein the energy transfer experiment is selected from the group consisting of fluorescence resonance energy transfer (FRET), luminescence resonance energy transfer (LRET), and bioluminescence resonance energy transfer (BRET). In certain embodiments, the iProteases used in an energy transfer experiment is supplied in a kit In certain embodiments, the nucleic acid to any of the iProteases described herein is used in a fluorescence resonance energy transfer (FRET) assay. In certain embodiments the assay comprises: a set of probes comprising at least a first and a second molecular probe, each molecular probe able to specifically bind a molecule of interest and each molecular probe associated with a fluorescent protein or dye, together, the dyes allow energy transfer, wherein at least one molecular probe comprises a reactive group to modulate the spatial organization of the molecular probes after binding to the molecule of interest; wherein the reactive group is not involved in binding to the molecule of interest; and wherein at least one of the fluorescent proteins is encoded by a nucleic acid that encodes one of the iProteases described herein.

In certain embodiments, the nucleic acid that encodes any of the iProteases described herein is used as a detection probe. In certain embodiments, any of the iProteases described herein is used as a detection probe for an in vitro diagnostic assay or test. In certain embodiments, any of the iProteases described herein is used as a detection probe for an in vivo diagnostic assay or test. In certain embodiments, the in vivo diagnostic assay or test is performed in a whole, living animal.

In certain embodiments, any of the iProteases described herein is used as a detection probe for an ex vivo diagnostic assay or test.

In certain embodiments, the iProteases is conjugated to an antibody, a receptor, or a ligand. In certain embodiments, the antibody, receptor, or ligand detects a specific protein or cell type associated with a disease. In certain embodiments, the iProteases detection probes are used to detect and diagnose a disease. In certain embodiments, the iProteases detection probes are used to track the progression of a disease. In certain embodiments, the iProteases detection probes are used to determine the prognosis of a disease based on disease state and progression. In certain embodiments, the iProteases detection probes are used to track and determine the efficacy of a drug(s) and/or therapy(ies) in the treatment of a disease.

In certain embodiments the disease is a proliferative disease. In certain embodiments the disease is a muscle-related disease. In certain embodiments the disease is a gastro-intestinal related disease. In certain embodiments the disease is an inflammatory disease. In certain embodiments the disease is a neurological disease. In certain embodiments the disease is an ocular disease. In certain embodiments the disease is an autoimmune disease.

In certain embodiments, the iProteases is conjugated to an antibody, a receptor, or a ligand that binds to and detects a cancer-related protein. In certain embodiments, the iProteases is conjugated to an antibody, receptor, or ligand that binds to and detects a cancer cell biomarker that is expressed on the extracellular side of a cancer cell. In certain embodiments, the iProteases detection probes are used to detect and diagnose cancer. In certain embodiments, the iProteases detection probes are used to track the progression of a cancer. In certain embodiments, the iProteases detection probes are used to determine the prognosis of a cancer based on disease state and progression. In certain embodiments, the iProteases detection probes are used to track and determine the efficacy of a drug(s) and/or therapy(ies) in the treatment of a cancer. In certain embodiments the cancer is breast cancer, brain cancer, colon cancer, melanoma, leukemia (e.g., AML), pancreatic cancer, prostate cancer, ovarian cancer, lung cancer, and/or gastric cancer.

In certain embodiments, a pair of detection probes can be used for use in a diagnostic assay or test wherein one or more of the detection probes is one of the iProteasess disclosed herein.

In certain embodiments, the iProteasess described herein are used for fluorescent spectroscopy. In certain embodiments, the spectroscopy is in vitro spectroscopy. In certain embodiments, the spectroscopy is in vivo spectroscopy. In certain embodiments, the spectroscopy is ex vivo spectroscopy.

In certain embodiments the iProteases-conjugates target and bind to tumor cells. In certain embodiments the iProteases-conjugates are used for in vivo imaging during a surgical procedure to trace the boundaries of a tumor for tumor rescission. In certain embodiments the iProteases-conjugates are used for in vivo imaging to trace the boundaries of a tumor in preparation for external radiation therapy.

In certain embodiments, the iProteasess described herein are used for a time-resolved fluorescence immunoassay for multiple analytes. In certain embodiments, the time-resolved fluorescence immunoassay for multiple analytes, comprises the steps of: (a) forming an incubation mixture of: (i) antibodies against each analyte; (ii) a predetermined amount of fluorescently labeled analytes wherein each fluorescently labeled analyte has a different fluorescene lifetime; and (iii) a sample to be tested; (b) incubating the mixture under conditions and for a period of time sufficient for antibody and analytes to complex; and (c) determining contemporaneously the amount of each fluorescently labeled analyte bound with antibody as an indication of the amount of each corresponding analyte in the sample, by (i) exciting the fluorescently labeled analyte with a light pulse; and (ii) determining the amplitude of each fluorescence decay curve for the antibody-bound fluorescently labeled analyte by a single amplitude measurement measuring all of the fluorescence reaching the detector from the instant of excitation; wherein the fluorescently labeled analytes are labeled with a fluorophore encoded by a nucleic acid that encodes any of the iProteasess described herein.

Companion Diagnostics

In other embodiments, this disclosure relates to companion diagnostic methods and products.

In one embodiment, the companion diagnostic method and products can be used to monitor the treatment of cancer. In a specific embodiment, the companion diagnostic method and products can be used to monitor the treatment of breast cancer. In a specific embodiment, the companion diagnostic method and products can be used to monitor the treatment of an autoimmune disease. In one embodiment, the companion diagnostic method and products can be used to monitor the treatment of brain cancer, colon cancer, melanoma, leukemia (e.g., AML), pancreatic cancer, prostate cancer, ovarian cancer, lung cancer, and/or gastric cancer. In one embodiment, the companion diagnostic method and products can be used to monitor the treatment of viral diseases. In one embodiment, the companion diagnostic method and products can be used to monitor the treatment of retroviral diseases.

In some embodiments, the companion diagnostic methods and products include molecular assays to measure levels of proteins, genes or specific genetic mutations. Such measurements can be used, for example, to predict whether a cancer drug or therapy will benefit a specific individual, to predict the effective dosage of a cancer drug or therapy, to monitor a cancer drug or therapy, adjust a cancer drug or therapy, tailor a cancer drug or therapy to an individual, and track cancer progression and remission.

As used herein, the terms "cancer drug" and "cancer therapy" refer to a single agent or a cocktail of agents administered to treat a cancer patient. The terms include, but are not limited to chemotherapy, radiotherapy, hormonal therapy, immunotherapy, and/or radiation.

Conventional chemotherapeutic agents include but are not limited to alkylating agents (e.g., cisplatin, cyclophosphamide, carboplatin, ifosfamide, chlorambucil, busulfan, thiotepa, nitrosoureas, etc.), anti-metabolites (e.g., 5-fluorouracil, azathioprine, methotrexate, fludarabine, etc.), plant alkaloids (e.g., vincristine, vinblastine, vinorelbine, vindesine, podophyllotoxin, paclitaxel, docetaxel, etc.), topoisomerase inhibitors (e.g., amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, plicamycin, etc.), and the like.

Conventional hormonal therapeutic agents include, but not limited to, steroids (e.g., dexamethasone), finasteride, aromatase inhibitors, tamoxifen, and gonadotropin-releasing hormone agonists (GnRH) such as goserelin.

Conventional immunotherapeutic agents include, but not limited to, immunostimulants (e.g. *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., monoclonal antibodies which are conjugated to $^{111}$In, $^{90}$Y, or $^{131}$I).

Conventional radiotherapeutic agents include, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$mSn, $^{149}$Pm, $^{153}$Sm, $^{166}$Ho, $^{177}$Lu, $^{186}$Re, $^{188}$Re, $^{211}$At, and/or $^{212}$Bi, optionally conjugated to antibodies directed against tumor antigens.

Non-limiting examples of radiation therapy include but are not limited to x-ray therapy, gamma ray (gamma knife) therapy, and charged particle therapy. The radiation therapies may be administered via external-beam radiation or internally (i.e., internal radiation therapy or brachytherapy).

In certain embodiments, the iProteases described herein can be used to develop an individualized radiation plan for a patient. For example, a patient may be administered an IFP-antibody conjugate that bind cancer cells for detection using CT, MRI, PET, and Fluorescent Scan imaging.

In some embodiments, the compositions of the present invention comprise IFPs and IFP-conjugates and a physiologically (i.e., pharmaceutically) acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid, solid, or semi-solid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Examples of solid or semi-solid carriers include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. Since physiologically acceptable carriers are determined in part by the particular composition being administered as well as by the particular method used to administer the composition, there are a wide variety of suitable formulations of pharmaceutical compositions of the present invention (see, e.g., Remington's Pharmaceutical Sciences, 17.sup.th ed., 1989).

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, eg., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged iProteases-conjugate suspended in diluents, e.g., water, saline, or PEG 400; (b) capsules, sachets, or tablets, each containing a predetermined amount of a iProteases-conjugate, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise an iProteases-conjugate in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The iProteases-conjugate may be made into aerosol formulations (i.e., "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged iProteases-conjugate with a suppository base. Suitable suppository bases include natural or synthetic triglycerides or paraffin hydrocarbons. In addition, it is also possible to use gelatin rectal capsules which contain a combination of the iProteases-conjugate of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a iProteases-conjugate. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

EXAMPLES

The methods system herein described are further illustrated in the following examples, which are provided by way of illustration and are not intended to be limiting.

Example 1: Rational Design of an Infrared Fluorescent Protease Reporter

To regulate the BV incorporation by protease activity, the specific physical and chemical mechanisms of BV binding to BphP-derived IFPs were harnessed. Specifically, the catalytic cysteine is physically close to the BV-binding cavity in the GAF domain, so that after noncovalent binding of BV, it can readily form a thioether bond with the A-ring vinyl group of BV. Thus, the physical proximity of the catalytic cysteine to the binding cavity is essential for the chromophore incorporation.

In order to prove that the role of the catalytic cysteine, the IFP was modified to change the cysteine's proximity to the binding cavity to show that the incorporation of BV may be abolished and the protein may become non-fluorescent.

To pull the catalytic cysteine away from the binding cavity, the IFP was redesigned (FIG. 1B). First, a circular permutation was made to IFP so that the old amino (N) and carboxyl (C) terminus were linked together by a protease cleavage sequence (dashed line), with a new opening between PAS and GAF domains. Then the N (large box) and C (small box) parts of split GFP were added to the new N and C terminus of the circular permutated IFP, respectively. See Cabantous, S., Terwilliger, T. C. & Waldo, G. S. Protein tagging and detection with engineered self-assembling fragments of green fluorescent protein. *Nat Biotechnol* 23, 102-107 (2005) which is incorporated herein by reference. This ensures that after protease cleavage, the redesigned IFP will not "fall apart". Lastly, the old N and C terminus was truncated so that the distance between the catalytic cysteine and the carboxyl end of the GAF is larger than the length of protease cleavage sequence. This results in the catalytic cysteine being pulled away from the binding cavity, and the chromophore can no longer be incorporated.

At this "inactive" state, the designed infrared fluorescent protease sensor ("iProtease") is not infrared fluorescent. Once the protease cleavage sequence is recognized and cleaved by its protease, the catalytic cysteine can then move back to the binding cavity and the chromophore can be incorporated into the protein. Therefore, once activated by its protease, the "active" iProtease becomes infrared fluorescent. On the other hand, both "inactive" and "active" iProtease is green fluorescent from the recombined split GFP, independent of the protease's activity, which can be used to monitor the expression of the sensor in cells.

As a proof of concept, an infrared fluorescent Tobacco Etch Virus (TEV) protease sensor ("iTEV") was designed by inserting the TEV cleavage sequence into the iProtease scaffold. iTEV was expressed in Human Embryonic kidney 293 (HEK293) cells. The transfected cells were green fluorescent but not infrared fluorescent (FIG. 1C), consistent with an inactive iTEV. With co-expression of the TEV protease, the transfected cells were both green and infrared fluorescent, consistent with an active iTEV (FIG. 1C). Both green and infrared fluorescence require no exogenous cofactor, and thus the sensor is genetically encoded. Other subject TEV protease sensors were also tested using this proof of concept model (iTEV(+) 6.01, 6.03, 6.04, and 6.05)) and confirmed for activity in the presence of TEV protease (FIG. 5).

Example 2: Characterization of iProtease

To confirm working mechanism of the iProtease, the "active" and "inactive" iTEV were purified and their spectra were measured. The "active" iTEV has two main absorbance peaks at 480 and 680 nm (FIG. 2A and FIG. 2B). The former is characteristic of the split GFP's absorbance; the latter is typical of the IFP's absorbance. On the other hand, the "inactive" iTEV has only one absorbance peak at 480 nm (FIG. 2B). This indicates that the "inactive" sensor does not incorporate the chromophore but the "active" iTEV does, consistent with our design. Excitation of the short-wavelength peak resulted in green fluorescence for both "active" and "inactive" sensors with emission maximum at 510 nm (FIG. 2C), which is the feature of GFP fluorescence. While the "active" iTEV is infrared fluorescent upon excitation at 640 nm, the "inactive" iTEV is not fluorescent at this wavelength (FIG. 2C). The fluorescence spectra are consistent with the imaging results from HEK293 cells, as well as the absorbance spectra.

The kinetics of BV binding to the activated sensor was measured. BV was added to the cleaved iTEV purified from *E. coli* in the absence of BV, and monitored the infrared fluorescence as a function of time (FIG. 2D). The infrared fluorescence rose within 10 seconds, suggesting a rapid binding of BV to the activated sensor.

Gel electrophoresis was performed to determine whether the chromophore incorporation is covalent for the "active" iTEV purified from *E. coli* in a mixture of iTEV, TEV and BV. The N-half of the sensor is expected to be 46 kDa and the C-half 15 kDa. Two bands revealed by Coomassie blue staining correspond to N and C half of the sensor with the expected molecular weight (FIG. 2E). Zinc-induced fluorescence assay was also performed (FIG. 2E, bottom panel), which is a standard assay in characterizing covalent incorporation of bilin into phytochromes, based on the phenomena that bilin-zinc ion complex is orange fluorescent upon UV illumination (Berkelman, T. R. & Lagarias, J. C. Visualization of bilin-linked peptides and proteins in polyacrylamide gels. *Analytical Biochemistry* 156, 194-201 (1986)). Zinc-induced orange fluorescence was observed at the same position as the C-half protein band was visualized by Coomassie blue staining, demonstrating that BV is covalently incorporated since the proteins were denatured in the assay. As a control, no orange fluorescence was observed in the absence of BV (FIG. 2E).

The dependence of iProtease on the length of the protease cleavage sequence that links the catalytic cysteine and the carboxyl end of the GAF domain was also studied (FIG. 2A). According to this design, if the cleavage sequence is increased, eventually the "inactive" sensor will become fluorescent. In the iTEV, the cleavage sequence has 9 amino acids (7 amino acids of the TEV consensus sequence plus 2 additional amino acids resulted from a cloning site). To study the length dependence, 6 iTEV derivatives were generated where the cleavage sequences ranged from 10 to 15 amino acids. The iTEV and iTEV derivatives were expressed in HEK293 cells and their fluorescence was characterized. The inactive iTEV derivatives remained non-fluorescent in the IFP channel with the cleavage sequence up to 11 amino acids (11 aa) (FIG. 2F and FIG. 2G). They became infrared fluorescent at 12 aa and the fluorescence increased and saturated at 14 aa. When the TEV was co-expressed, all the derivatives were infrared fluorescent. These results confirm the "pulling" mechanism designed into iProtease.

Finally protease specificity was examined. A Hepatitis C Virus (HCV) NS3/4A protease sensor ("iHCV") was created. Then either iTEV or iHCV was expressed with or without co-expression of the TEV or HCV protease. It was found that iTEV is only activated by the TEV protease, whereas iHCV is only activated by the HCV protease (FIG. 2H). These results demonstrate that the rational design of iProtease achieves specificity, consistent with the mechanism behind the invention described herein.

Example 3: iCasper Visualizes Apoptosis in Cultured Cells

After verification and characterization of the iProtease design, iCasper was created using the consensus sequence DEVDG of executioner caspases (FIG. 3A and FIG. 3B). iCasper was expressed in the human glioblastoma LN229 cells. The transfected cells were green fluorescent but not infrared fluorescent. Upon addition of staurosporine (STS), which induces apoptosis by activating caspase 3 (Chae, H. J. et al. Molecular mechanism of staurosporine-induced apoptosis in osteoblasts. *Pharmacol. Res.* 42, 373-381 (2000)), iCasper became infrared fluorescent between 3 and 6 hours after the addition (FIG. 3C). This is consistent with previous results that activation of apoptosis in single cells vary from 3 to 6 hours after addition of STS (Albeck, J. G. et al. Quantitative Analysis of Pathways Controlling Extrinsic Apoptosis in Single Cells. *Mol Cell* 30, 11-25 (2008); Rehm, M. Single-cell Fluorescence Resonance Energy Transfer Analysis Demonstrates That Caspase Activation during Apoptosis Is a Rapid Process. ROLE OF CASPASE-3. *Journal of Biological Chemistry* 277, 24506-24514 (2002)).

Example 4: The Split GFP in iProtease can be Replaced by Other Motifs that Interact Each Other The split GFP that was designed to hold the two parts of mIFP together can be replaced by other interacting motifs, including, but not limited to, leucine zipper domains and heterodimeric coiled coils.

For example, heterodimeric coiled coils were used to replace split GFP in iTEV (De Crescenzo, G., Litowski, J. R., Hodges, R. S. & O'Connor-McCourt, M. D. Real-Time Monitoring of the Interactions of Two-Stranded de NovoDesigned Coiled-Coils: Effect of Chain Length on the Kinetic and Thermodynamic Constants of Binding †. *Biochemistry* 42, 1754-1763 (2003)). The resulted sensor, iTEV (EK), is not infrared fluorescent without TEV protease and becomes infrared fluorescent when TEV protease is co-expressed in the cells (FIG. 4).

What is claimed is:

1. A polypeptide comprising at least 90% identity to an amino acid sequence selected from the group consisting of SEQ ID NOs:24-46,
   wherein the polypeptide comprises an infrared fluorescent protein (IFP) PAS domain, an infrared fluorescent protein (IFP) GAF domain, a first split green fluorescent protein (GFP) domain, a second split green fluorescent protein (GFP) domain, and a protease cleavage site,
   wherein the first split GFP domain is attached to the IFP PAS domain, the second split GFP domain is attached to the IFP GAF domain and the IFP PAS and IFP GAF domains are joined by the protease cleavage site, and
   wherein infrared fluorescence is emitted upon cleavage of the protease cleavage site.

2. The polypeptide of claim 1, wherein the polypeptide comprises at least 95% identity to an amino acid sequence selected from the group consisting of SEQ ID NOs:24-46.

3. The polypeptide of claim 1, wherein the polypeptide comprises an amino acid sequence selected from the group consisting of SEQ ID NOs:24-46.

4. An isolated polynucleotide encoding a polypeptide according to any one of claim 1, 2, or 3.

5. A vector comprising the polynucleotide sequence of claim 4.

6. A host cell comprising the vector of claim 5.

7. A method of in vivo optical imaging the protease activity of a protease in a cell, the method comprising the step of: expressing in the cell a polynucleotide encoding a polypeptide, the polypeptide encoded by a polynucleotide of claim 4, wherein infrared fluorescence is emitted upon cleavage of the protease cleavage site by the protease.

8. The method of claim 7, wherein the cell is a bacterial or mammalian cell.

9. A method of detecting protease activity of a protease, the method comprising expressing a polypeptide of claim 1 in cell, wherein the polypeptide is cleaved at the protease cleavage site in the presence of protease and wherein the polypeptide emits infrared fluorescent upon cleavage.

10. The method of claim 9, wherein the polypeptide is selected from the group consisting of SEQ ID NOs:24-39 and the protease is a tobacco etch virus protease.

11. The method of claim 9, wherein the polypeptide is selected from the group consisting of SEQ ID NOs:40-42 and the protease is a caspase protease.

12. The method of claim 11, wherein the caspase protease is a caspase 3 protease.

13. The method of claim 11, wherein the caspase protease is a caspase 7 protease.

14. The method of claim 9, wherein the polypeptide is selected from the group consisting of SEQ ID NOs:43-45 and the protease is a Hepatitis C NS3 protease.

15. The method of claim 9, wherein the polypeptide is SEQ ID NO:46 and the protease is a calpain protease.

16. A method of detecting caspase mediated apoptosis, the method comprising expressing an infrared fluorescent protease reporter that has an amino acid sequence comprising at least 90% identity to an amino acid sequence selected from the group consisting of SEQ ID NOs:40-42 in a cell, wherein the infrared fluorescent protease reporter fluoresces upon cleavage by caspase in response to caspase mediated apoptosis.

17. A method of claim 16, wherein the infrared fluorescent protease reporter that has an amino acid sequence selected from the group consisting of SEQ ID NOs:40-42.

18. A method of detecting calpain activity, the method comprising expressing an infrared fluorescent protease reporter that has an amino acid sequence comprising at least 90% identity to amino acid sequence of SEQ ID NO:46 in a cell, wherein the infrared fluorescent protease reporter fluoresces upon cleavage by calpain.

19. A method of claim 18, wherein the infrared fluorescent protease reporter that has an amino acid sequence of SEQ ID NO:46.

* * * * *